US 7,375,168 B2

(12) United States Patent
Zhang et al.

(10) Patent No.: US 7,375,168 B2
(45) Date of Patent: *May 20, 2008

(54) PROTEIN COMPATIBLE METHODS AND COMPOUNDS FOR CONTROLLING THE MORPHOLOGY AND SHRINKAGE OF SILICA DERIVED FROM POLYOL-MODIFIED SILANES

(75) Inventors: Zheng Zhang, Hamilton (CA); Yang Chen, Hamilton (CA); Jorge Cruz-Aguado, Hamilton (CA); Richard J. Hodgson, Burlington (CA); Dina Tleugabulova, Hamilton (CA); John D. Brennan, Dundas (CA); Michael A. Brook, Ancaster (CA)

(73) Assignee: McMaster University, Hamilton, Ontario ( * ) Notice: Subject to any disclaimer, the term of this patent is extended or adjusted under 35 U.S.C. 154(b) by 0 days.

This patent is subject to a terminal disclaimer.

(21) Appl. No.: 10/814,123

(22) Filed: Apr. 1, 2004

(65) Prior Publication Data

US 2004/0249082 A1 Dec. 9, 2004

Related U.S. Application Data

(63) Continuation-in-part of application No. PCT/CA03/01257, filed on Aug. 25, 2003.

(60) Provisional application No. 60/484,298, filed on Jul. 3, 2003, provisional application No. 60/405,308, filed on Aug. 23, 2002, provisional application No. 60/405,309, filed on Aug. 23, 2002.

(51) Int. Cl.
*C08L 83/02* (2006.01)

(52) U.S. Cl. .................. 525/474; 528/39; 528/34

(58) Field of Classification Search ........... 525/474; 528/39, 34
See application file for complete search history.

(56) References Cited

U.S. PATENT DOCUMENTS

| 3,189,662 | A | | 6/1965 | Vaughn |
| 3,374,103 | A | * | 3/1968 | Barkin .............. 106/155.2 |
| 3,997,501 | A | | 12/1976 | McLeod |
| 4,588,624 | A | | 5/1986 | Nygren et al. |
| 4,673,584 | A | | 6/1987 | Nygren et al. |
| 5,009,688 | A | * | 4/1991 | Nakanishi ............. 65/17.2 |
| 5,071,674 | A | | 12/1991 | Nogues et al. |
| 5,074,916 | A | | 12/1991 | Hench et al. |
| 5,100,841 | A | | 3/1992 | Wada et al. |
| 5,243,769 | A | | 9/1993 | Wang et al. |
| 5,300,564 | A | | 4/1994 | Avnir et al. |
| 5,624,875 | A | * | 4/1997 | Nakanishi et al. ........ 501/39 |
| 5,637,507 | A | | 6/1997 | Wicks et al. |
| 5,728,457 | A | | 3/1998 | Frechet et al. |
| 6,048,546 | A | | 4/2000 | Sasaki et al. |
| 6,080,402 | A | | 6/2000 | Reetz et al. |
| 6,090,448 | A | | 7/2000 | Wallace et al. |
| 6,171,986 | B1 | | 1/2001 | Zhong et al. |
| 6,207,098 | B1 | | 3/2001 | Nakanishi et al. |
| 6,210,570 | B1 | | 4/2001 | Holloway |
| 6,303,290 | B1 | | 10/2001 | Liu et al. |
| 6,531,060 | B1 | | 3/2003 | Nakanishi et al. |
| 2001/0041459 | A1 | | 11/2001 | Smith et al. |
| 2004/0034203 | A1 | * | 2/2004 | Brook et al. ........... 530/402 |

FOREIGN PATENT DOCUMENTS

| CH | 327722 | 3/1958 |
| DE | 1136114 | 7/1960 |
| EP | 0363697 | 4/1990 |
| JP | 07102216 | 4/1995 |
| WO | WO 98/29350 | 7/1998 |
| WO | WO 01/01139 | 1/2001 |
| WO | WO 01/58562 | 8/2001 |

OTHER PUBLICATIONS

Gill et al. Chem. Mater. (2001), 13, pp. 3404-3421.*
Gill et al., J. Am. Chem. Soc., (1998), 120, pp. 8587-8598.*
Cabrera, K. et al., "SilicaROD™—A new challenge in fast high-performance liquid chromatography separations", Trends in Analytical Chemistry, 1998, pp. 50-53, vol. 17, No. 1.
Tanaka, N. et al., "Monolithic Silica Columns for HPLC, Micro-HPLC, and CEC", J. High Resol. Chromatogr., 2000, pp. 111-116, vol. 23, No. 1.
Ishizuka, N. et al., "Preparation and Chromatographic Application of Macroporous Silicate in a Capillary", Journal of Sol-Gel Science and Technology, 2000, pp. 371-375, vol. 19.
Motokawa, M. et al., "Monolithic silica columns with various skeleton sizes and through-pore sizes for capillary liquid chromatography", Journal of Chromatography A, 2002, pp. 53-63, vol. 961.
Ishizuka, N. et al., "Chromatographic characterization of macroporous monolithic silica prepared via sol-gel process", Colloids and Surfaces—A: Physicochemical and Engineering Aspects, 187-188, 2001, pp. 273-279.
Kang, J. et al., "A silica monolithic column prepared by the sol-gel process for enantiomeric separation by capillary electrochromatography", Electrophoresis, 2002, pp. 1116-1120, vol. 23.
Kikuta, K. et al., "Synthesis of Transparent Magadiite-Silica Hybrid Monoliths", Chem. Mater., 2002, pp. 3123-3127, vol. 14.

(Continued)

*Primary Examiner*—Kuo-Liang Peng
(74) *Attorney, Agent, or Firm*—Bereskin & Parr; Patricia Folkins

(57) ABSTRACT

Siliceous materials were prepared by adding one or more additives, including one or more water soluble polymers, and derivatives thereof, as well as trifunctional silanes, to sols containing tetraalkoxysilanes derived from polyols. The polymers facilitate phase separation of the growing silica gel matrix, leading to high surface area self-supporting silica gels with cure occurring at ambient temperatures. The materials also show a significant reduction in shrinkage properties and significant protein stabilization abilities.

74 Claims, 37 Drawing Sheets

OTHER PUBLICATIONS

Leinweber, F. C. et al., "Characterization of Silica-Based Monoliths with Bimodal Pore Size Distribution", Anal. Chem., 2002, pp. 2470-2477, vol. 74.

Nakanishi, K. et al., "Macropore Morphology Control of Silica Gel by Spinodal Decomposition", Chemical Processing of Advanced Materials, 1992, pp. 29-41.

Nakanishi, K. et al., "Macropore Structure Design of Sol-Gel Derived Silica by Spinodal Decomposition", Porous Materials, 1993, pp. 51-60.

Gill, I. et al., "Encapsulation of Biologicals within Silicate, Siloxane, and Hybrid Sol-Gel Polymers: An Efficient and Generic Approach", J. Am. Chem. Soc., 1998, pp. 8587-8598, vol. 120.

Gill, I., "Bio-doped Nanocomposite Polymers: Sol-Gel Bioencapsulates", Chem. Mater., 2001, pp. 3404-3421, vol. 13.

Nakanishi, K. et al., "Synthisis of silica gel by polymer-mixed sol-gel method", Chem. Abstracts, AN. 118:259529, Shinsozai (1992), pp. 44-49, vol. 3, No. 11.

Tanaka, N. et al., "Octadecylsilyated porous silica rod for reversed-phase liquid chromatography", Chem. Abstracts, AN. 121:92756, Kuromatogurafi (1993), pp. 50-51, vol. 14, No. 5.

Fyre, C.L., "Stable Silicon Heterocyclic Derivatives of Branced Alkanediols", The Journal of Organic Chemistry, 1969, pp. 2496-2499, vol. 34, No. 9.

Voronkov M.G. et al., Chem. Abst. No. 69:58787, "Spirocyclic orthosilicic acid esters", Z. Chem., 1968, pp. 252-253, vol. 8, No. 7.

Gainsford, G.J. et al., "Sodium Bis[1,2-ethanediolato(2-)](hydroxyethoxo)silicate(1-) Acetonitrile Solvate, $Na[Si(C_2H_4O_2)_2(C_2H_5O_2)].0.25C_2H_3N$", Acta Cryst., 1995, pp. 8-10, C51.

Müller, R. et al., Chem. Abst. No. 55:143332, "Silicones. LII. The identification and separation of alkoxy and aryloxy compounds with pentacovalent silicon", Chem. Berichte, 1961, pp. 1943-1951, vol. 94.

Kemmitt, T. et al., "The Ring Size Influence on $^{29}$Si N.M.R. Chemical Shifts of Some Spirocyclic Tetra- and Penta -coordinate Diolato Silicates", Aust. J. Chem., 1995, pp. 93-102, vol. 48.

Arsene, C. et al., "Cyclic Chiral Silyl Derivaties for the Determination of the Absolute Configuration of Aliphatic Diols by Gas Chromatography", Org. Lett., 2002, pp. 2869-2871, vol. 4, No. 17.

Spindler, R. et al., "Investigations of a Siloxane-Based Polymer Electrolyte Employing $^{13}$C, $^{29}$Si, $^{7}$Li, and $^{23}$Na Solid-State NMR Spectroscopy", J. Am. Chem. Soc., 1988, pp. 3036-3043, vol. 110.

Sattler, K. et al., Chem. Abst. No. 134: 195237, "A new glycol precursor for template synthesis and its interaction with a surfactant", Chemie Ingenieur Technik, 2000, pp. 487-491, vol. 72, No. 5.

Cheng, H. et al., "Neutral Alkoxysilanes from Silica", J. Am. Chem. Soc., 2000, pp. 10063-10072, vol. 122.

Kinrade S.D. et al., "Stable Five- and Six-Coordinated Silicate Anions in Aqueous Solution", Science, 1999, pp. 1542-1545, vol. 285.

Kinrade, S.D. et al., "Silicon-29 NMR evidence of alkoxy substituted aqueous silicate anions", J. Chem. Soc., Dalton Trans., 1999, pp. 3149-3150.

Kinrade, S.D. et al., "Aqueous hypervalent silicon complexes with aliphatic sugar acids", J. Chem. Soc., Dalton Trans., 2001, pp. 961-963.

Spindler, R. et al., "Synthesis, NMR Characterization, and Electrical Properties of Siloxane-Based Polymer Electrolytes", Macromolecules, 1998, pp. 648-654, vol. 21.

Schomburg, D., "Strong Distortion of the Tetrahedral Geometry in a Spirosilicate: Molecular Structure of Bis(tetramethylethylenedioxy)silane", Angew. Chem. Intl. Ed., 1983, p. 65, vol. 22, No. 1.

Moore, J.C., "Gel Permeation Chromatography. I. A New Method for Molecular Weight Distribution of High Polymers", Journal of Polymer Science Part A, 1964, pp. 835-843, vol. 2.

Mehrotra, R.C. et al., "Reactions of Tetramethoxy- & Triethoxysilanes with Glycols", Indian J. Chem., 1967, pp. 444-448, vol. 5.

Mehrotra, R.C. et al., "Organic Derivatives of Silicon. Part V. Reactions of Silicon Tetra-acetate with Glycols: Synthesis of Glycol Derivatives of Silicon", Indian Jour. Chem. Soc., pp. 563-566, vol. 41, No. 8.

Hahn, W., Chem. Abst. No. 49:8249, "Sprio silicates from silicon tetrachloride and diols", Makromolekulare Chemie, 1953, pp. 51-83, vol. 11.

Voronkov, M.G. et al., "Alkoxysilanes. XXIII. Spirocyclic esters of silicic acids", Chem. Abst. No. 70:68820.

Kuznetsova, V.P. et al., "Synthesis of hydroxysilanes and urethanes based on them", Chem. Abst. No. 71:39061.

Kopylov, V.M. et al., "Transesterification of tetraethoxysilane with difunctional alcohols in the presence of nucleophilic catalysts", Chem. Abst. No. 108:86867.

Dave, B.C., et al., "Sol-gel Encapsulation Methods for Biosensors", Analytical Chemistry, 1994, pp. 1120-1127A, vol. 66, No. 22.

Gill, I. et al., "Lipase—Silicone Biocomposite: Efficient and Versatile Immobilized Biocatalysts", Journal of the American Chemical Society, 1999, pp. 9487-9495, vol. 121, No. 41.

Zhang, Z. et al., "The Biporous Structure of Monolithic Silica Columns Containing Entrapped Proteins", Abstract, Submitted Aug. 2002 Conference, published Aug. 10, 2002.

Ishizuka, N. et al., "Performance of a Monolithic Silica Column in a Capillary Under Pressure-Driven and Electrodriven Conditions", Anal. Chem., 2000, pp. 1275-1280, vol. 72.

* cited by examiner i)

ii)

iii)

A

B

A                               B a b c

PROTEIN COMPATIBLE METHODS AND COMPOUNDS FOR CONTROLLING THE MORPHOLOGY AND SHRINKAGE OF SILICA DERIVED FROM POLYOL-MODIFIED SILANES

FIELD OF THE INVENTION

The present invention relates to methods of preparing biomolecule compatible siliceous materials, to the siliceous materials prepared using these methods and to uses of the siliceous materials, in particular as chromatographic supports, biosensors and/or to immobilize and stabilize proteins.

BACKGROUND OF THE INVENTION (a) Utilization of Silica as Chromatographic Support Silica in a variety of particulate forms has been extensively utilized as a chromatographic support. Partition of dissolved molecules between the hydrophilic siliceous surface and a flowing solvent permits the separation of compounds on many different scales (ng→kg scales). The efficiency of separation in these systems is related to the surface area of the silica to which the compound mixture is exposed.

The configuration of common separation systems utilizes a cylindrical bed of particulate silica in a glass, metal or polymeric cladding. A traditional approach to improving separation efficiency (theoretical plates) with such systems is to utilize longer columns of particulate silica of a given particle size (or range of sizes). Alternatively, higher separation efficiency is associated with the use of very small particles with larger surface areas.

There is an important physical limitation to practical separation with packed particulate systems. As the number of theoretical plates increases there is an attendant increase in backpressure on the column. There is, therefore, a trade off between higher separation efficiency and practical operating pressures. High pressures have attendant danger, and/or are impractical from the perspective of cost. Even with highly efficient columns operating at high pressures, the throughput that can be realized is often relatively low.[1]

Significant improvement in the surface area/back pressure relationship can be realized by the use of self-supporting monolithic silica columns.[1,2] For example, styrene monoliths have been reported to be useful for polynucleotide separation.[3] The group of Tanaka, in particular, have reported the preparation of silica monoliths.[4] Merck currently sells monolithic silica columns under the Chromolith" label.[5] The structure of these monoliths involves a series of distorted silica spheres fused by a layer of silica. The presence of macropores, between linked silica beads of a few microns diameter, can be clearly seen by micrographic analysis and may be more carefully established by other techniques. In addition to macropores, the silica beads typically possess a mesoporous structure (in the case of the Merck columns, a total porosity of 80% is claimed, which is made up of macro- and mesopores, the latter of which are on the order of 13 nm in diameter).[5]

(b) Problems with Existing Monolithic Silica

Silica produced by a sol-gel process is prone to shrinkage. Gelation is initiated in the presence of large quantities of solvent and, frequently, other dopants (see below). Evaporation of the solvent is accompanied by significant shrinkage forces: $Si(OEt)_4$-derived gels can shrink in air up to 85%.[6] This can be problematic in a number of ways when the resulting silica is used as a chromatographic support. First, in extreme conditions, the column can fracture leading to changes/degradation in separation performance. Second, the monolith can pull away from the cladding material, providing an alternative elution pathway for the compounds to be separated. This complicates, at best, the separation. In the worst instance, the eluting mixture will bypass most of the column surface area resulting in no separation.

Several strategies have been developed to reduce the problem of shrinking. For example, use of a drying agent in the original sol, such as DMF, helps in the silica annealing process.[7] The most common means to deal with shrinking is to accept that it will occur and to thermally cure the silica, essentially to completion. Hydrothermal treatment can be used to dissolve/re-precipitate the silica, which reduces the cracking that is frequently observed upon shrinking.[8,9] Dopants like urea in the sol have been reported to facilitate the dissolution/re-precipitation process.[10] An alternative strategy is to heat shrink the column cladding after shrinkage has occurred to reform an effective interface between monolith and cladding material. Finally, soluble polymers such as poly(ethylene oxide) may be added to the sol. These have the effect of increasing porosity of the monolith.[11]

The use of sol-gel techniques provides an exceptional degree of morphological control in the preparation of silica. Thus, total porosity, pore size and shape, regularity of pore distribution, etc., can be manipulated using a variety of starting materials, reaction conditions and dopants.[12] Many of these conditions, however, are incompatible with the incorporation of fragile compounds such as biomolecules, proteins in particular. Either the synthetic conditions are damaging to protein structure (e.g., pH conditions, the presence of denaturants such as ethanol) or the final curing conditions require elevated temperatures. It is of interest to incorporate such biomolecules into silica to create materials that serve as biosensors, immobilized enzymes or as affinity chromatography supports.

(c) Applications of Monolithic Silicas to Bioaffinity Chromatography

Bioaffinity chromatography has been used widely for sample purification and cleanup,13 chiral separations,[14] on-line proteolytic digestion of proteins,[15] development of supported biocatalysts,[16] and more recently for screening of compound libraries via the frontal affinity chromatography method.[17,18] In all cases, the predominant method used to prepare protein-loaded columns has been based on covalent or affinity coupling of proteins to silica beads. However, coupling of proteins to beads has several limitations, including; loss of activity upon coupling (due to poor control over protein orientation and conformation), low surface area, potentially high backpressure (which may alter $K_d$ values[19]), difficulty in loading of beads into narrow bore columns, difficulty in miniaturizing to very narrow columns (<50 μm i.d.), and poor versatility, particularly when membrane-bound proteins are used.[18]

In recent years it has been shown that a very mild and biocompatible sol-gel processing method can be used to entrap active proteins within a porous, inorganic silicate matrix.[20] In this method, a two-step processing method is used wherein a buffered solution containing the protein is added to the hydrolyzed silica sol to initiate gelation under conditions that are protein-compatible.[21] Numerous reports have appeared describing both fundamental aspects of entrapped proteins, such as their conformation,[22,23,24] dynamics,[25,26,27] accessibility,[24,28] reaction kinetics,[22,29] activity,[30] and stability,[31] and their many applications for catalysis and biosensing.[20,21] A number of reports also exist describing sol-gel based immunoaffinity columns,[32] and enzyme-based columns[33] although in all cases these were formed by crushing protein-doped silica monoliths and then loading the bioglass into a column as a slurry.

Very recent work on the development of protein-doped monolithic sol-gel columns has appeared from the groups headed by Zusman[34] and Toyo oka.[35] Zusman s group have developed columns using glass fibers covered with sol-gel glass as a new support for affinity chromatography. Toyo oka s group have used capillary electrochromatography (CEC) to both prepare protein-doped sol-gel based columns and to elute compounds. These monoliths were derived solely from TEOS or TMOS using a very high water:silicon ratio, resulting in a loosely packed monolith with large pores to allow flow of eluent. While this is a significant advance, all chromatography was done using electroosmotic flow (CEC), which separates compounds on the basis of a combination of charge, mass and affinity, and is less compatible with MS detection due to the necessarily high ionic strength of the eluent. Also, these authors did not examine the interaction of potential inhibitors with entrapped proteins on-column. This is a particularly important issue given the emergence of high throughput screening (HTS) methods based on immobilized enzymes.[17,18,36]

The present inventors have previously described the preparation of silica from a series of sugar alcohol, sugar acid or oligo- and polysaccharide-derived silanes. These starting materials offer a number of advantages over the more classically used tetraethoxy- and tetramethoxysilanes (TEOS and TMOS, respectively). Among these are mild conditions, including a greater control of pH used in the sol (ranges from 4-11.5 are possible), very low processing temperatures, process reproducibility, reduced shrinking and compatibility with the incorporation of a variety of dopants, particularly proteins. However, there remains a need to control the shrinkage of the resulting silica to avoid the evolution of cracks. Furthermore, morphological control needs to be available such that the materials can be tailored for specific applications including chromatography, biosensors, etc. Finally, an ability to improve the stability of the entrapped biomolecule is needed.

SUMMARY OF THE INVENTION

Siliceous materials have been prepared under mild conditions, the resulting materials showing reduced shrinkage and, under certain conditions, form a monolith having a bimodal meso/macroporous structure. Such materials are useful in chromatographic applications and are especially amenable to the entrainment of biomolecules.

Specific additives have been found by the present inventors to control the morphology and to reduce the shrinkage of siliceous materials obtained from the organic polyol modified silanes previously described in their co-pending patent application WO 03/102001.[6] For example, meso/macroporous monolithic silica material was obtained by combining a water soluble polymer (for example PEO and derivatives thereof) with polyol-derived silica precursors under conditions where a phase transition, or spinodal decomposition, occurred before the material gelled. The phase transition was marked by an increase in turbidity of the precursor/polymer solution. Further, certain trifunctional silanes, including water soluble polymers chemically modified to contain trifunctional silanes, provided silica having a dramatic reduction in shrinkage properties. These trifunctional silanes were also shown to enhance the stability of the protein entrapped within the silica network when used in combination with organic polyol silane precursors. In particular, Src kinase, luciferase, Factor Xa and urease, which are far less stable in conventional sol gel materials derived from tetraalkoxysilanes or polyolsilanes, have been entrapped and the activity of these enzymes was preserved over multiple uses. Water soluble polymers chemically modified to contain trifunctional silanes also provided bimodal meso/macroporous monolithic silica materials.

Accordingly, the present invention includes a method of preparing siliceous materials comprising combining an organic polyol silane precursor with one or more additives under conditions suitable for hydrolysis and condensation of the precursor to a siliceous material, wherein the one or more additives are selected from one or more water-soluble polymers and one or more trifunctional silanes of Formula I:

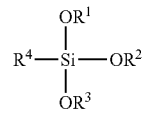

wherein $R^1$, $R^2$ and $R^3$ are the same or different and represent a group that may be hydrolyzed under normal sol-gel conditions to provide Si—OH groups; and $R^4$ is a group that is not hydrolyzed under normal sol-gel conditions.

The present invention further relates to a method of preparing siliceous materials with enhanced protein stabilizing ability comprising combining an organic polyol silane precursor with one or more additives under conditions suitable for hydrolysis and condensation of the precursor to a siliceous material, wherein the one or more additives are selected from one or more trifunctional silanes of Formula I:

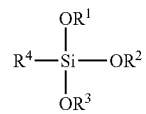

wherein $R^1$, $R^2$ and $R^3$ are the same or different and represent a group that may be hydrolyzed under normal sol-gel conditions to provide a Si—OH group and $R^4$ is polyol-(linker)-.

The invention also includes the siliceous materials prepared using the methods of the invention as well as the use of these materials, for example, but not limited to, in chromatographic applications (particularly with macroporous materials), as bioaffinity supports, biosensors and/or for immobilizing enzymes, in particular, the trifunctional silanes of Formula I, where $R^4$ contains a polyol moiety, have protein stabilizing activity. Further, the present invention extends to analytical and other types of hardware (for example chromatographic columns, microarrays, bioaffinity columns, sample cleanup devices such as in-tube solid phase microextraction media, SPME films, ziptips, etc.) comprising the materials prepared using the methods of the invention.

The mild conditions under which the siliceous materials are prepared using the methods of the present invention are compatible with proteins and other biomolecules. This allows for these types of molecules to be readily incorporated into these siliceous materials for a wide variety of applications. Also, the shrinkage of the materials prepared using the methods of the present invention is significantly reduced when compared to TEOS- or TMOS-derived materials (as well as polyol-silane derived materials which were prepared under conditions previously reported[6]), which again, provides a more stable environment for entrained biomolecules.

The present inventors have also developed biomolecule compatible, bimodal meso/macroporous silica materials using the method of the present invention. It has been shown that these materials can be used for protein entrapment and that capillary columns based on these materials can be prepared that are suitable for pressure driven liquid chromatography and compatible with MS detection.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

Figure 1:
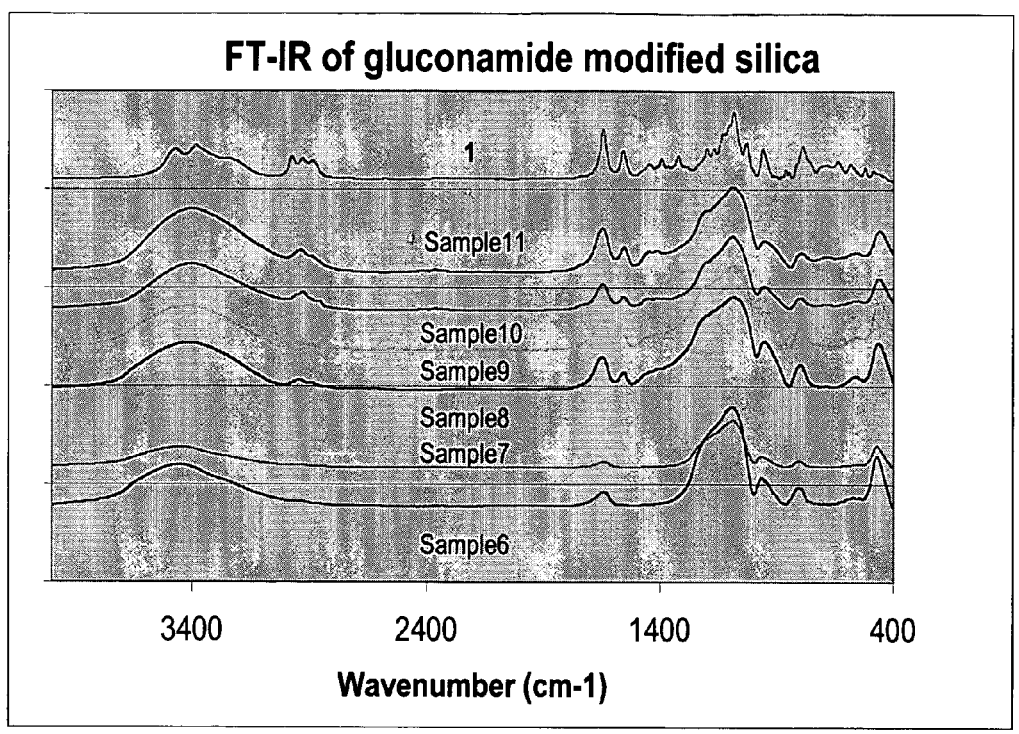
FIG. 1 shows the FT-IR spectra of gluconamide-modified, DGS-derived silica.

DETAILED DESCRIPTION OF THE INVENTION (i) Methods of the Invention

The present inventors have developed methods to control the morphology, shrinkage and protein stabilization characteristics of siliceous materials derived from organic polyol modified silanes. Specifically, it has been found that the addition of higher molecular weight PEO, or other water soluble polymers, to organic polyol-based sols under conditions where a phase transition, or spinodal decomposition, occurs before gelation, leads to meso/macroporous monolithic silica material. Further, it has been found that the addition of trifunctional silanes conjugated through an alkyl amide linkage to sugar lactones (including gluconamide, maltonamide and dextronamide), to organic polyol-based tetrafunctional silanes, including as representative, non-limiting examples, diglycerylsilane (DGS) and monosorbitylsilane (MSS), provides siliceous materials having a dramatic reduction in shrinkage properties as well as dramatic protein stabilization capabilities. Similarly, PEO modified with a trifunctional silane through a propyl ether linkage led to a reduction in silica shrinkage. Accordingly, a route to siliceous materials that have reduced shrinkage compared to TEOS-derived gels, which are readily formed over a wide range of pHs, which may be prepared at ambient or slightly higher (e.g., 37° C.) temperatures, without the necessity for heat curing or air drying, and which have enhanced protein stabilization characteristics, has been developed. As a result, it is possible to dope these siliceous materials with a variety of species, in particular biomolecules such as proteins.

Accordingly, the present invention relates to a method of preparing siliceous materials comprising combining an organic polyol silane precursor with one or more additives under conditions suitable for hydrolysis and condensation of the precursor to a siliceous material, wherein the one or more additives are selected from one or more water-soluble polymers and one or more trifunctional silanes of Formula I:

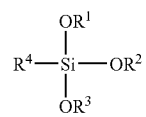

wherein $R^1$, $R^2$ and $R^3$ are the same or different and represent a group that may be hydrolyzed under normal sol-gel conditions to provide Si—OH groups; and $R^4$ is group that is not hydrolyzed under normal sol-gel conditions.

The water soluble polymer may be selected from any such compound and includes, but is not limited to, one or more of: polyethers, for example, polyethylene oxide (PEO); polyethylene glycol (PEG); amino-terminated polyethylene glycol (PEG-NH$_2$); polypropylene glycol (PPG); polypropylene oxide (PPO); polypropylene glycol bis(2-amino-propyl ether) (PPG-NH$_2$); polyalcohols, for example, polyvinyl alcohol; polysaccharides; poly(vinyl pyridine); polyacids, for example, poly(acrylic acid); polyacrylamides e.g. poly (N-isopropylacrylamide); (polyNIPAM); and polyallylamine (PAM). In an embodiment of the invention, the water soluble polymer is selected from one or more of PEO, PEO-NH$_2$, PEG, PPG-NH$_2$, polyNIPAM and PAM. In further embodiments of the invention, the water soluble polymer is selected from one or more of PEO, PEO-NH$_2$ and polyNIPAM. By water soluble it is meant that the polymer is capable of being formed into an aqueous solution having a suitable concentration. It should be noted that the terms oxide (as in polyethylene oxide) and glycol (as in polyethylene glycol) may be used interchangeably and the use of one term over the other is not meant to be limiting in any way.

In embodiments of the invention, OR$^1$, OR$^2$ and/or OR$^3$ are the same or different and are derived from organic mono-, di-, or polyols. By polyol, it is meant that the compound has more the one alcohol group. The organic portion of the polyol may have any suitable structure ranging from straight and branched chain alkyl and alkenyl groups, to cyclic and aromatic groups. For the preparation of biomolecule compatible silicas, it is desired that the organic polyol to be biomolecule compatible. In an embodiment of the invention, the groups OR$^1$, OR$^2$ and/or OR$^3$ are derived from sugar alcohols, sugar acids, saccharides, oligosaccharides or polysaccharides. Simple saccharides are also known as carbohydrates or sugars. Carbohydrates may be defined as polyhydroxy aldehydes or ketones or substances that hydrolyse to yield such compounds. The polyol may be a monosaccharide, the simplest of the sugars or carbohydrate. The monosaccharide may be any aldo- or keto-triose, pentose, hexose or heptose, in either the open-chained or cyclic form. Examples of monosaccharides that may be used in the present invention include, but are not limited to allose, altrose, glucose, mannose, gulose, idose, galactose, talose, ribose, arabinose, xylose, lyxose, threose, erythrose, glyceraldehydes, sorbose, fructose, dextrose, levulose or sorbitol. The polyol may also be a disaccharide, for example, but not limited to sucrose, maltose, trehalose, cellobiose or lactose. Polyols also include polysaccharides, for example, but not limited to dextran, (500-50,000 MW), amylose and pectin. Other organic polyols that may be used include, but are not limited to glycerol, propylene glycol or trimethylene glycol. In embodiments of the present invention, the group $OR^1$, $OR^2$ and/or $OR^3$ are derived from a polyol selected from glycerol, sorbitol, maltose, trehalose, glucose, sucrose, amylose, pectin, lactose, fructose, dextrose and dextran and the like. In further embodiments of the present invention, the organic polyol is selected from glycerol, sorbitol, maltose and dextran.

In other embodiments of the invention, $OR^1$, $OR^2$ and $OR^3$ are the same and are selected from $C_{1-4}$alkoxy, for example, methoxy or ethoxy, aryloxy and arylalkyleneoxy. In further embodiments of the invention, $OR^1$, $OR^2$ and $OR^3$ are all ethoxy. It will be apparent to those skilled in the art that other leaving groups such as chloride or silazane may also be used for the formation of silica according to the methods described in the invention.

The term aryloxy as used herein means phenoxy or naphthyloxy wherein, the phenyl and naphthyl groups may be optionally substituted with 1-5 groups, specifically 1-3 groups, independently selected from the group consisting of halo (fluoro, bromo, chloro or iodo), $C_{1-6}$alkyl, $C_{1-6}$alkoxy, OH, $NH_2$, $N(C_{1-6}alkyl)_2$, $NHC_{1-6}$alkyl, $C(O)C_{1-6}$alkyl. $C(O)NH_2$, $C(O)NHC_{1-6}$alkyl, $OC(O)C_{1-6}$alkyl, $OC(O)OC_{1-6}$alkyl, $NHC(O)NHC_{1-6}$alkyl, phenyl and the like.

The term arylalkyleneoxy as used herein means aryl-$(C_{1-4})$-oxy wherein aryl has the same meaning as in aryloxy. Specifically, arylalkyleneoxy is a benzyloxy or naphthylmethyloxy group (i.e. aryl-$CH_2$—O).

It should be noted that the groups $OR^1$, $OR^2$ and $OR^3$ are capable of participating directly in the hydrolysis/polycondensation reaction. In particular, these functional groups are alkoxy groups attached to the silicon atom at oxygen, i.e., Si—OR, which may be hydrolyzed to provide Si—O—H, which can condense with other Si—O—H or Si—OR groups to provide Si—O—Si linkages and eventually a three-dimensional network within a gel. Trifunctional silanes form silsesquioxanes upon hydrolysis and there is a lower degree of crosslinking in systems derived therefrom, in particular when compared with systems derived from tetrafunctional silanes. The remaining group attached to the silicon atom ($R^4$) is a group that generally does not participate directly in the hydrolysis/polycondensation reaction.

$R^4$ is a group that is not hydrolyzed under normal sol-gel conditions and preferably is stabilizing to biological substances, in particular proteins. In specific embodiments, $R^4$ is selected from one of the following groups:

polyol-(linker)-;

polymer-(linker)$_n$-; and

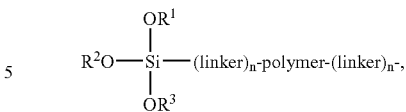

wherein n is 0-1 and $OR^1$, $OR^2$ and $OR^3$ are as defined above. The term polyol in $R^4$ has the same definition as described above for the groups $OR^1$, $OR^2$ and $OR^3$. In an embodiment of the invention, the polyol is derived from glucose or maltose. The term polymer in $R^4$ refers to any water soluble polymer, such as, but not limited to: polyethers, for example, polyethylene oxide (PEO); amino-terminated polyethylene oxide (PEO-$NH_2$); polyethylene glycol (PEG); polyethylene glycol bis(2-amino-propyl ether) (PEG-$NH_2$); polypropylene glycol (PPG); polypropylene oxide (PPO); polypropylene glycol bis(2-amino-propyl ether) (PPG-$NH_2$); polyalcohols, for example, polyvinyl alcohol; polysaccharides; poly(vinyl pyridine); polyacids, for example, poly(acrylic acid); polyacrylamides e.g. poly(N-isopropylacrylamide) (polyNIPAM); or polyallylamine (PAM). A linker group is required (i.e. n=1) when a direct bond between the silicon atom and the polymer would be hydrolyzed under normal sol-gel conditions. In embodiments of the invention, the polymer is a water soluble polyether such as PEO.

The sugar and polymer residues may be attached to the silicon atom through any number of linkers. Such linkers may be based on, for example, alkylene groups (i.e. —$(CH_2)_m$—, m=1-20, specifically 1-10, more specifically 1-4), alkenylene groups (i.e. —$(CH═CH)_m$, m=1-20, specifically 1-10, more specifically 1-4), organic ethers, thioethers, amines, esters, amides, urethanes, carbonates or ureas. A person skilled in the art would appreciate that they are numerable linkers that could be used to connect the group, $R^4$, to the silicon atom.

By biomolecule compatible it is meant that a substance either stabilizes proteins and/or other biomolecules against denaturation or does not facilitate their denaturation.

The terms biomolecule or biological substance as used herein, are interchangeable and means any of a wide variety of proteins, enzymes and other sensitive biopolymers including DNA and RNA, and complex systems including whole plant, animal and microbial cells that may be entrapped in silica. The biomolecule may be dissolved in a suitable solvent, for example an aqueous buffer solution, such as TRIS buffer. In an embodiment of the invention, the biological substance is in its active form.

By normal sol gel conditions it is meant the conditions used herein to effect hydrolysis and condensation of the organic polyol derived silanes. This includes, in aqueous solution, at a pH in the range of 1-13, specifically in the range 4-11.5, and temperatures in the range of 0-80° C., and specifically in the range 0-40° C., and optionally with sonication and/or in the presence of catalysts known to those skilled in the art of room temperature vulcanization, including acids, amines, dialkyltin esters, titanates, etc.

The terms a and an as used herein can mean one or more than one.

Illustrative of compounds of Formula I of the present invention, are two classes of the trifunctional silanes based on saccharides which were prepared as described herein below: monosaccharide-(compound 1) and disaccharide-(compounds 2 and 3) based trifunctional silanes are shown in Schemes 1 and 2. Hydrolysis and condensation of these species along with organic modified silanes (for example diglycerylsilane) allows the incorporation of these species into sol gel derived siliceous materials resulting in materials that have non-hydrolyzable sugar moieties covalently bound into the silica network. Such materials permanently incorporate protein stabilizing agents into the silica and retain water in the silica matrix, avoiding denaturation of the entrapped protein. Also prepared were polymeric bis(trifunctional silanes) 5 (see Scheme 3).

Although in both of the saccharide examples shown in Schemes 1 and 2, many different opportunities for modification with silanes exist, it was chosen to modify the anomeric hemiacetal centre at the terminus of the saccharidic chains. Oxidation of any of the sugars converts the anomeric hemiacetal into the lactone (Scheme 1). This could then be opened by an amino-modified alkoxysilane to produce a sugar-modified coupling agent.[37] The key functional group tethering the two groups in this case is an alkylamide. Examples of such sugar modified silanes prepared herein are shown in Scheme 2.

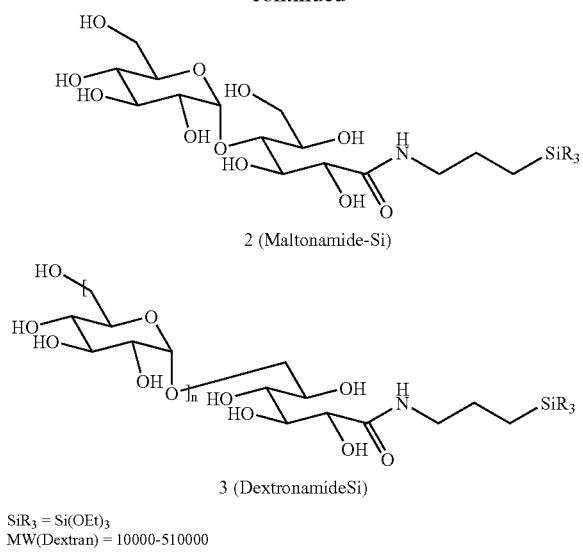

2 (Maltonamide-Si)

3 (DextronamideSi)

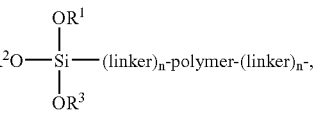
$SiR_3 = Si(OEt)_3$
MW(Dextran) = 10000-510000

Illustrative of compounds of Formula I wherein $R^4$ is $$R^2O-\underset{\underset{OR^3}{|}}{\overset{\overset{OR^1}{|}}{Si}}-(linker)_n\text{-polymer-}(linker)_n\text{-},$$

wherein $OR^1$, $OR^2$ and $OR^3$ are as defined above, are compounds 5 shown in Scheme 3. Compounds 5 can be prepared, for example, by reacting poly(ethylene oxide), first with allyl bromide (or any other suitable allylating reagent), followed by reaction with a trialkoxy-, triarylalkyleneoxy- or triaryloxysilane, in the presence of a catalyst, such as a platinum-derived catalyst, as shown in Scheme 3. When modified PEO polymers are used, for example the compound of Formula 5, it is preferred that the starting PEO have a MW of greater than about 2000 g/mol. In this example the linker is an alkylene group, with m=3. Note some allyl-terminated PEO polymers 4 are commercially available. It would be apparent to one skilled in the art that other levels of functionality can also be used to bind these species to the siliceous matrix, such as: $R_{3-k}J_kSi$-linker-polymer-linker-$SiJ_kR_{3-k}$ and polymer-linker-$SiJ_kR_{3-k}$ where k=1-3 and J is a group that can participate in hydrolysis and condensation with the silica network.

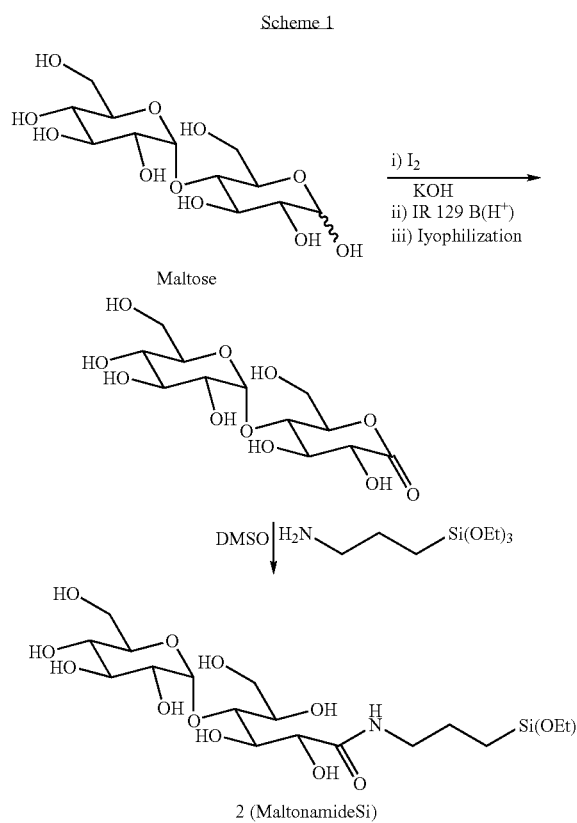

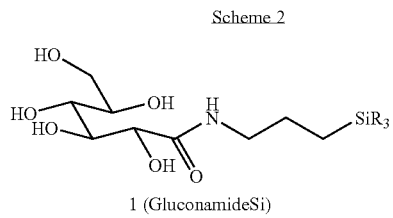

1 (GluconamideSi)

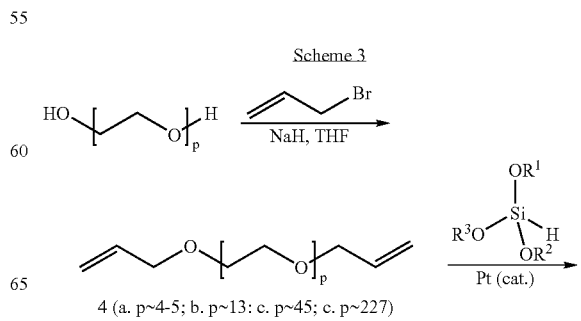

4 (a. p~4-5; b. p~13; c. p~45; c. p~227)

-continued

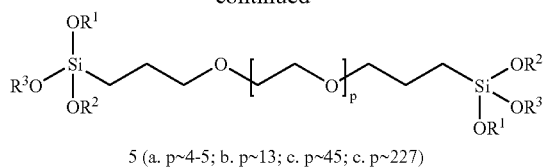

5 (a. p~4-5; b. p~13; c. p~45; c. p~227)

As stated above, the organic polyol derived silane precursors have been described in the inventors co-pending patent application (PCT patent application No. WO 03/102001)[6], the contents of which are incorporated herein by reference. The term polyol once again has the same definitions as described above. Although a wide variety of ratios of sugar/silicon are readily prepared (e.g., monosorbitylsilane (MSS), disorbitylsilane, trisorbitylsilane), as will be appreciated by one skilled in the art, the cure behavior of such compounds differs widely. The resulting polyol modified silanes listed below are particularly convenient for the method of the invention: diglycerylsilane (DGS), monosorbitylsilane (MSS), monomaltosylsilane (MMS), dimaltosylsilane (DMS) or dextran-based silane (DS). More particularly, diglycerylsilane (DGS) or monosorbitylsilane (MSS) are used in the method of the invention. One of skill in the art can readily appreciate that other molecules including simple saccharides, oligosaccharides, and related hydroxylated compounds can also lead to viable silica precursors. Higher molecular weight polyols and polysaccharides, e.g., dextran and the like, do not completely leach from the silica, once formed.

The preparation of silica from sugar-modified silanes such as glycerol (DGS—diglycerylsilane; or MSS—monosorbitylsilane) has been previously reported.[6] In those cases, all silicon atoms contained in the resulting gel were tetrafunctional, Q-type[38] (four bonds to oxygen, $Si(OR)_4$). Co-hydrolysis of any of the water soluble polymers or compounds of Formula I with DGS or MSS led to silica possessing very different properties.

The hydrolysis and polycondensation of the organic polyol derived silanes in the presence of one or more additives typically occurred upon standing of the reagents in aqueous solution or with sonication to assist in dissolution. In embodiments of the invention, the additives are added as solutions in suitable buffers. The aqueous solution may be adjusted to a pH in the range of 4-11.5 (and may be tailored to the biomolecule, if any is to be entrained in the matrix), using a buffer, for example TRIS buffer, to initiate hydrolysis and condensation. In an embodiment of the invention, the pH is adjusted so that it is in a range of about 4-10. The resulting solution will eventually gel (lose the ability to flow) and the material may be allowed to cure or age for sufficient period of time. A person skilled in the art can determine this time depending on the desired application for the siliceous material. The term cure or age means the continued evolution of the silica matrix upon aging of the silica following gelation. Once the material is sufficiently cured, it may be dried before use. The material may be molded into any desired shape, for example, films, spots, fibres, monoliths, pellets, granules, tablets, rods and bulk, as the solution becomes viscous but before it becomes completely gelled.

It has been found that when the additive is a trifunctional compound of Formula I, siliceous materials having reduced shrinkage are produced. Accordingly, in embodiments of the invention, there is provided a method of preparing siliceous materials with low shrinkage characteristics comprising:
    (a) combining an aqueous solution of one or more compounds of Formula I with an aqueous solution of an organic polyol silane precursor
    (b) adjusting the pH of the solution in (a) to about 4-11.5;
    (c) allowing the solution of (b) to gel;
    (d) aging the gel of (c); and
    (e) partially drying the aged gel in air.

In further embodiments, the compound of Formula I is selected from those wherein $R^4$ is selected from one of the following groups:
    polyol-(linker)-; and

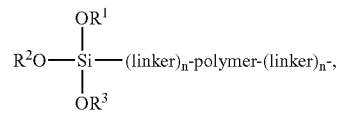

wherein n is 0-1 and $OR^1$, $OR^2$ and $OR^3$ are as defined above.

Figure 2:
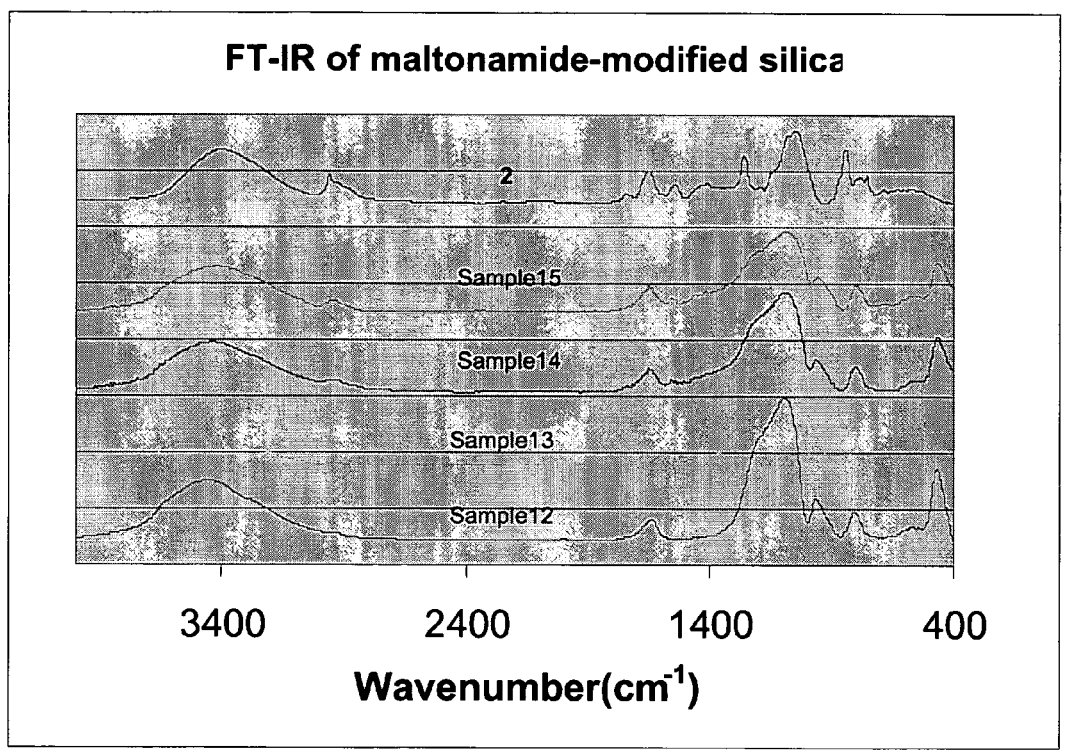
FIG. 2 shows FT-IR spectra of malonamide-modified, DGS-derived silica
Figure 3:
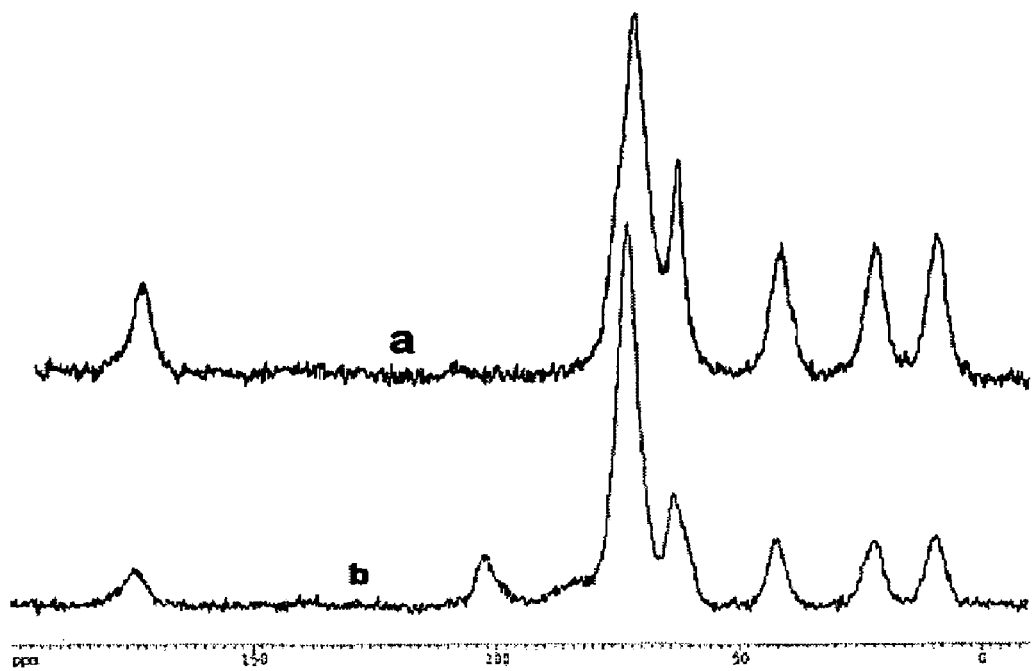
FIG. 3 shows solid-state $^{13}$C CPMAS NMR spectra of (a) sample 8, (b) sample 15.
Figure 4:
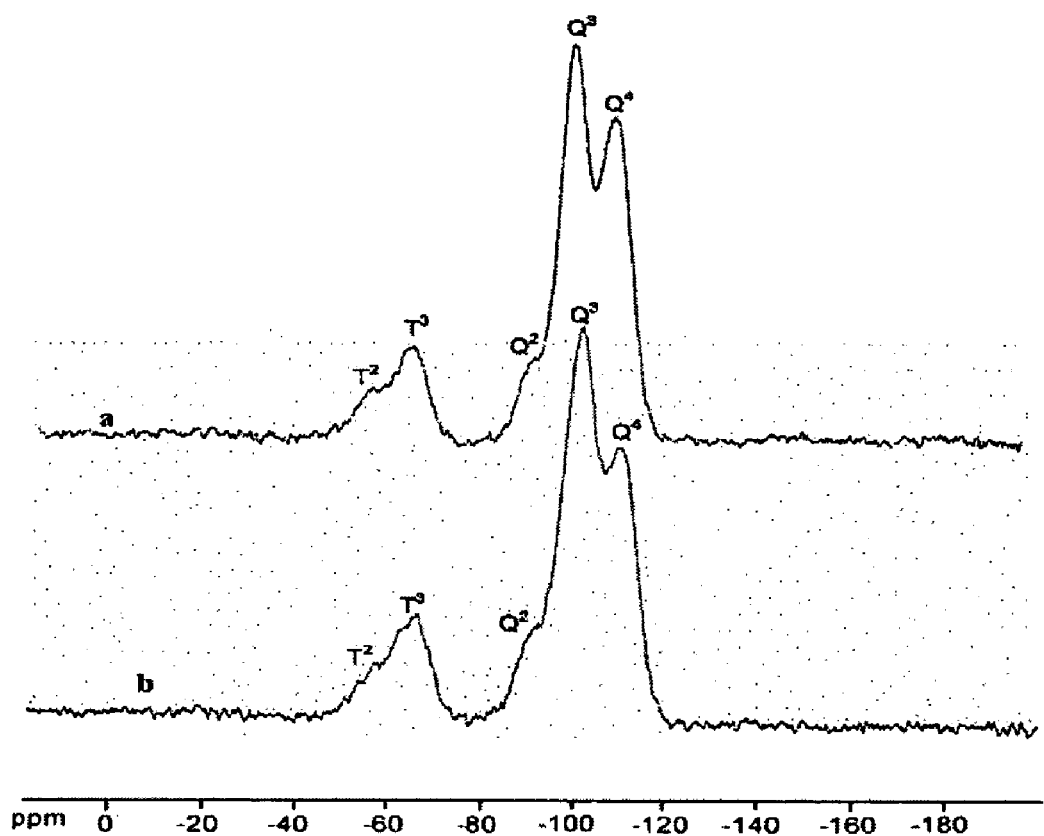
FIG. 4 shows solid-state $^{29}$Si CPMAS NMR spectra: (a) sample 8, (b) sample 15.

A series of compounds derived from DGS combined with gluconamide-Si(OEt)$_3$ 1, maltonamide-Si(OEt)$_3$, 2 or PEO-[Si(OEt)$_3$]$_2$, 5 respectively, were prepared. Gelation times for the composites depended upon the ratio of starting materials. In particular, there was a trend to slower curing (gelling) with an increase in the proportion of the additive (Table 1). These materials could be characterized by standard spectroscopic techniques including IR and NMR (See FIGS. 1-4 and Table 2). The former, in particular, is diagnostic because of the amide linkages that appear in the region between 1650 and 1700 cm$^{-1}$ (FIGS. 1-2).

The physical behavior of the siliceous materials prepared by combining a organic polyol silane precursor with a compound of Formula I was also studied. As stated above, the most significant impact on the behavior of the resulting products can be seen in the degree of shrinkage. Normally, when allowed to rest in the open environment (i.e., not under water), shrinkage of DGS gels occurs to a level of up to approximately 66% (see sample 6, FIG. 5), much less than TEOS-derived gels which shrink approximately 85%. By contrast, incorporation of the sugar-modified trifunctional silanes dramatically reduced shrinkage over the same time period (45 days) to less than 15% (samples 8-11, 13-15, FIG. 5). Reduced shrinkage was also observed when DGS was hydrolyzed and condensed in the presence of compounds 5. Mobility measurements were undertaken in order to assess the degree to which the trifunctional silanes modified the behaviors of the resulting siliceous surfaces. These results are shown in Table, FIG. 6. In all cases, the surfaces remain anionic.

The hydrolysis of DGS or MSS (and related compounds) leads to silica networks contaminated with polyol. These networks shrink far less than silica prepared from TEOS and are also more protein compatible as no denaturant is present during gel formation. In addition, the pH used for the gel synthesis can be adapted to the specific protein to be entrapped since, as stated above, gel formation conveniently occurs without supplemental catalysis over a pH range of 4-11.5. The addition of trifunctional compounds based on sugar lactones or polymers significantly changed the behavior of the resulting cure process, and most significantly decreased shrinkage in the final material and increased the protein stabilization properties.

The present invention also includes siliceous materials prepared using the method of the invention. Accordingly, the invention relates to siliceous materials having reduced shrinkage properties. By reduced shrinkage properties it is meant that the siliceous material shrinks in the range of about 5-15% (v/v) over a period of 45 days at in air room temperature.

In other aspects of the present invention, meso/macroporous silica monoliths were formed when the organic polyol silane precursors were combined with one or more water soluble polymers and/or compounds of Formula I, wherein $R^4$ is group selected from polymer-(linker)$_n$- and

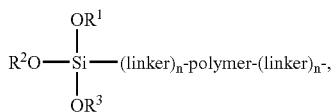

under conditions where the resulting sol undergoes a phase transition before gelation.

Accordingly, the present invention includes a method of preparing monolithic silica materials comprising combining an organic polyol silane precursor with one or more additives selected from one or more water-soluble polymers and one or more compounds of Formula I:

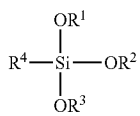 I wherein $R^4$ selected from the group consisting of polymer-(linker)$_n$- and

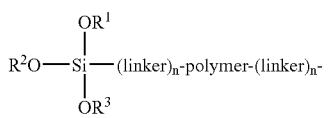

and n is 0-1, under conditions where a phase transition occurs before gelation.

In embodiments of the invention $R^4$ is

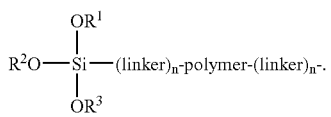

In further embodiments of the invention, the linker group is a $C_{1-4}$alkylene group and n is 1. The selections for $OR^1$, $OR^2$ and $OR^3$ are the same as those defined above.

The present invention also extends to the novel meso/macroporous silica monoliths prepared using the method of the invention. The invention therefore relates to a silica monolith with improved shrinkage characteristics, that is compatible with biomolecules and which is prepared at ambient temperature.

Figure 7:
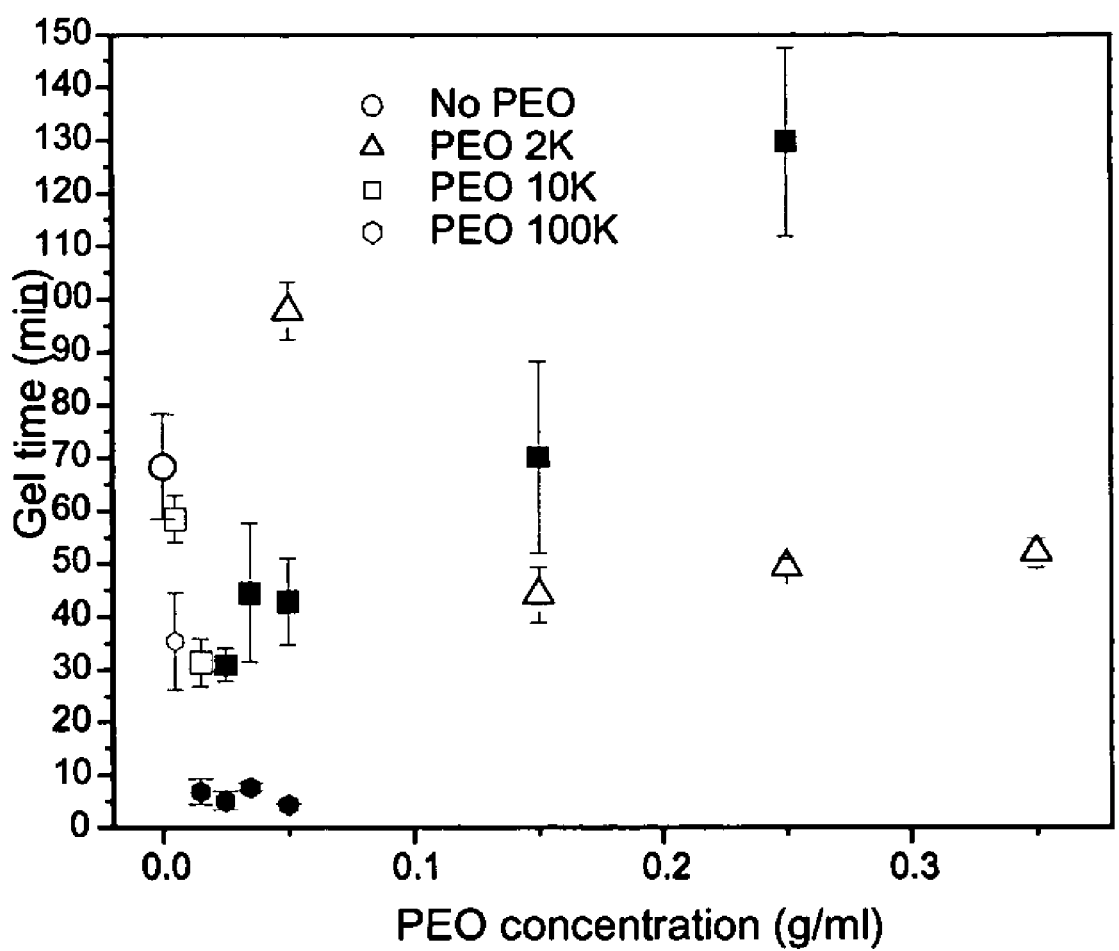
FIG. 7 is a graph showing the gel time of DGS doped with different molecular weight and different concentration of PEO solution. The open legend means transparent gel at gel time, and the closed legend means phase separation before gelation.

The conditions where a phase transition occurs before gelation may vary depending mainly on the identity of the water-soluble polymer (Table 4). When the water-soluble polymer is PEO, the timing of the gelation was dependent on both the PEO concentration and molecular weight (FIG. 7). In order for phase transition to occur before gelation, it is desirable that the non-functionalized PEO be of relatively high molecular weight (MW), for example greater than about 5000, specifically greater than about 7500, more specifically greater than about 10,000 g/mol, most specifically greater than about 100,000 g/mol, and at relatively high concentration, for example greater than about 0.005 g/mL of final solution, specifically greater than about 0.025 g/mL of final solution. Macroporous silica monoliths were also formed when poly(N-isopropylacrylamide) (polyNIPAM) was used as the water soluble polymer. The molecular weight of the polyNIPAM may be greater than about 5000, specifically greater than about 7500, more specifically greater than about 10,000 g/mol, most specifically greater than about 100,000 g/mol, and its concentration, may be greater than about 0.005 g/mL of final solution, specifically greater than about 0.025 g/mL of final solution. For amino-modified PEO (PEO-NH$_2$) the molecular weight may be greater than about 1000 g/mol, specifically greater than about 2000 g/mol, more specifically greater than about 3000 g/mol and its concentration, may be greater than about 0.005 g/mL of final solution, specifically greater than about 0.025 g/mL of final solution.

The effect of different functional groups on the water soluble polymer on cure characteristics was pronounced. Non-functional PEO of 10,000 MW was optimal for phase separation to occur before gelation. By contrast, poly(ethylene oxide) bearing terminal amino groups (PEO-NH$_2$) could form macroporous structures with molecular weights of only 3400, and PEO terminated with O(CH$_2$)$_3$Si(OEt)$_3$ groups (PEO-TES$_2$) could form macroporous structure with molecular weights of greater than about 200.

Macroporous silica monoliths could also be prepared by using a mixture of water soluble polymers. In this case, the morphology of the resulting silica was affected by the concentration, molecular weights, and character of the polymers. For example, addition of various amounts of PPG-NH$_2$ to a DGS-PEO sol led to silicas of very different morphology (see FIG. 8; the base recipe consists of 0.2 g DGS/200 μL H$_2$O+60 μL of 0.5 g/ml PEO 10,000 MW, to which was added a PPG-NH$_2$ solution comprised of PPG-NH$_2$ 200 MW 0.5 g/mL such that the final PEO/PPG-NH$_2$ ratios were i) 1000/1 ii) 1000/5, and iii) 1000/10).

A person skilled in the art can readily determine when a phase transition has occurred, for example, by observing the evolution of turbidity in the sol. As used herein, the time when the solution became totally opaque was recorded as the phase separation time ($t_{ps}$) and the time with the opaque phase lost its ability to flow was recorded as the gel time ($t_{gel}$).

Figure 9:
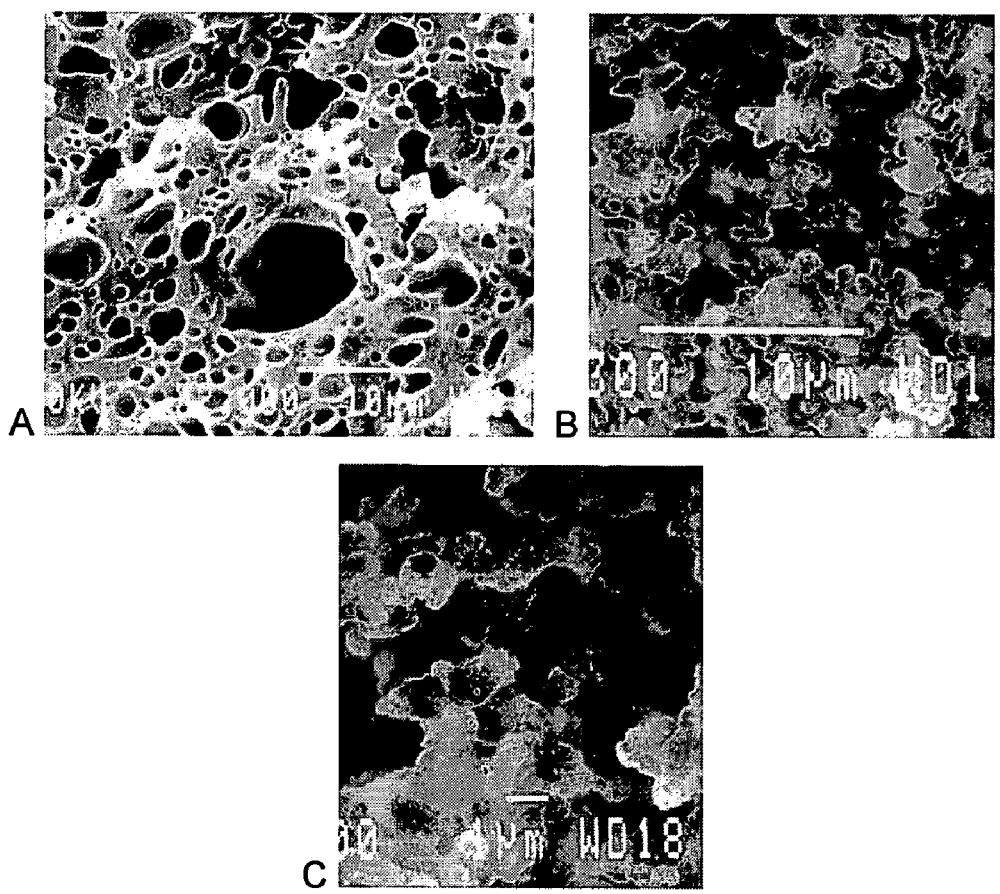
FIG. 9 shows electron micrographs of silica derived from DGS/PEO A: where the phase separation was not allowed to go to completion; B: after complete phase separation and gelation; C: Close-up of B.

The silica formed as a result of gelation after phase separation consists of small asymmetric beads fused together to create an open structure. The way in which the open structure evolves could be seen by washing unreacted starting material or low molecular weight oligomers from the gel prior to complete reaction of the alkoxysilane. The evolution of the gel can be seen in FIG. 9. The size of the aggregates is a function of the specific recipe used, and in particular depends on the molecular weight and type and weight percent of additive incorporated.

The aggregated silica beads that comprise the monolith are mesoporous in nature. This is clearly seen from the nitrogen absorption data (Table 5) which shows average pore sizes of 3.3 nm.

Figure 10:
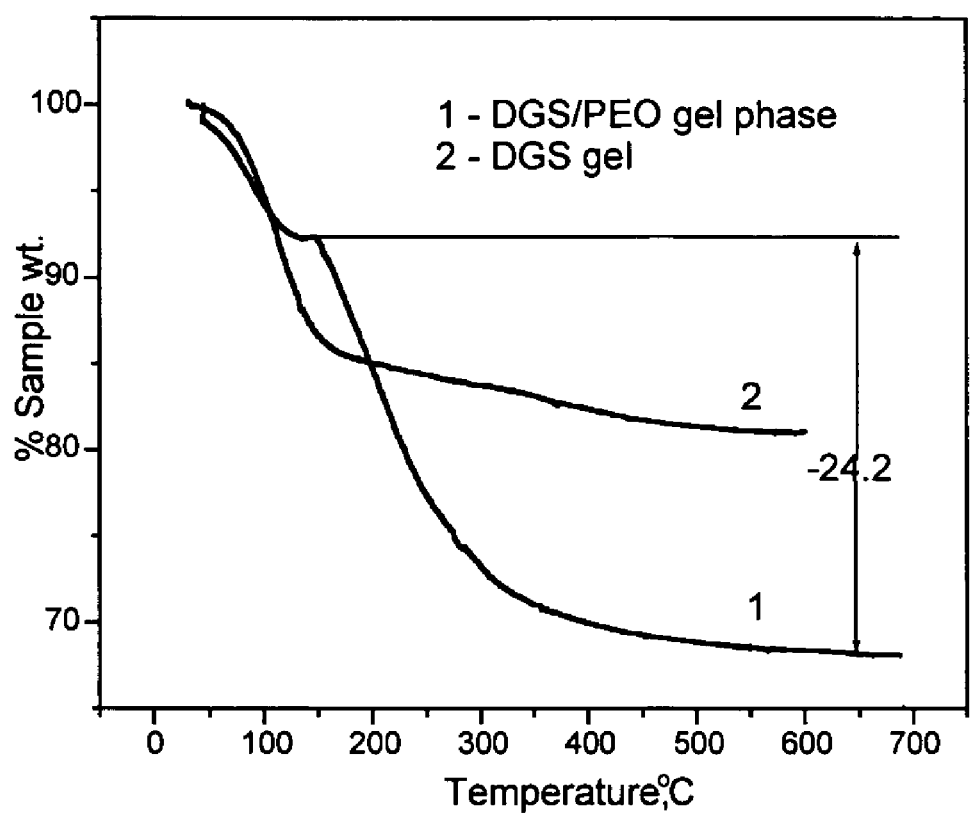
FIG. 10 shows TGA of silica monoliths, after washing and freeze drying, derived from 1: DGS, and 2: DGS/PEO (from 0.5 g DGS/500 μL H$_2$O/500 μL of 0.05 g/ml PEO 100,000 MW solution)

The silica macroporous monoliths formed using the method of the invention contain significant quantities of the organic polymer used to cause phase separation. Thermogravimetric analysis (TGA) showed that significantly greater quantities of organic material were found in the gels formed from DGS and doped with polymers than those which contained DGS and water in the absence of dopants (FIG. 10). Additional weight losses on heating due to evaporation of water, on the order of 10-15%, were observed in gels doped with polymer.

Further characterization of the nature of the sol-gel monoliths prepared using the method of the invention was available from calorimetry. Differential scanning calorimetry (DSC) of the gel resulting from reaction of DGS, water and PEO shows features associated with the glycerol (from DGS) but not with the polymeric dopant. Thus, an unwashed sample of silica derived only from DGS shows loss of glycerol above 200° C. (FIG. 1A). By contrast, the washed sample shows no glycerol in the first heating cycle and no significant thermal events in the second heating cycle. The melting point of pure PEO (MW 100,000) is 67° C. as seen in FIG. 11B. In the silica prepared from DGS and PEO, DSC shows no evidence of entrained domains of PEO or glycerol in the gel after crushing, washing and drying the gel. The peak in curve 2 corresponds to loss of some water (FIG. 11B). However, there is approximately 24% PEO remaining in the gel after washing (FIG. 10). Thus, the data from these gels is consistent with a silica structure containing dispersed PEO as can be seen from Table 6.

Use of polymers other than PEO can result in a different morphology in the resulting monolithic silica. These differences are readily visible in electron micrographs. A comparison of the silica prepared with PEO (FIG. 9B) with that prepared in the presence of polyNIPAM (FIG. 12A) shows very different aggregation behavior. The addition to DGS of PEO, PPG-NH$_2$ and compounds of Formula I, wherein R$^4$ is polymer-(linker)$_n$- or

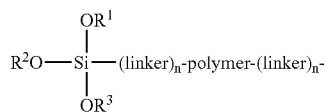

Figure 8:
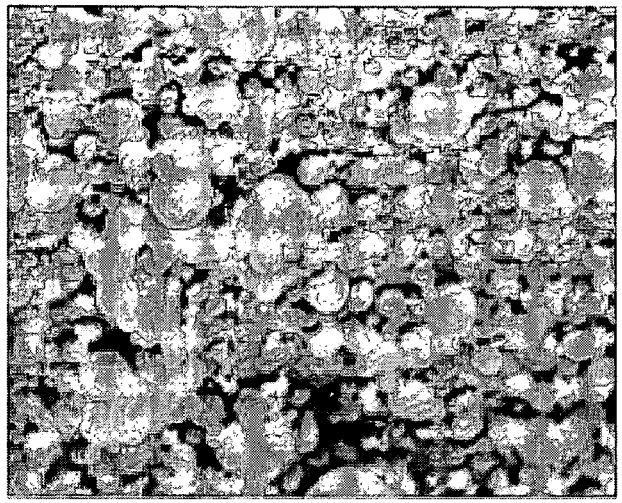
FIG. 8 shows electron micrographs of silica prepared from DGS using both PPG-NH$_2$ and PEO as dopants showing the change in morphology as the quantity of PPG-NH$_2$ was increased; i) PEO/PPG-NH$_2$=1000/1 ii) (b) PEO/PPG-NH$_2$=1000/5 and (iii) PEO/PPG-NH$_2$=1000/10.
Figure 8:
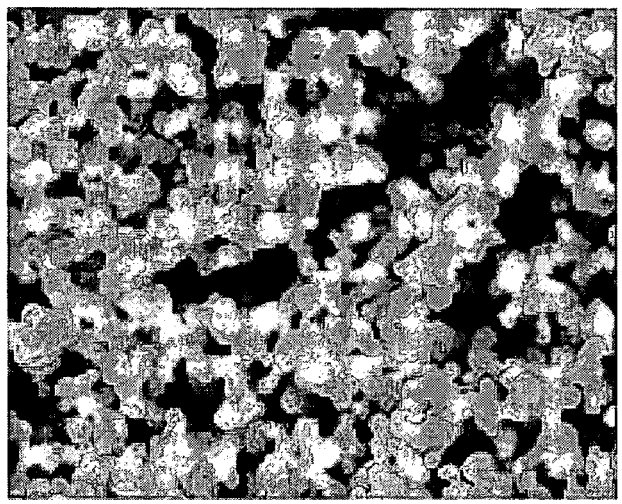
Figure 8:
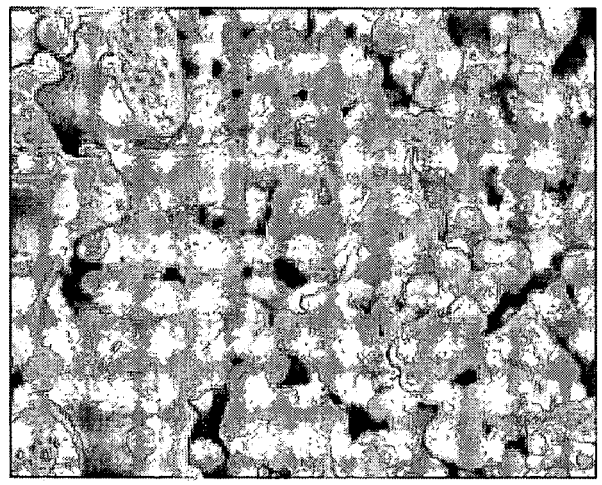
Figure 12:
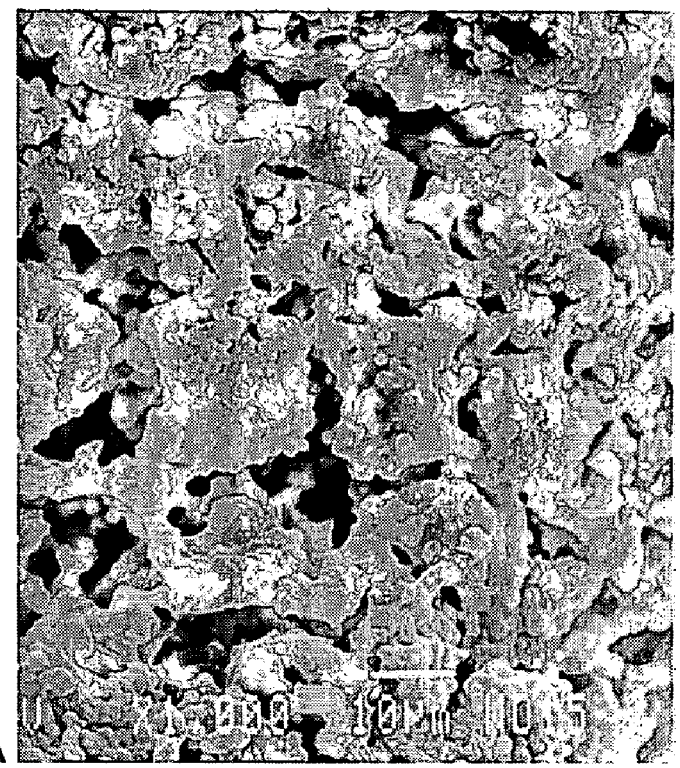
FIG. 12 shows silica gel prepared from DGS A: Using polyNIPAM as dopant; B: Using PEO with terminal Si(OEt)$_3$ groups as dopant (see experimental section in both cases)
Figure 12:
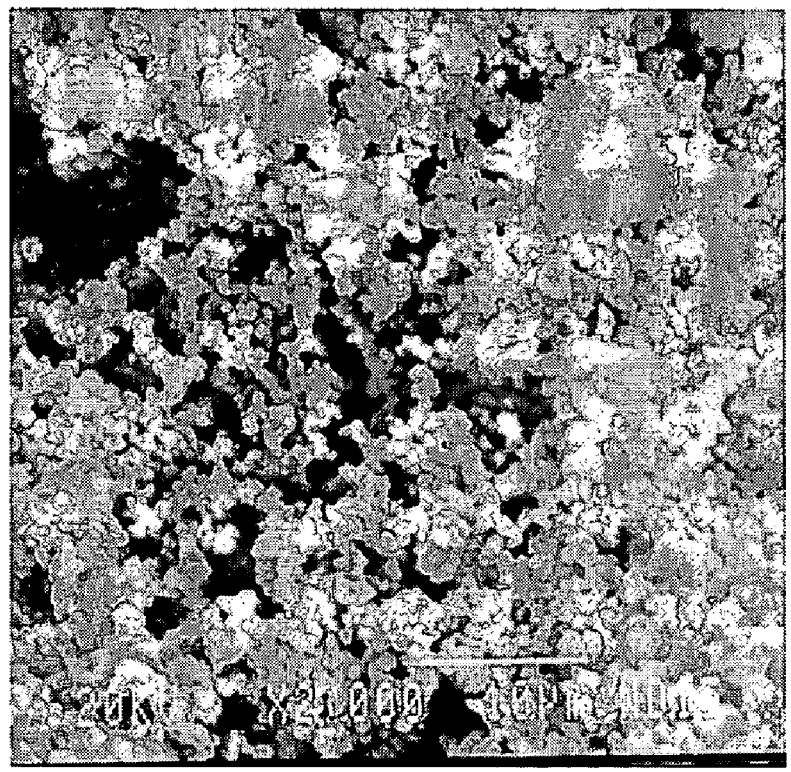

(with n=1), under conditions where a phase transition occurs before gelation, changed the aggregate size and morphology in a different manner (FIGS. 8 and 12B).

It was noted above that a particular advantage of the methods of the present invention is that they are amenable for the preparation of biomolecule-doped siliceous materials. Accordingly, the present invention further relates to a method of preparing siliceous materials comprising combining an organic polyol silane precursor, a biomolecule of interest and one or more additives under conditions suitable for hydrolysis and condensation of the precursor to a siliceous material, wherein the one or more additives are selected from the group consisting of one or more water-soluble polymers and one or more trifunctional silanes of Formula I:

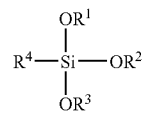

wherein R$^1$, R$^2$ and R$^3$ are the same or different and represent a group that may be hydrolyzed under normal sol-gel conditions to provide a Si—OH group; and R$^4$ is group that is not hydrolyzed under normal sol-gel conditions.

The present invention further relates to the siliceous material comprising a biomolecule or biological substance entrapped therein wherein the siliceous material is prepared using the methods described hereinabove.

Figure 13:
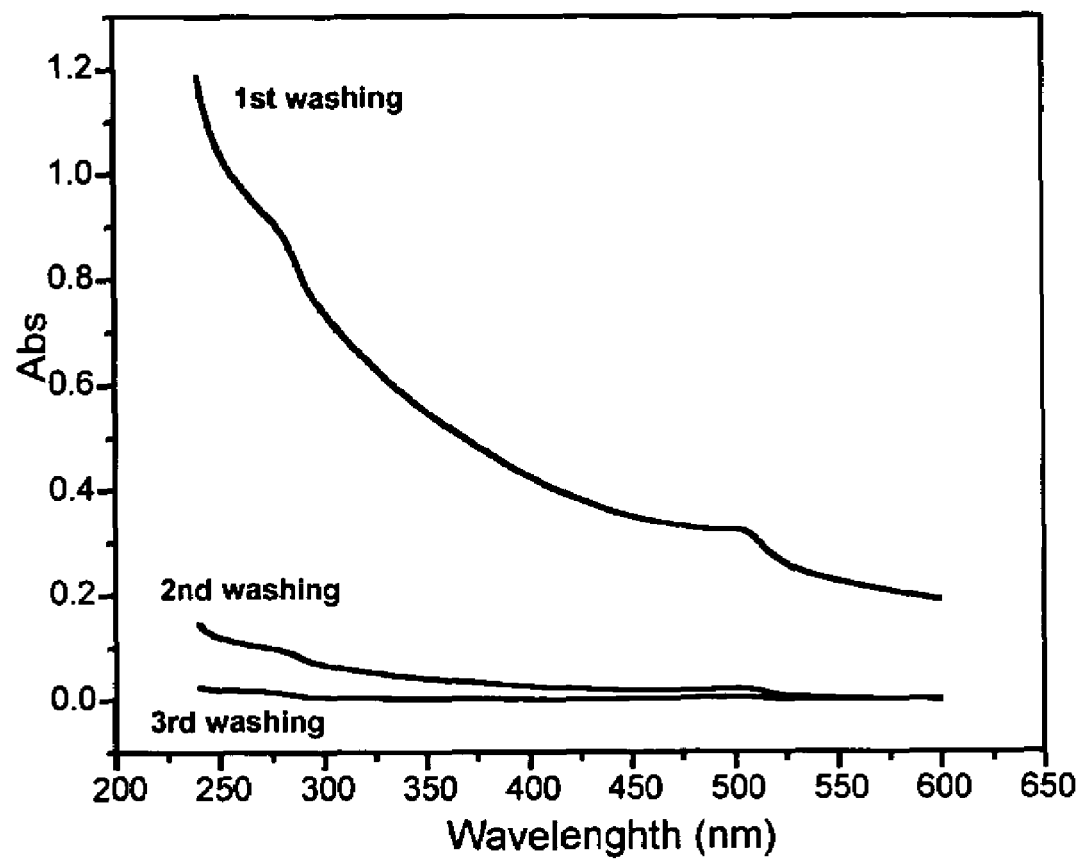
FIG. 13 shows UV-visible spectra of the washing solution of FITC labelled HSA.
Figure 14:
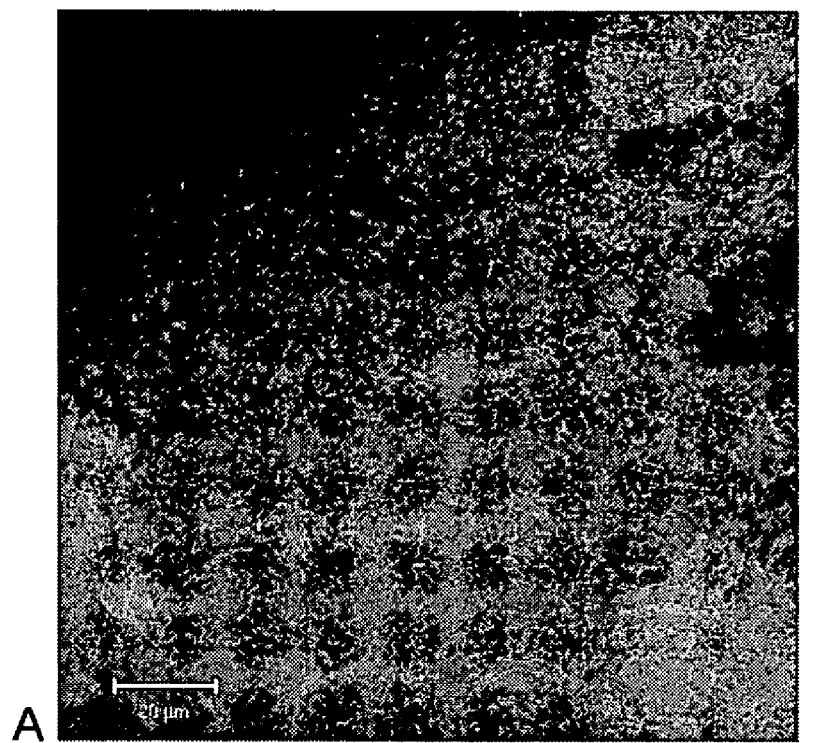
FIG. 14 shows Confocal Microscopy Images of the PEO/DGS gel entrapped with fluorescent FITC-HSA after the 3$^{rd}$ washing.
Figure 14:
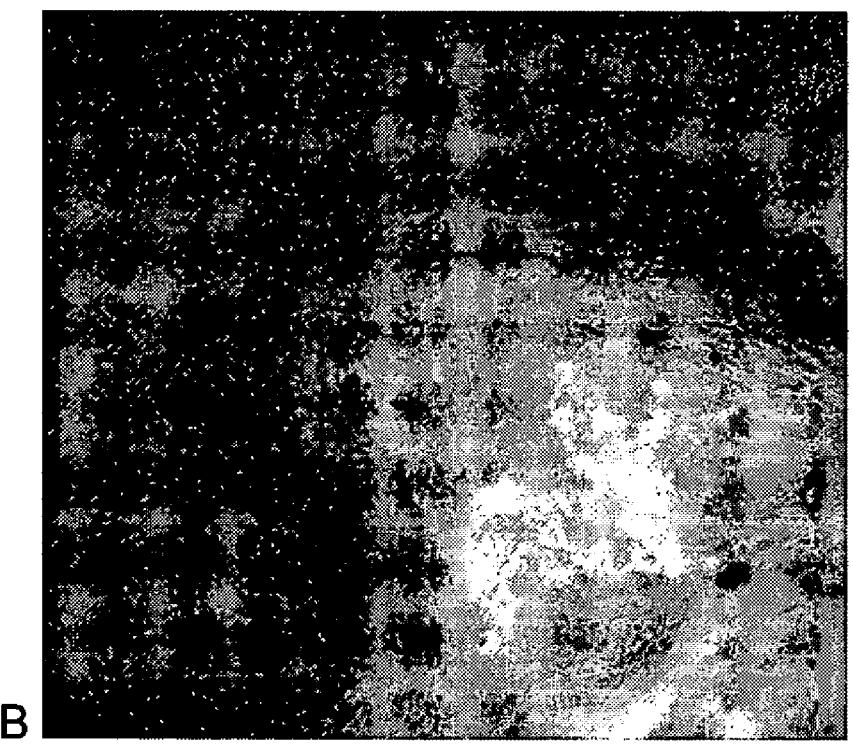

The incorporation of biomolecules into the silica monoliths prepared using the method of the present invention is exemplified by the silica formed in the presence of the surface active protein human serum albumin[39] (HSA) or lysozyme using a recipe incorporating 100,000 MW PEO as a dopant (Table 7). It was possible to partially remove the protein by extensive washing, as shown using fluorescently labelled HSA: the more PEO in the original recipe, the less protein remains in the column after washing. The washing liquors from the PEO/DGS/FITC-labelled HSA silica were examined by UV-visible spectroscopy. A very weak absorption signal could still be detected in the 3$^{rd}$ washing (FIG. 13). However, the resulting gel still contained significant quantities of HSA, as shown by the strong fluorescent signal observed by confocal microscopy after 3 days total soaking (FIG. 14). The addition of PPG-NH$_2$ to the sol changes the ultimate degree of proteins retention. As shown in Tables 7 and 8, PPG-NH$_2$ is much more efficient than other polymers in retaining proteins. Thus, in addition to morphological changes provided by the addition of a water soluble polymer, these polymers also play a role in controlling the total protein content in the silica monolith.

The meso/macroporous monoliths prepared using the methods of the invention undergo shrinkage, as is common for sol-gel derived silica. However, the magnitude of shrinkage of these materials is also significantly lower than that observed with TEOS-derived gels. After one month in water, the radial shrinkage of a 14 mm diameter cylinder of gel prepared with DGS/PEO is about 10% after one month. This is the same shrinkage for the pure DGS gel. If the gel is aged in open system without water, the shrinkage is about 14% for the DGS/PEO gel, 21% for the DGS gel and 43% for the TEOS gel. Accordingly, the present invention relates to a method of preparing a meso/macroporous silica monolith with improved shrinkage characteristics.

Further illustration of the protein stabilization capabilities of the materials prepared using the method of the present invention is exemplified by the silica formed from diglycerylsilane (DGS) combined with compound 1 or compound 2. Proteins entrapped in such materials include Src kinase, luciferase, Factor Xa and urease. These proteins are typically unstable in conventional sol gel materials derived from tetraalkoxysilanes or polyolsilanes. In fact, Src kinase entrapped in sol gels derived from precursors such as TMOS, TEOS and DGS provided no detectable enzyme activity, highlighting the unexpected and remarkable protein stabilizing ability of additives such as compounds 1 and 2 and the like. It was further demonstrated that materials formed from such precursors are sufficiently porous to allow accessibility of polypeptides containing up to 15 amino acid residues to the entrapped enzyme, and that phosphorylation of the peptides by entrapped Src kinase and inhibition of this process by small molecules and short peptides can be detected using a time-resolved fluorescence resonance energy transfer method based on LANCE™ technology.[40]

Accordingly, the present invention provides a method of preparing siliceous materials with enhanced protein stabilizing ability comprising combining an organic polyol silane precursor with one or more additives under conditions suitable for hydrolysis and condensation of the precursor to a siliceous material, wherein the one or more additives are selected from one or more trifunctional silanes of Formula I:

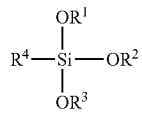

I wherein $R^1$, $R^2$ and $R^3$ are the same or different and represent a group that may be hydrolyzed under normal sol-gel conditions to provide a Si—OH group and $R^4$ is polyol-(linker)-. In embodiments of the invention, the polyol in $R^4$ is derived from glucose or maltose and the linker is an alkylene amide group. In still further embodiments of the invention, the compound of Formula I is compound 1 or compound 2. In other embodiments of the invention, the protein is a kinase, luciferase, or urease or is Factor Xa.

When the protein entrapped in the sol gel material prepared from DGS and compound was Src kinase, improvements in the signal/background (S/B) ratio were obtained by adding adenosine triphosphate (ATP) to the sol before the encapsulation of the enzyme had taken place. Both ATP and peptide competitive inhibitors were shown to inhibit the activity of the entrapped Src kinase with $IC_{50}$ values that were very similar to those obtained in solution. Accordingly, in an embodiment of the present invention, the method of preparing siliceous materials with enhanced protein stabilizing ability further comprises combining the organic polyol silane precursor and one or more additives with a substrate for the protein to be entrapped. When the protein is a kinase, the substrate may be a source of phosphate, for example, ATP.

The formation of silica by a sol-gel route involves a complex series of hydrolyses and condensations.[12] When multidentate starting materials are used, such as silanes derived from glycerol, sorbitol, mannitol, dextrans or other sugar-derived materials, the number of equilibria involved in the reaction cascade from starting materials to silica increases significantly. During this process, low molecular weight materials begin to oligomerize and polymerize. In the absence of significant amounts of other dopants, the final silica monolith forms an optically clear material that contains water, alcohols and other added dopants. The entire process occurs in one phase.

The expedient of adding water soluble polymers and other additives, such as compounds of Formula I which can participate in the sol gel chemistry, to the original sol complicates the evolution of the silica. The situation is reminiscent of dispersion polymerization where, after oligomerization, the growing polymer nucleates particles.[41] In this case, the growing silica polymer precipitates from the sol while gelation continues. The specific timing, degree of polymerization, ultimate morphology (including size of the primary particles and aggregates, thickness of the binding silica layers, uniformity of the particle size, pore sizes and porosity) is affected by the quantity, molecular weight and specific molecular characteristics of the additives as shown above.

There are distinctions between the work described here and previous literature reports. These include the nature of the silicon-based starting materials and the interactions of the additives with them. First, the nature of the alkoxy groups on the silane precursors of the present invention gives these compounds very different pH cure profiles than silanes derived from mono-hydroxysilanes; the residual alcohols of the precursors of the present invention act to plasticize the developing silica network. They also provide an environment which is not destabilizing to entrapped protein. Another distinction is the thermal dependence of the reaction. Gelation occurs at ambient temperature over a wide pH range, again facilitating the incorporation of proteins and other biomolecules in the method of the present invention. Finally, the shrinkage of these monoliths of the present invention is significantly reduced when compared to TEOS- or TMOS-derived materials, again providing a more stable environment for entrained biomolecules.

Another distinction between materials containing compounds of Formula I and previous materials reported in the literature is that the covalently tethered functional group (gluconamide, maltonamide, etc) cannot be removed upon exhaustive washing, contrary to the findings for hydrolysable functional groups. This renders permanent sites in the silica that can be used to retain water and ultimately to maintain protein activity. As shown below, such materials, when used to entrap biomolecules, allow for multiple reuses of the entrapped protein even after many washing steps.

The use of different additives, of different MW and quantities in the sol-gel silica recipe allows the possibility of tuning surface area, total porosity, morphology and protein retention of the resulting structure, and the magnitude of shrinkage and strength over wide ranges prepared by the sol-gel method from sugar alcohol and related silanes. Another advantage with this combination of reagents over traditional routes is the mild thermal conditions that can be used for its manufacture. In particular, the synthetic route is compatible with the incorporation of proteins and other biomolecules.

(ii) Uses

The siliceous materials prepared using the methods of the invention are novel accordingly, the present invention further includes all uses of these materials, including, but not limited to, their use in chromatography, biosensors, immobilizing enzymes, affinity supports and the like. In many applications for these materials, a biological substance has been entrapped within its matrixes.

Accordingly, the present invention includes the use of a siliceous material comprising an active biological substance entrapped therein, as biosensors, immobilized enzymes or as affinity chromatography supports. Therefore, the present invention also includes a method for the quantitative or qualitative detection of a test substance that reacts with, binds to and/or whose reaction is catalyzed by an active biological substance, wherein said biological substance is encapsulated within a siliceous material, and wherein said siliceous material is prepared using a method of the invention. The quantitative/qualitative method comprises (a) preparing the siliceous material comprising said active biological substance entrapped within a porous, silica matrix prepared using a method of the invention; (b) bringing said biological-substance-containing siliceous material into contact with a gas or aqueous solution comprising the test substance; and (c) quantitatively or qualitatively detecting, observing or measuring the change in one or more characteristics in the biological substance entrapped within the siliceous material or, alternatively, quantitatively or qualitatively detecting, observing or measuring the change in one or more characteristics in the test substance. Such tests may be performed in various morphologies that will be readily understood by those skilled in the art. Without limitation, these can include microarrays, such as would be achieved using a pinspotter.[42]

In particular, the invention includes a method wherein the change in one or more characteristics of the entrapped biological substance is qualitatively or quantitatively measured by spectroscopy, utilizing one or more techniques selected from the group consisting of UV, IR, visible light, fluorescence, luminescence, absorption, emission, excitation and reflection.

Also included is a method of storing a biologically active biological substance in a silica matrix, wherein the biological substance is an active protein or active protein fragment, wherein the silica matrix prepared using a method of the invention.

The meso/macroporous silica monoliths prepared using the method of the invention are especially useful in chromatographic applications. For the preparation of a chromatographic column, the silica precursor (optionally in hydrolyzed form) and one or more water-soluble polymer (and other additives) may be placed into a chromatographic column before phase transition and gelation occurs.

The present invention therefore relates to a method of preparing a monolithic silica chromatographic column comprising placing a solution comprising an organic polyol silane precursor and one or more additives selected from water-soluble polymers and a compound of Formula I, wherein $R^4$ is group selected from polymer-(linker)$_n$- and

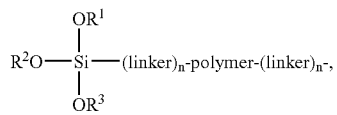

where n is 0-1, in a column under conditions suitable for a phase transition to occur before gelation.

Other additives known in the art for use with sol gel columns may also be used in the method of the invention. This includes, for example, substances, such as aminopropyltriethoxysilane (APTES), which provide cationic sites that counterbalance the anionic charge of the silica to reduce non-selective interactions. Other amino-functional materials described above PEG-NH$_2$, PPG-NH$_2$ and/or PAM, can similarly serve this role.

In embodiments of the invention the chromatographic column is a capillary column. Conventional capillary columns comprise a cylindrical article having an inner wall and an outer wall and involve a stationary phase permanently positioned within a circular cross-section tube having inner diameters ranging from 5 μm to 0.5 mm. The tube wall may be made of glass, metal, plastic and other materials. When the tube wall is made of glass, the wall of the capillary possesses terminal Si—OH groups which can undergo a condensation reaction with terminal Si—OH or Si—OR groups on the silica monolith to produce a covalent Si—O—Si linkage between the monolith and the capillary wall. This provides a column with structural integrity that maintains the monolith within the column. Due to the small dimensions of a capillary column, the solutions comprising the silica precursor and water soluble polymer may be introduced into the capillary by the application of a modest vacuum.

Some of the additives can be removed or eluted prior to chromatography by rinsing with an appropriate solvent, such as water and/or alcohol. The column may be further prepared by methods such as supercritical drying or the use of a reagent such as a silane or other coupling agent to modify the surface of the exposed silica. The monolith may also be stored with the additives interspersed within.

In embodiments of the invention, the silica monolith prepared using the method of the invention is further derivatized to allow tailoring of the monolith for a variety of chromatographic separations. While the examples described herein refer exclusively to the use of entrapped proteins for affinity based separations, it should be apparent to those skilled in the art that a variety of modifications can be made to the column to effect separations using other types of interactions. For example, a surface may be incorporated into the monolith by entrapment of coated particles that is useful for reverse phase chromatography without the need for frits. Such surfaces may comprise long chain alkyl groups or other non-polar groups. Alternatively, the silica skeleton itself may be derivatized by reacting the Si—OH or Si—OR groups on the silica with reagents that convert these functionalities to surface linkages to other organic groups such as alkyls, aryls or functional organic groups (e.g. carboxylates or amines). Provided that the materials are not calcined prior to derivatization the material is distinct from that described by Nakanishi. Indeed, such material may show different behaviour than the monolithic columns described by Nakanishi since the non-calcined silica would have a much higher proportion of Q2 and Q3 groups relative to Q4 groups, which may aid in providing high surface coverage for a derivatizing group. In still further embodiments, other organic groups may include chiral molecules that facilitate the separation of chiral compounds. These derivatizations are known in the art and are included within the scope of the present invention.

The present invention also includes chromatographic columns comprising the silica monoliths prepared as described herein. Accordingly the invention includes a chromatographic column comprising a silica monolith prepared by combining an organic polyol silane precursor and one or more additives selected from one or more water-soluble polymers and one or more compounds of Formula I, wherein $R^4$ is group selected from polymer-(linker)$_n$- and

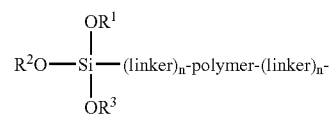

and n is 0-1, under conditions where a phase transition occurs before gelation.

In addition, the invention includes the use of a silica monolith prepared using a method of the invention and comprising an active biological substance entrapped therein, as chromatographic columns, biosensors, immobilized enzymes or as affinity chromatography supports. Therefore, the present invention relates to the use of a silica monolith comprising an active biological substance entrapped therein to quantitatively or qualitatively detect a test substance that reacts with, binds to and/or whose reaction is catalyzed by said encapsulated active biological substance, and wherein said silica monolith is prepared using a method of the invention.

Also included is a method for the quantitative or qualitative detection of a test substance that reacts with, binds to and/or whose reaction is catalyzed by an active biological substance, wherein said biological substance is encapsulated within a silica monolith, and wherein said silica monolith is prepared using a method of the invention. The quantitative/qualitative method comprises (a) preparing a silica monolith comprising said active biological substance entrapped within a porous, silica matrix prepared using the method of the invention; (b) bringing said biological-substance-comprising silica monolith into contact with a gas or aqueous solution comprising the test substance; and (c) quantitatively or qualitatively detecting, observing or measuring the change in one or more characteristics in the biological substance entrapped within the silica monolith or, alternatively, quantitatively or qualitatively detecting, observing or measuring the change in one or more characteristics in the test substance.

In particular, the invention includes a method, wherein the change in one or more characteristics of the entrapped biological substance is qualitatively or quantitatively measured by spectroscopy, utilizing one or more techniques selected from the group consisting of UV, IR, visible light, fluorescence, luminescence, absorption, emission, excitation and reflection.

(iii) Specific Application to Bioaffinity Chromatography

The present inventors have developed biocompatible, meso/macroporous silica materials that can be used for biomolecule (e.g. protein) entrapment and have shown that capillary columns based on this material can be prepared that are suitable for pressure driven liquid chromatography and are compatible with mass spectral (MS) detection. The columns were prepared using a mixture of the biomolecule-compatible silica precursor diglycerylsilane (DGS),[6,43,44] polyethylene oxide (PEO, MW 10,000), which controls morphology, aminopropyltriethoxysilane (APTES), which provides cationic sites that counterbalance the anionic charge of the silica to reduce non-selective interactions,[34] and a buffered solution of the biomolecule of interest to provide bioaffinity sites within the column. The resulting sol mixture was loaded into fused silica capillaries (150-250 μm i.d.), whereupon phase separation of PEO occurred followed by gelation of the silica. The phase separation of the polymer from the silica resulted in a pore distribution which produced large macropores (>0.1 μm) to allow good flow of eluent with minimal backpressure, and mesopores (ca. 3-5 nm diameter) that retained a significant fraction of the entrapped protein.

Accordingly, the present invention relates to a method of preparing a monolithic silica column having an active biomolecule entrapped therein comprising combining:

a) a polyol-silane derived silica precursor;
b) one or more additives selected from one or more water soluble polymers and one or more compounds of Formula I, wherein $R^4$ is group selected from polymer-(linker)$_n$- and

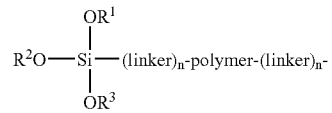

and n is 0-1; and
c) a biomolecule;

under conditions wherein a phase separation occurs before gelation.

In embodiments of the present invention, the additive is one or more water soluble polymers or compound of Formula I, wherein $R^4$ is

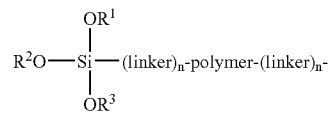

and n is 0-1. In further embodiments, $R^1$, $R^2$ and $R^3$ are the same or different and are selected from $C_{1-4}$alkyl, in particular methyl or ethyl. In still further embodiments, linker is a $C_{1-4}$alkylene group, in particular a $C_{2-3}$alkylene group and n is 1. In still further embodiments, the water soluble polymer and the polymer group in $R^4$ are both selected from PEO, polyNIPAM and PEO-NH$_2$.

In an embodiment of the invention, the organic polyol silane silica precursor, one or more additives and biomolecule are also combined with a substance which provides cationic sites that counterbalance the anionic charge of the silica to reduce non-selective interactions, for example, aminopropyltriethoxysilane (APTES), PEG-NH$_2$, PPG-NH$_2$ and/or PAM, specifically APTES. In further embodiments of the invention, the amount of a substance which provides cationic sites that counterbalance the anionic charge of the silica to reduce non-selective interactions is kept below levels which cause retention of anionic species. This amount can readily determined by a person skilled in the art. For example, when this substance is APTES, an amount in the range of about 0.2-0.4% (w/v), preferably about 0.3%, was found to be optimal for minimizing non-selective retention.

In further embodiments of the present invention, the monolithic silica is prepared directly in a chromatographic column. The organic polyol silane silica precursor may be hydrolyzed, for example, by dissolution in aqueous solution with optional sonication, and optionally in the presence of acid, for example 1M HCl, filtered to remove unwanted particulates if necessary, and the hydrolyzed precursor may then be combined with buffered solutions of the one or more additives, biomolecule and any further additives. In particular the hydrolyzed precursor may be combined with buffered solutions of one or more additives, biomolecule and a substance which provides cationic sites that counterbalance the anionic charge of the silica to reduce non-selective interactions, for example, aminopropyltriethoxysilane (APTES), PEG-NH$_2$, PPG-NH$_2$ and/or PAM, specifically APTES. The resulting mixture may then be transferred to a column before phase separation and gelation occur. In a further embodiment of the invention, the inner surface of the column is pre-treated with a substance to promote adhesion of the monolithic silica, for example aminopropyltriethoxysilane (APTES), PEG-NH$_2$, PPG-NH$_2$ and/or PAM, specifically APTES. In still further embodiments of the invention, the column is a capillary column.

As a specific application of the new bioaffinity columns, the ability of small enzyme inhibitors to interact with an entrapped enzyme, and thus be retained on the column, was examined. The enzyme chosen for this study was the clinically relevant protein dihydrofolate reductase (DHFR). DHFR catalyzes the NADPH-dependent reduction of dihydrofolate (DHF) to tetrahydrofolate, which is then used as a co-factor in the biosynthesis of thymidylate, purines and several amino acids.[45,46,47] DHFR is an essential enzyme in the cell and is the target for antifolate drugs.[48] A key reason for choosing this protein was that there are a large number of known DHFR inhibitors that span 5 decades of affinity, providing a useful model system for examining the binding of inhibitors to the entrapped enzyme.[48] This enzyme has also been shown to remain active and can bind to inhibitors when entrapped in DGS derived materials.[43]

Examination of ligand binding was done via frontal affinity chromatography with mass spectrometric detection (FAC/MS). This method has recently been promoted as a potential high-throughput screening tool that is amenable to compound mixtures.[17] The basic premise is that continuous infusion of a compound will allow for equilibration of the ligand between the free and bound states, where the precise concentration of free ligand is known. In this case, the breakthrough time of the compound will correspond to the affinity of the ligand for the immobilized biomolecule—ligands with higher affinity will break through later. As shown hereinbelow, DHFR loaded columns derived by the sol-gel method are suitable for FAC/MS based screening of ligand mixtures, and can be used to identify nanomolar inhibitors of the immobilized protein.

Formation of columns within fused silica capillaries, for example 150-250 µm i.d. capillaries, provides a system that requires only very small amounts of protein (50 µmol loading, 12 µmol active protein) to produce a useful bioaffinity column. Such columns are suitable for pressure-driven liquid chromatography and can be operated at relatively high flow rates (up to 500 µL.min$^{-1}$) with low backpressures. More importantly, the operation of these columns with low ionic strength eluents allows direct interfacing to an electrospray mass spectrometer, allowing direct identification of small molecule identities using multiple reaction monitoring mode. The ability to detect inhibitors present in compound mixtures via retention time combined with MS detection can be very powerful for high-throughput screening of compound mixtures. The extension of FAC/MS technology to entrapped proteins can improve the versatility of the FAC method, particularly since a wide range of proteins, including membrane-bound receptors,[49] can be entrapped in sol-gel derived silica.

The present invention further relates to a chromatographic column prepared by combining a polyol-silane derived silica precursor with one or more additives, a biomolecule and, optionally, a substance which provides cationic sites that counterbalance the anionic charge of the silica to reduce non-selective interactions, under conditions wherein a phase separation occurs before gelation. Also included within the scope of the present invention is the use of this column, for example but not limited to, in methods for immunoaffinity chromatography, sample cleanup, solid phase extraction or preconcentration of analytes, removal of unwanted contaminants (for example by antibody binding), solid phase catalysis or frontal affinity chromatography (with or without mass spectral detection). The invention also includes a method of performing immunoaffinity chromatography, sample cleanup, solid phase extraction or preconcentration of analytes, removal of unwanted contaminants (for example by antibody binding), solid phase catalysis or frontal affinity chromatography (with or without mass spectral detection) comprising (a) applying a sample to a chromatographic column prepared by combining a polyol-silane derived silica precursor with one or more additives, a biomolecule and, optionally, a substance which provides cationic sites that counterbalance the anionic charge of the silica to reduce non-selective interactions, under conditions wherein a phase separation occurs before gelation; and (b) performing immunoaffinity chromatography, sample cleanup, solid phase extraction or preconcentration of analytes, removal of unwanted contaminants (for example by antibody binding), solid phase catalysis or frontal affinity chromatography (with or without mass spectral detection).

The following non-limiting examples are illustrative of the present invention:

EXAMPLES

Materials and Methods for Examples 1-6

D-Gluconolactone (glulactone), D-maltose monohydrate, iodine, silver carbonate, 3-aminopropyltriethoxysilane (Aldrich Chemical Co.), anhydrous methyl sulfoxide and dextran (Sigma Chemical Co.) were used as received. The strong cationic exchange resin Amberlite IR-120 (Aldrich Chemical Co.) was rinsed with distilled water before use. D-Maltonolactone (maltolactone), dextran lactone (from dextran, average MW 10200) and dextran lactone (from dextran, average MW 43000) were prepared according to the literature.[50] Poly(ethylene glycol) (average MW 200, 600, 2000, 10000) was purchased from Aldrich Chemical Co. Triethoxysilane, and allyl bromide were provided by Aldrich. Platinum-divinyltetramethyldisiloxane complex in vinyl-terminated polydimethylsiloxane, provided by Gelest Inc., was used as the Pt catalyst. Dichloromethane and pentane were distilled from CaH, EtOH was distilled from Mg before use.

$^1$H and $^{13}$C NMR were recorded at room temperature on a Bruker AC-200 spectrometer; solid state $^{13}$C and $^{29}$Si CPMAS NMR spectra were recorded on a Bruker AC-300 at 75.47 and 59.62 MHz, respectively. FT-IR spectra were obtained on a Perkin-Elmer 283 spectrometer, samples were prepared as KBr pellets. Electrospray mass spectra were recorded on a Micromass Quattro LC, triple quadruple MS. Mean mobility data were recorded on a PALS Zeta Potential Analyzer Ver. 3.19. Thermogravimetric analyses were obtained using a Thermowaage Sta STA 409.

Example 1

Preparation of Silsesquioxane Precursors

GluconamideSi, 1. To a solution of D-gluconolactone (0.91 g, 5.2 mmol) in DMSO (10 mL) and EtOH (5 mL) was added 3-aminopropyltriethoxysilane (1.11 g, 5.0 mmol). The mixture was stirred at 60° C. for 20 h. The solvents were evaporated under vacuum and oil residue was dissolved in dichloromethane. Unreacted D-gluconolactone was filtered off, the filtrate was concentrated and added to a large amount of pentane. The white precipitate was collected and dried in vacuo to give 1 as pale yellow solid, 1.83 g (92% yield). $^1$H NMR (200.2 MHz, d$_6$-DMSO): δ 0.50 (SiCH$_2$), 1.12 (t, 9H, J=6.98 Hz, SiOCH$_2$CH$_3$), 1.45 (m, br, 2H, SiCH$_2$CH$_2$), 3.04 (m, 2H, CH$_2$NHCO), 3.74 (q, J=6.98 Hz, 6H, SiOCH$_2$CH$_3$), 3.40-5.32 (m, glucose ring CH and CH$_2$, and OH), 7.61 (s, br., 1H, NHCO). $^{13}$C NMR (50.3 MHz, d$_6$-DMSO): δ 7.8 (SiCH$_2$), 18.7-18.9 (SiOCH$_2$CH$_3$), 23.3 (SiCH$_2$CH$_2$), 41.5 (CH$_2$NHCO), 58.3 (SiOCH$_2$CH$_3$, overlapped), 64.0, 70.7, 72.1, 74.2, 73.0 (glucose ring CH and CH$_2$), 172.9 (NHCO). FT-IR (KBr): 1646 cm$^{-1}$ (ν(C=O)). MS-ESI (ES$^+$): 422.2 (M+Na, 100)$^+$, 400.2 (M+1, 15)$^+$, 354 (5), 236 (18).

MaltonamideSi, 2. To a solution of D-maltonolactone (0.75 g, 2.2 mmol) in DMSO (10 mL) and EtOH (5 mL) was added 3-aminopropyltriethoxysilane (0.44 g, 2.0 mmol). The mixture was stirred at 60° C. for 20 h. The solvents were evaporated under vacuum and oil residue was dissolved in dichloromethane. Unreacted D-maltonolactone was filtered off, the filtrate was concentrated and added to a large amount of pentane. White precipitate was collected and dried in vacuo to give 2 as pale yellow solid, 0.98 g (87% yield). $^1$H NMR (200.2 MHz, d$_6$-DMSO): δ 0.49 (m, br., 2H, SiCH$_2$), 1.08 (t, J=6.96 Hz, 9H, SiOCH$_2$CH$_3$), 1.43 (m, br., 2H, SiCH$_2$CH$_2$), 3.70 (q, J=6.96 Hz, 6H, SiOCH$_2$CH$_3$), 3.05-5.47 (m, CH$_2$NHCO and maltose CH and CH$_2$, and OH), 7.60 (NHCO) ppm. $^{13}$C NMR (50.3 MHz, d$_6$-DMSO): δ 7.8 (SiCH$_2$), 18.4~19.1 (SiOCH$_2$CH$_3$), 23.4 (SiCH$_2$CH$_2$), 41.3 (CH$_2$NHCO), 56.6 (SiOCH$_2$CH$_3$, overlapped), 61.3, 63.4, 69.8, 72.5~73.8 (overlapped), 80.6, 101.4 (maltose CH and CH$_2$), 172.9 (NHCO) ppm. FT-IR (KBr): 1643 cm$^{-1}$ (ν(C=O)). MS-ESI (ES$^+$): 584.3 (M+Na, 30)$^+$, 562.4 (M+1, 20)$^+$.

DextronamideSi-10K, 3a. To a solution of dextran10K-lactone (2.0 g, 0.2 mmol) in DMSO (50 mL) and EtOH (10 mL) was added 3-aminopropyltriethoxysilane (0.44 g, 2.0 mmol). The mixture was stirred at 60° C. for 48 h. The mixture was concentrated and added to large amount of dichloromethane. White precipitate was collected, washed with dichloromethane, and dried in vacuo to give 3a as white solid, 1.8 g.

DextronamideSi-40K, 3b. To a solution of dextran40K-lactone (4.3 g, 0.1 mmol) in DMSO (50 mL) and EtOH (10 mL) was added 3-aminopropyltriethoxylsilane (0.44 g, 2.0 mmol). The mixture was stirred at 60° C. for 48 h. The mixture was concentrated and added to large amount of dichloromethane. White precipitate was collected, washed with dichloromethane, and dried in vacuo to give 3b as white solid, 4.0 g.

Example 2

Preparation of PEO-Silyl Additives

[(CH$_2$CH$_2$O)$_p$(CH$_2$CH=CH$_2$)$_2$, 4a: The reaction was carried out under N$_2$ atmosphere to which a small amount of dry air had been added. To a solution of poly(ethylene glycol) (average MW 200, 10.0 g, 50 mmol) in THF (100 mL) at 0° C. was added NaH (2.4 g, 100.0 mmol) slowly over 30 min. The mixture was allowed to warm up to room temperature and stirred for 2 h. The mixture was cooled down to 0° C., allyl bromide (12.1 g, 100.0 mmol) was added. The mixture was warmed up to room temperature and stirred for further 15 h. White precipitate was filtered off and washed with THF (3×10 mL). The combined filtrate and washing solution and THF was evaporated to give pale yellow crude product. The crude product was purified by chromatography (SiO$_2$, 2% MeOH in CH$_2$Cl$_2$ as eluent) give allyl terminated poly(ethylene glycol), 4a as colorless oil, 11.1 g, (ca. 76% yield). $^1$H NMR (200.2 MHz, CDCl$_3$): δ 3.54-3.62 (m, 18H, PEO OCH$_2$), 3.96 (dd, 1H, J=5.6 Hz, J=1.4 Hz, CH$_2$=CHCH$_2$O), 3.97 (dd, 1H, J=5.6 Hz, J=1.4 Hz, CH$_2$=CHCH$_2$O), 5.14 (m, 4H, CH$_2$=CHCH$_2$O), 5.86 (m, 2H, CH$_2$=CHCH$_2$O) ppm. $^{13}$C NMR (50.3 MHz, CDCl$_3$): δ 69.2, 70.4 (PEO OCH$_2$), 72.0 (CH$_2$=CHCH$_2$O), 116.9 (CH$_2$=CHCH$_2$O), 134.6 (CH$_2$=CHCH$_2$O) ppm. MS (EI), m/z, 275 (28, M, n=4), 319 (100, M, n=5), 363 (80, M, n=6), 407 (13, M, n=7), 451(5, M, n=8).

(CH$_2$CH$_2$O)$_p$(CH$_2$CH=CH$_2$)$_2$, ATPEO600: 4b: To a solution of poly(ethylene glycol) (average MW 600, 6.0 g, ca. 10 mmol) in THF (100 mL) at 0° C. was added NaH (0.50 g, 20.8 mmol) slowly over 15 min. The mixture was allowed to warm up to room temperature and stirred for 5 h. The mixture was cooled down to 0° C., allyl bromide (2.42 g, 20.0 mmol) was added. The mixture was warmed up to 40° C. and stirred for further 3 h. White precipitate was filtered off and washed with THF (3×10 mL). Combined filtrate and washing solution, THF was evaporated to give pale yellow crude product. The crude product was purified by chromatography (SiO$_2$, 10% ethyl acetate in hexane as eluent) give allyl terminated poly(ethylene glycol), 4b as colorless oil, 6.1 g, (ca. 90% yield). $^1$H NMR (200.2 MHz, CDCl$_3$): δ 3.54-3.65 (m, 44H, PEO OCH$_2$), 3.97 (dd, 2H, J=5.6 Hz, J=1.1 Hz CH$_2$=CHCH$_2$O), 3.98 (dd, 2H, J=5.6 Hz, J=1.1 Hz CH$_2$=CHCH$_2$O), 5.19 (m, 4H, CH$_2$=CHCH$_2$O), 5.88 (m, 2H, CH$_2$=CHCH$_2$O) ppm. $^{13}$C NMR (50.3 MHz, CDCl$_3$): δ 69.4, 70.5 (PEO OCH$_2$), 72.2 (CH$_2$=CHCH$_2$O), 117.1 (CH$_2$=CHCH$_2$O), 134.7 (CH$_2$=CHCH$_2$O) ppm. MS (maldi), m/z, 693 (5, M+Na$^+$, n=13), 671 (4, M+1, n=13), 649 (8, M+Na$^+$, n=12), 627 (6, M+1, n=12), 605(12, M+Na$^+$, n=11), 583 (6, M+1, n=11), 561 (9, M+Na$^+$, n=10), 539 (5, M+1, n=10), 517 (7, M+Na$^+$, n=9), 495 (5, M+1, n=9), 473 (6, M+Na$^+$, n=8), 42.1 (100).

(CH$_2$CH$_2$O)$_p$(CH$_2$CH=CH$_2$)$_2$, 4c: To a solution of poly (ethylene glycol) (average MW 2000, 2.0 g, ca. 1 mmol) in THF (20 mL) at room temperature was added NaH (0.050 g, 2.1 mmol). The mixture was stirred at 50° C. for 2 h. Allyl bromide (0.24 g, 2.0 mmol) was added. The mixture was stirred at room temperature for further 10 h. White precipitate was filtered off and washed with THF (3×10 mL). Combined filtrate and washing solution, THF was evaporated to give pale brown crude product. The crude product was purified by chromatograph (SiO$_2$, CH$_2$Cl$_2$ as eluent) give allyl terminated poly(ethylene glycol), 4c as white solid, 1.89 g, (ca. 91% yield). $^1$H NMR (200.2 MHz, CDCl$_3$): δ 3.50-3.65 (m, 180H, PEO OCH$_2$), 3.97 (dd, 2H, J=5.6 Hz, J=1.3 Hz CH$_2$=CHCH$_2$O), 3.98 (dd, 2H, J=5.6 Hz, J=1.3 Hz CH$_2$=CHCH$_2$O), 5.16 (m, 4H, CH$_2$=CHCH$_2$O), 5.83 (m, 2H, CH$_2$=CHCH$_2$O) ppm. $^{13}$C NMR (50.3 MHz, CDCl$_3$): δ 69.2, 70.3 (PEO OCH$_2$), 72.2 (CH$_2$=CHCH$_2$O), 116.9 (CH$_2$=CHCH$_2$O), 134.5 (CH$_2$=CHCH$_2$O) ppm.

(CH$_2$CH$_2$O)$_p$(CH$_2$CH=CH$_2$)$_2$, 4d: To a solution of poly (ethylene glycol) (average MW 10K, 10 g, ca. 1 mmol) in THF (100 mL) at room temperature was added NaH (0.050 g, 2.1 mmol). The mixture was stirred at 50° C. for 2 h. Allyl bromide (0.24 g, 2.0 mmol) was added. The mixture was stirred at room temperature for further 10 h. White precipitate was filtered off and washed with THF (3×20 mL). Combined filtrate and washing solution, THF was evaporated to give pale brown crude product. The crude product was dissolved in dichloromethane (20 mL), added to large amount of diethyl ether to give white precipitate. Repeated precipitate procedure once more gave allyl terminated poly (ethylene glycol), 4d as white solid, 7.9 g, (ca. 77% yield). $^1$H NMR (200.2 MHz, CDCl$_3$): δ 3.48-3.70 (m, 900H, PEO OCH$_2$), 3.96 (m, 4H, CH$_2$=CHCH$_2$O), 5.18 (m, 4H, CH$_2$=CHCH$_2$O), 5.84 (m, 2H, CH$_2$=CHCH$_2$O) ppm. $^{13}$C NMR (50.3 MHz, CDCl$_3$): δ 69.2-70.4 (PEO OCH$_2$), 72.1 (CH$_2$=CHCH$_2$O), 116.9 (CH$_2$=CHCH$_2$O), 134.6 (CH$_2$=CHCH$_2$O) ppm.

$(CH_2CH_2O)_p[(EtO)_3Si(C_3H_6)]_2$, 5a: To a mixture of 4a (1.98 g, 7.1 mmol) and triethoxylsilane (2.33 g, 14.2 mmol) one drop of Karstedt s Pt catalyst was added. The mixture was stirred at room temperature for 2 h (the reaction was monitored by $^1$H NMR). The volatile organics was removed at 100° C. under vacuum. The residue was diluted with $CH_2Cl_2$ (50 mL), activated charcoal (0.5 g) was added, the mixture was stirred at room temperature overnight. After filtering through charcoal, $CH_2Cl_2$ was evaporated off to give 5a as colorless oil, 4.20 g, ca. 98% yield. FTIR (neat), ν (cm$^{-1}$) 2975s, 2929s, 2885s, 1635w, 1443m, 1391s, 1366w, 1296w, 1262w, 1195m, 1167s, 1106s, 1082s, 959s, 793s, 694w; $^1$H NMR (200.2 MHz, CDCl$_3$): δ 0.57 (m, 4H, SiCH$_2$), 1.17 (t, 18H, J=7.0 Hz, SiOCH$_2$CH$_3$), 1.60 (m, 4H, SiCH$_2$CH$_2$CH$_2$), 3.38 (m, 4H, SiCH$_2$CH$_2$CH$_2$), 3.52-3.60 (m, 18H, PEO OCH$_2$), 3.78 (dd, 4H, J=7.0 Hz, J=14.0 Hz, SiOCH$_2$CH$_3$) ppm. $^{13}$C NMR (50.3 MHz, CDCl$_3$): δ 6.5 (SiCH$_2$), 18.4 (SiOCH$_2$CH$_3$), 23.0 (SiCH$_2$CH$_2$CH$_2$), 58.4 (SiOCH$_2$CH$_3$), 70.1, 70.7 (PEO OCH$_2$), 73.7 (SiCH$_2$CH$_2$CH$_2$) ppm.

$(CH_2CH_2O)_n[(EtO)_3Si(C_3H_6)]_2$, 5b: To a mixture of 4b (2.1 g, ca. 3 mmol) and triethoxylsilane (1.2 g, 6.9 mmol) one drop of Karstedt s Pt catalyst was added. The mixture was stirred at room temperature for 1 h (the reaction was monitored by $^1$H NMR). The volatile organics was removed at 110° C. under vacuum. The residue was diluted with $CH_2Cl_2$ (50 mL), activated charcoal (0.5 g) was added, the mixture was stirred at room temperature overnight. After filtering through charcoal, $CH_2Cl_2$ was evaporated off to give 5b as colorless oil, 2.45 g, ca. 80% yield. FTIR (neat), ν (cm$^{-1}$) 2975s, 2928s, 2884s, 2741w, 1741w, 1631w, 1459m, 1445m, 1391m, 1352w, 1297w, 1257w, 1107s, 1083s, 959m, 794m, 699w; $^1$H NMR (200.2 MHz, CDCl$_3$): δ 0.61 (m, 4H, SiCH$_2$), 1.20 (t, 18H, J=7.1 Hz, SiOCH$_2$CH$_3$), 1.64 (m, 4H, SiCH$_2$CH$_2$CH$_2$), 3.41 (m, 4H, SiCH$_2$CH$_2$CH$_2$), 3.57-3.63 (m, 56H, PEO OCH$_2$), 3.80 (dd, 4H, J=7.1 Hz, J=14.0 Hz, SiOCH$_2$CH$_3$) ppm. $^{13}$C NMR (50.3 MHz, CDCl$_3$): δ 6.5 (SiCH$_2$), 18.4 (SiOCH$_2$CH$_3$), 23.0 (SiCH$_2$CH$_2$CH$_2$), 58.5 (SiOCH$_2$CH$_3$), 70.1, 70.7 (PEO OCH$_2$), 73.8 (SiCH$_2$CH$_2$CH$_2$) ppm.

$(CH_2CH_2O)_p[(EtO)_3Si(C_3H_6)]_2$, 5c: To a mixture of 4c (2.0 g, ca. 1 mmol) and triethoxylsilane (0.36 g, 2.2 mmol) in dichloromethane (20 mL) one drop of Karstedt s Pt catalyst was added. The mixture was stirred under refluxing for 3 h (the reaction was monitored by $^1$H NMR). The solvent was evaporated and thereafter the volatile organics was removed at 110° C. under vacuum. The residue was diluted with $CH_2Cl_2$ (50 mL), activated charcoal (0.5 g) was added, the mixture was stirred at room temperature overnight. After filtering through charcoal, $CH_2Cl_2$ solution was concentrated and thereafter added to large amount of diethyl ether to give 5c as colorless solid, 2.1 g, ca. 88% yield. FTIR (neat, KBr), ν (cm$^{-1}$) 2975s, 2929s, 2885s, 1633w, 1459m, 1391s, 1366w, 1296w, 1262w, 1257w, 1194m, 1167s, 1106s, 1082s, 959s, 794s, 698w $^1$H NMR (200.2 MHz, CDCl$_3$): δ 0.89 (m, 4H, SiCH$_2$), 1.18 (t, 18H, J=7.1 Hz, SiOCH$_2$CH$_3$), 1.54 (m, 4H, SiCH$_2$CH$_2$CH$_2$), 2.65 (m, 4H, SiCH$_2$CH$_2$CH$_2$), 3.49-3.72 (m, 188H, PEO OCH$_2$ and SiOCH$_2$CH$_3$, overlapped) ppm. $^{13}$C NMR (50.3 MHz, CDCl$_3$): δ 10.4 (SiCH$_2$), 18.1 (SiOCH$_2$CH$_3$), 22.6 (SiCH$_2$CH$_2$CH$_2$), 58.1 (SiOCH$_2$CH$_3$), 69.2-70.2, overlapped (PEO OCH$_2$ and SiCH$_2$CH$_2$CH$_2$) ppm.

$(CH_2CH_2O)_p[(EtO)_3Si(C_3H_6)]_2$, 5d: To a mixture of 4 d (5 g, ca. 0.5 mmol) and triethoxylsilane (0.18 g, 1.1 mmol) in dichloromethane (50 mL) one drop of Karstedt s Pt catalyst was added. The mixture was stirred refluxing for 5 h (the reaction was monitored by $^1$H NMR). The solvent was evaporated and thereafter the volatile organics was removed at 110° C. under vacuum. The residue was diluted with $CH_2Cl_2$ (100 mL), activated charcoal (1.0 g) was added, the mixture was stirred at room temperature overnight. After filtering through charcoal, $CH_2Cl_2$ solution was concentrated and thereafter added to large amount of diethyl ether to precipitate white solid. Repeated precipitation procedure gave 5d as white solid, 2.7 g, ca. 50% yield. FTIR (neat, KBr), ν (cm$^{-1}$) 2974s, 2929s, 2885s, 1631w, 1454m, 1391s, 1364w, 1266w, 1257w, 1167s, 1082s, 959m, 794m, 698w; $^1$H NMR (200.2 MHz, CDCl$_3$): δ 0.66 (m, 4H, SiCH$_2$), 1.20 (m, 18H, SiOCH$_2$CH$_3$), 1.56 (m, 4H, SiCH$_2$CH$_2$CH$_2$), 2.65 (m, 4H, SiCH$_2$CH$_2$CH$_2$), 3.20-3.90 (m, 910H, PEO OCH$_2$ and SiOCH$_2$CH$_3$, overlapped) ppm. $^{13}$C NMR (50.3 MHz, CDCl$_3$): δ 6.2 (SiCH$_2$), 18.0 (SiOCH$_2$CH$_3$), 23.0 (SiCH$_2$CH$_2$CH$_2$), 58.2 (SiOCH$_2$CH$_3$), 68.8-70.3, overlapped (PEO OCH$_2$ and SiCH$_2$CH$_2$CH$_2$) ppm.

Example 3

Preparation of DGS/Modified PEO Gel

DGS (0.2648 g, 1.27 mmol) was mixed with (EtO)$_3$Si (CH$_2$)$_3$PEO(CH$_2$)$_3$Si(OEt)$_3$ (Example 3, 0.1274 g, 0.053 mmol) and added with water (600 L, 33.3 mmol). The mixture was sonicated at 0° C. for 1.5 h during which time a turbid solution formed. Then TRIS buffer (600 L, 50 mM, pH=8.4) was added. The gel formed starting at the bottom of the solution after 5 min.

Example 4

Preparation of Samples 6-15

Figure 5:
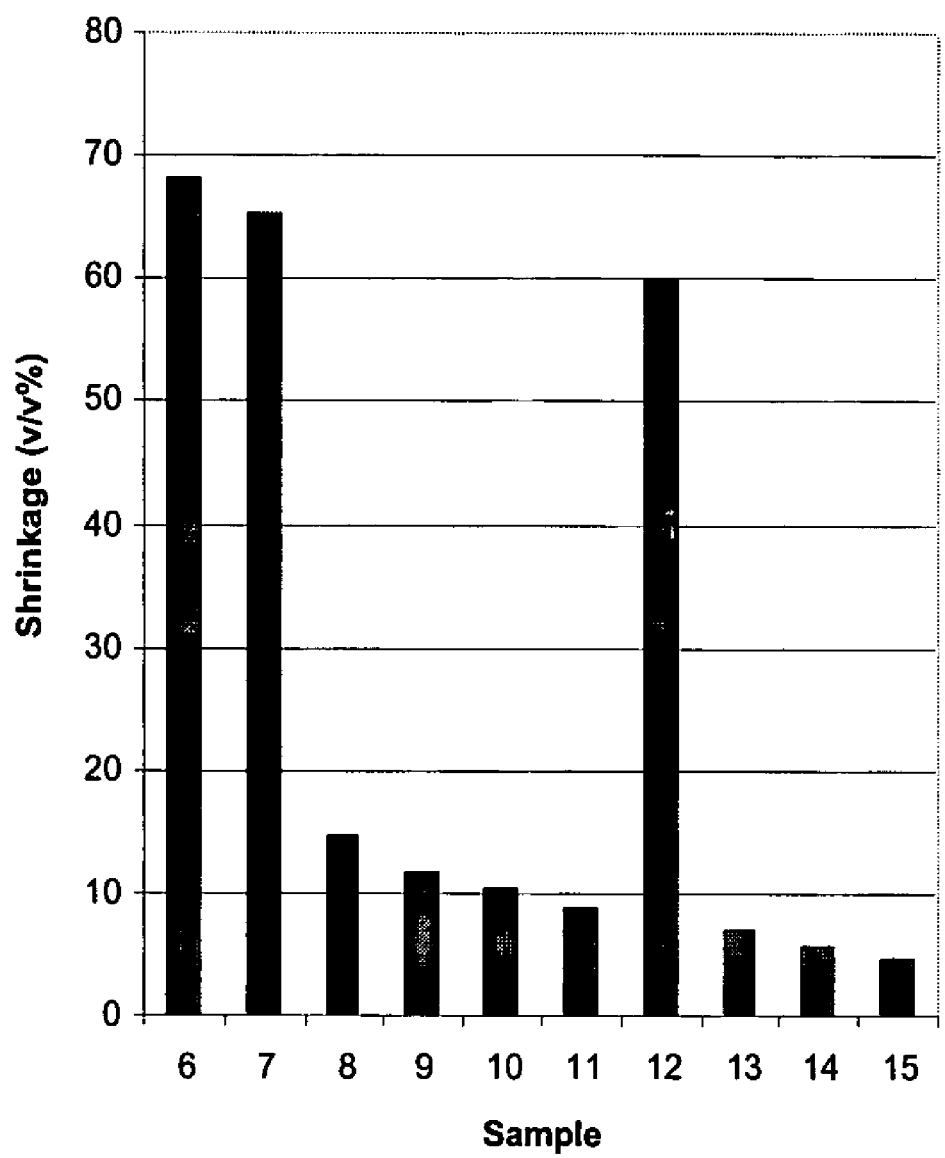
FIG. 5 is a bar graph showing the shrinkage data for samples 6-15 over 45 days.
Figure 6:
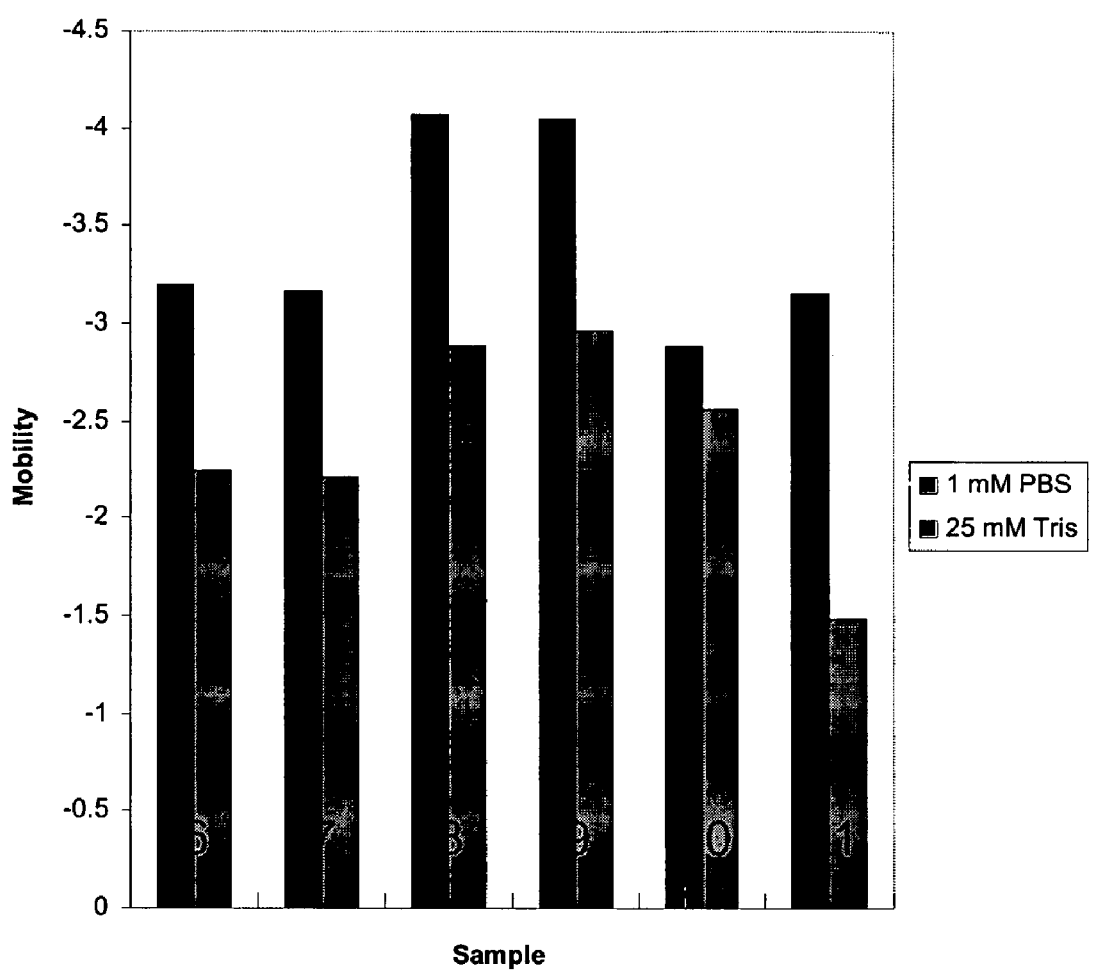
FIG. 6 is a bar graph showing the mobility measurements of crushed particles from samples 6 to 11.

All of the following samples were treated in the following way after gelation:

Fresh sol-gels were aged in a closed container at 5° C. for 20 h, then further aged at room temperature for 7 or 20 days. Aged hydrogels were washed with water 5×5 mL. This was done by soaking the whole aged gel (1 mL initial volume) in 5 mL water at room temperature for 4 h. The water was replaced 4 times, the last time the gel was kept over 8 h, for a total of 24 h. The gels were then allowed to dry at room temperature in a opened container for 45 days. Shrinkage was recorded against the initial volumes of the sample sols. The results are shown in FIG. 5.

(a) Sample 6. To a solution of DGS (240 mg, 1.1 mmol) in H$_2$O (0.50 mL) was added Tris buffer (0.50 mL, 50 mM, pH=8.4). The mixture left at room temperature to gel (Table 1). The hydrogel was then aged at 5° C. for 20 h in a closed container, then further aged and dried in air at room temperature for 6 days. The gel was washed with water, and then allowed to dry at room temperature in an open container for 45 days. Shrinkage was then recorded. Freeze drying gave a colorless solid.

(b) Sample 7. To a solution of DGS (240 mg, 1.1 mmol) in H$_2$O (0.50 mL) was added sorbitol (60 mg, 0.33 mmol in 0.50 mL (50 mM, pH=8.4) Tris Buffer). The mixture was left at room temperature to gel (Table 1). The hydrogel was aged at 4° C. for 20 h in a closed container, then further aged and dried in air at room temperature for 6 days. The gel was washed with water and then allowed to dry at room temperature in an open container for 45 days. Shrinkage was then recorded. Freeze drying gave a white powder.

(c) Samples 8-15: Prepared in a similar manner. The reaction conditions are listed in Table 1.

Example 5

Mobility Measurement

Zeta Potential

After freeze drying, samples 6-11 were ground into powder. Colloidal dispersions were made by adding silica powder to Tris buffer solution (as shown in Table), which were transferred to a cuvette for mobility measurement.

Instrument parameters: wavelength=661.0 nm; field frequency=5.00 Hz; voltage=10.00 volts; electric field=25.45 V/cm. Results are shown in Table 3.

Example 6

Shrinkage and Swelling

The change in volume from the original sol volume of the samples over 45 days was measured on a volume/volume % basis. The results are shown in FIG. 5.

Materials and Methods for Examples 7-18

DGS was synthesized using methods previously reported.[6] The poly(ethylene oxide) (PEO) used was provided by Aldrich and had an average MW of ca. 10,000 and 100,000, respectively. Poly(N-isopropyl acrylamide) (pNIPAM) was provided by Polysciences, Inc. and had a molecular weight of 17,000 and 65,000 poly(ethylene glycol) terminated by amino groups (PEG-NH$_2$) was provided by Nektar Therapeutics with molecular weight of 3400. Poly(propylene glycol)bis(2-amino-propyl ether) was provided by Aldrich and had a molecular weight of 230 and 400, respectively. The molecular weight determined by GPC was 104,000 (Mn, with polystyrene as calibrant). Human serum albumin (HSA) was obtained from Sigma and was fluorescently labeled with FITC as previously described.[39,51] Human serum album (HSA), lysozyme and a Lowry protein assay kit (P5656) were also provided by Sigma.

DSC

The differential scanning calorimeter (DSC) analysis was carried out on a TA 2100 Modulated Differential Scanning Calorimeter at a heating rate of 15° C./min under nitrogen atmosphere.

TGA

Thermogravimetric analysis was performed using a THERMOWAAGE STA409. The analysis was measured under air, with flow rate of 50 cc/min. The heat rate was 5° C./min starting at room temperature.

Porosity BET

The surface area, pore volume and pore radius were measured with an Autosorb 1 machine from Quantachrome. The samples were evacuated to 100 millitorr before heating. The vacuum was maintained during the outgassing at 200° C. with a final vacuum on the order of 10 millitorr (or less) at completion of the outgassing. The samples were backfilled with nitrogen for removal from the outgas station and prior to analysis. BET surface area was calculated by BET (Brunauer, Emmett and Teller) equation; the pore size distribution and pore radius nitrogen adsorption-desorption isotherms was calculated by BJH (Barrett, Joyner and Halenda) method. All the data were calculated by the software provided with the instruments.

Electron Microscopes

The sample was observed by JEOL 840 Scanning Electron Microscopy (SEM) and JEOL Transmission Electron Microscope.

Confocal Microscopy Images to Examine HSA within the Gels

Gels entrapped with FITC-labeled HSA solution were made in vials and Petri dishes. After washing, very thin films of the gels were used for confocal microscopy to examine the areas of labeled HSA within the gels. The images were taken with a Zeiss LSM 510 Confocal Microscope

UV-Visible Spectrophotometer

A gel was prepared with DGS/PEO/FITC-labeled HSA as described above. The gel was washed with 0.05 M NaHCO$_3$ and the washings were examined by a Cary 400 Bio UV-visible Spectrophotometer after centrifugation to get rid of the (gel) particulate.

Example 7

Preparation of DGS Gel

DGS (0.50 g, 2.40 mmol) was dissolved into water (500 L, 27.8 mmol) with sonication at 0° C. until it completely dissolved. TRIS buffer (500 L, 10-50 mM, pH=8.35) was added. The time when the solution lost its ability to flow was recorded as gel time ($t_{gel}$).

Example 8

Preparation of DGS/PEO Gel

PEO (MW=100,000) was dissolved into TRIS buffer (1.0 mL, 10-50 mM, pH=8.35); solutions of different concentrations were prepared. DGS (0.50 g, 2.40 mmol) was dissolved into water (500 L, 27.8 mmol), and sonicated at 0° C. until it totally dissolved. The PEO solution (500 L) was added. Macroporous gels arose when PEO solutions of concentration 0.01-0.08 g/mL were used to make the sol. The time required for the solution to become totally opaque was recorded as phase separation time ($t_{ps}$), and the time when the opaque phase lost its ability to flow was recorded as gel time ($t_{gel}$) (Table 1). After gelation, the gel was soaked in water (5 mL) for 12 h and then stored in fresh water or allowed to dry in air at room temperature. BET data is provided in Table 10. FIG. 7 provides a graph showing the gel time of DGS doped with different concentrations of PEO prepared in an analogous manner as described in this example.

Example 9

Preparation of DGS/PEO/PPG-NH$_2$ Gel 0.5 g PEO (MW=10,000) was dissolved into phosphate buffer (1.0 mL, 5-10 mM, pH=7.5-8.5); 0.5 g PPG-NH$_2$ (MW=230) was dissolved into phosphate buffer (1.0 mL, 5 mM, pH=7.5); solutions of different ratio of PEO/PPG-NH$_2$ were prepared (see Table 9). DGS (0.50 g, 2.40 mmol) was dissolved into water (500 L, 27.8 mmol), and sonicated at 0° C. until it totally dissolved. 200 L DGS solution was added with 60 L PEO/PPG-NH$_2$ solution. The time required for the solution to become totally opaque was recorded as phase separation time ($t_{ps}$), and the time when the opaque phase lost its ability to flow was recorded as gel time ($t_{gel}$) (Tables 1 and 10). After gelation, the gel was soaked in water (5 mL) for 12 h and then stored in fresh water or allowed to dry in air at room temperature

Example 10

Preparation of DGS/polyNIPAM Gel polyNIPAM was dissolved into water (50 mg NIPAM/ 1000 L H$_2$O). DGS (0.50 g, 2.40 mmol) was dissolved into water (500 L, 27.8 mmol) with sonication at 0° C. until it was totally dissolved. The polyNIPAM solution (500 L) was then added, and the solution mixed thoroughly to give a sol containing 0.025 g/mL of polyNIPAM. After gelation, the gel was soaked in water (10 mL) for 12 h and then stored in fresh water or allowed to dry in air at room temperature.

Example 11

Preparation of DGS/PEO-NH$_2$ and DGS/PEO/PPG-NH$_2$

PEO-NH$_2$ (MW=3,400) was dissolved into Phosphate buffer (1.0 mL, 5-50 mM, pH 7-8.5); solutions of different concentrations were prepared. DGS (0.50 g, 2.40 mmol) was dissolved into water (500 μL, 27.8 mmol), and sonicated at 0° C. until it totally dissolved. The PEO-NH$_2$ solution (500 μL) was added. Macroporous gels arose when PEO-NH$_2$ solutions of concentration larger than 0.05 g/mL were used to make the sol. The time required for the solution to become totally opaque was recorded as phase separation time ($t_{ps}$), and the time when the opaque phase lost its ability to flow was recorded as gel time ($t_{gel}$). After gelation, the gel was soaked in water (5 mL) for 12 h and then stored in fresh water or allowed to dry in air at room temperature.

A similar process was used to prepare gels doped with both PEO and PPG-NH$_2$. Several stock aqueous solutions of PEO and PPG-NH$_2$ were prepared (Table 9). DGS (1.001 g) was dissolved in DGS dissolved in distilled water (1 mL) with sonication over about 20 minutes. To the DGS solution (200 μl) was added the Polymer Mixture with stirring. The sol was then allowed to gel (Table 10).

Example 12

Gels with Entrapped Protein

These gels were prepared as described in Examples 8, 10-12 except that the protein (HSA) was dissolved into the polymer/buffer solution prior to addition to the DGS solution (10 mg HSA/1000 L solution, i.e. 0.5 g DGS, 5 mg HSA, 25 mg PEO, 1000 L water).

Example 13

Calculating the Amount of PEO Left in Gels After Washing Using Thermogravimetric Analysis DGS and DGS/PEO monoliths were formed by pouring off the excess liquid after phase separation and gelation had occurred. The gels were washed 3 times by soaking in water, each time with 20 mL water, for 1 day. The gels could be washed as a monolith, or after crushing to give comparable results. The washed gels were dried in open air for 2 days, then freeze-dried for more than one day. The sample was first exposed to vacuum in a flask cooled with dry ice and then at RT. Graphs indicate there is roughly 24% PEO left in the gels after washing (FIG. 10).

Example 14

Figure 11:
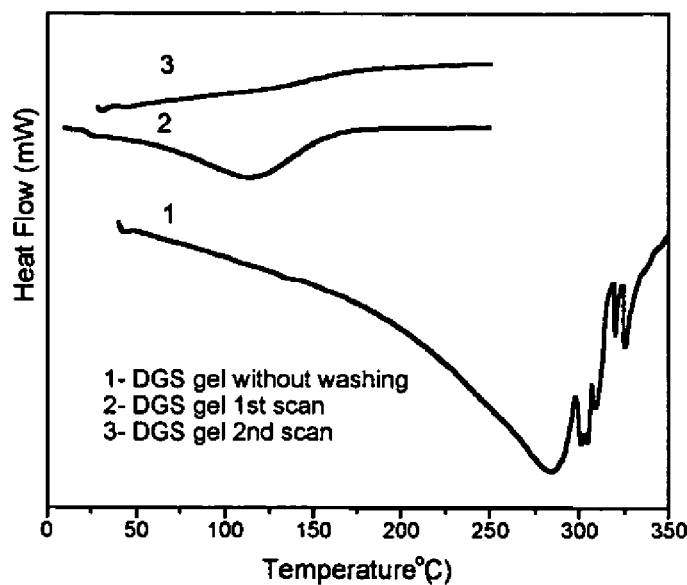
FIG. 11 shows DSC of silica derived from: A: DGS; B: DGS+100000 MW PEO.
Figure 11:
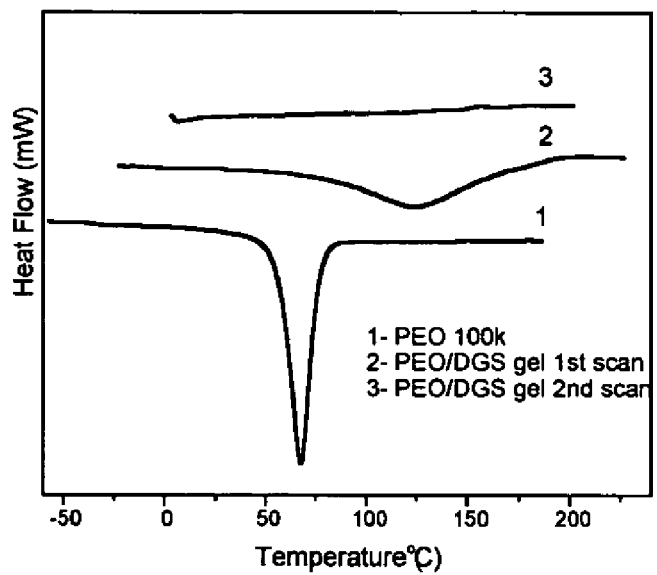

Finding the Structure of PEO when in Gels by Usage of a Differential Scanning Calorimeter DSC was used to measure the thermal properties and structures of the DGS and DGS/PEO gel (FIG. 11).

Example 15

Confocal Microscopy Images to Examine HSA within the Gels

Gels prepared from DGS (0.5 g), water (0.5 mL), and PEO (0.5 mL of a 0.05 g PEO/1 mL buffer (10 mM Tris buffer) solution) and FITC-labelled HSA solution consisting of 0.750 mL PEO and 0.250 mL labeled HSA) were made in vials and in Petri dishes. After washing, the location of labeled HSA within the gels was determined, in very thin films of the gels prepared using a razor blade, by confocal microscopy (FIG. 14).

Example 16

Preparation of Gels for Bet Analysis

Two gels prepared from TEOS (0.5 g), aqueous HCl (pH 1.6, 0.5 mL of 0.024 M solution) and Tris buffer (0.5 mL, pH=8.25) were made for BET analysis with gel times of 6.5 and 6 minutes, respectively.

Gels prepared from DGS (0.5 g), water (0.5 mL) and PEO (MW 100,000, 0.5 mL of a 0.05 g/mL solution) were also made for BET analysis with phase separation times of 3 minutes and gelation times of 7 minutes, respectively.

Example 17

Testing loss of HSA from Gels with UV-Visible Spectrophotometer

A gel was prepared with DGS/PEO/FITC-labeled HSA as described above (i.e. 0.5 g DGS, 500 L H 20, 750 L PEO solution [50 mg PEO Mw 100000/1000 L 10 mM Tris buffer solution], 1000 L FITC labeled HSA solution [10 mg HSA/1000 L 10 mM Tris buffer solution]). It phase separated at 1.5 min and gelled at 3 min. The gel was washed 3 times with 20 mL 0.05 M NaHCO$_3$, each time for 24 h, and the washings were tested using UV spectroscopy. The intensity of the peaks due to the FITC label on the HSA peaks became much smaller with each subsequent washing. However, the washings were contaminated with particles, which reduced the sensitivity of the method. Therefore, the Lowry Method of protein detection was also used.[52] Fluorescein isothiocyanate (FITC, Aldrich) was used to label the proteins. Labeling was carried out in pH 9.5 carbonate buffer (0.05 M) for 2 h at 5° C. Dilutions of HSA with PEO and HSA with Tris buffer were made to form an HSA standard curve using fluorescein). The first set of gels contained 0.5 g DGS in 0.5 mL water, and 0.5 mL of an HSA/PEO solution of 10 mg HSA and 1 mL varying concentrations of PEO (MW 100,000). The gels were washed (with water) on the day of gel preparation (1$^{st}$ washing), the day after gel preparation (2$^{nd}$ washing), and the 4$^{th}$ day after gel preparation (3$^{rd}$ washing). The protein content of the washings was determined using the Lowry method as described below.

Determination of protein concentration by Lowry method:

5.0-10.0 mg of protein was entrapped within gels prepared with 0.5 g DGS. After gelation, 20 ml 5-10 mM phosphate buffer were added three times, soaking the gel. The buffer is changed every 24 hours. All the washings and gels were kept at 4° C. in a refrigerator. The washings were measured by Lowry method with the reagents proved from Sigma (Sigma Protein Assay Kit, procedure No. P5656). The standard curves were plotted using HSA, BSA and lysozyme as standards respectively. The measurements were performed in 96-well plates using a TECAN Safire absorbance/fluorescence plate reader operated in absorbance mode at 750 nm.

These data are reported in Tables 7 and 8 HSA and lysozyme respectively, where it is evident that more protein was washed out when the PEO concentration is high and that PPG-NH$_2$ is much more efficient and retaining proteins than other polymers.

Examples 18-20

Specific Application of the Silica Materials of the Invention to Bioaffinity Chromatography (FAC/MS)

Materials and Methods for Examples 18-20

Chemicals

Tetraethylorthosilicate (TEOS, 99.999%), dimethyldimethoxysilane (DMDMS, 98%) and 3-aminopropyltriethoxysilane (APTES) were obtained from Aldrich (Oakville, ON). Diglycerylsilane precursors were prepared from TEOS as described below. Human serum albumin (HSA), trimethoprim, pyrimethamine, dihydrofolic acid (DHF), reduced nicotinamide adenine dinucleotide phosphate (NADPH), folic acid, dithiothreitol (DTT) poly(ethyleneglycol) (PEG/PEO, MW 2 kDa to 100 kDa) poly(allylamine) (MW 17 kDa) and fluorescein were obtained from Sigma (Oakville, ON). Coumarin and 5-(and -6) carboxyfluorescein, succinimidyl ester were obtained from Molecular Probes Inc. (Eugene, Oreg.). Recombinant dihydrofolate reductase (from *E. coli*), which was affinity purified on a methotrexate column, was provided by Professor Eric Brown (McMaster University).[53] Fused silica capillary tubing (150-250 μm i.d., 360 μm outer diameter, polyimide coated) was obtained from Polymicro Technologies (Phoenix, Ariz.). All water was distilled and deionized using a Milli-Q synthesis A10 water purification system. All other reagents were of analytical grade and were used as received.

Preparation of DGS

TEOS was distilled to remove any residual water and a neat mixture of the anhydrous TEOS (2.08 g, 10.0 mmol) and anhydrous glycerol (1.84 g, 20.0 mmol) was heated at 130° C. for 36 h, during which time EtOH was distilled off. Complete removal of EtOH and unreacted starting materials at 140° C. in vacuo gave DGS as a solid compound that was not contaminated with residual ethanol.

Preparation of Columns

Prior to loading columns the inner surface of the fused silica capillary was coated with APTES to promote electrostatic binding of the monolithic silica column. The capillary was first washed with 3-4 volumes of: 1 M NaOH; H$_2$O; 1 M HCl; H$_2$O and EtOH. At this point, 1 mL of 2% (v/v) APTES in absolute EtOH was loaded into the column and left to react for 12 hr at 110° C., after which the excess APTES was washed out with water and the capillary was dried for 12 hr at 110° C.

Silica sols were prepared by first mixing 1 g of DGS (finely ground solid) with 990 μL of H$_2$O and, optionally, 10 μL of 1 M HCl to yield ~1.5 mL of hydrolyzed DGS, after 15-25 min of sonication. The hydrolyzed DGS was filtered through a 0.45 μm syringe to remove particulates before use. A second aqueous solution of 50 mM HEPES at pH 7.5 was prepared containing 16% (w/v) PEO (MW=10 kDa) and 0.6% (v/v) APTES. This aqueous solution also contained ca. 20 μM of DHFR. 100 μL of the Buffer/PEG/APTES/DHFR solution was mixed with 100 μL of hydrolyzed DGS and the mixture was immediately loaded via syringe pump into a fused silica capillary (ca. 2 m long, 150-250 μm i.d.). The final composition was of the solution was 8% w/v PEO (10 kDa), 0.3% v/v APTES and 10 μM DHFR in 25 mM HEPES buffer. The mixture became cloudy due to spinodal decomposition (phase separation) over a period of 1-3 sec about 2-3 min after silica polymerization (~10 min) to generate a hydrated macroporous monolithic column containing entrapped protein. Phase separation was easily visualized by eye, while gelation time was determined by measuring the loss of flow of the material. After loading of the sol-gel mixture, the monolithic columns were aged for a minimum of 5 days at 4° C. and then cut into 10 cm lengths before use. In some cases, a final concentration of either 0.03% polyallylamine (PAM, MW 17,000) or 0.3% dimethyldimethoxysilane (DMDMS) was added to the columns instead of APTES to examine the effects of surface derivatization on non-selective retention.

Characterization of Silica Morphology

The morphology of the column was assessed using nitrogen adsorption porosimetry (for characterization of mesopores) or mercury intrusion porosimetry and scanning electron microscopy (SEM) for characterization of macropores. Nitrogen porosimetry of completely dried monoliths was performed on a Quantachrome Autosorb-1 surface area/pore-size analyzer. Before analysis, the monoliths were washed copiously to remove any entrapped glycerol, were crushed to a fine powder, freeze-dried and outgassed at 120° C. for 4 hours to remove air and bound water from the surface of the powder. The pressure was measured as nitrogen was adsorbed and desorbed at a constant temperature of −196° C. Using the desorption branch of the resulting isotherm, the average pore-size and distribution of pore-sizes was determined using the BJH (Barrett, Joyner and Halenda) calculation.[54] Samples were prepared in an identical manner for Hg intrusion porosimetry, and were measured using a Quantachrome PoreMaster 60 instrument. The contact angle used was 140°. Both high and low pressure data were obtained on the same sample, covering the pressure range from 0.8 psia to 59,658 psia (265.5 μm to 3.58 nm pore diameter range). SEM analysis was done by cutting the capillary to expose a fresh surface, which was then coated with a gold film under vacuum to improve conductivity. Imaging was performed at 10 kV using a JEOL 840 Scanning Electron Microscope.

FAC/MS Studies

Figure 15:
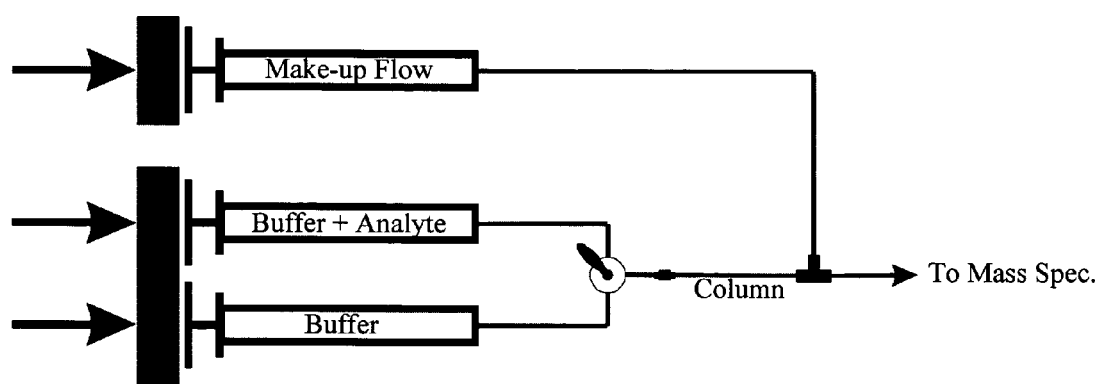
FIG. 15 shows a schematic of the apparatus used for FAC/MS. A switch valve is used to switch from buffer to buffer+analyte, allowing continuous infusion of analytes onto the column. The column outlet is connected to a mixing tee for addition of makeup buffer that flows directly into the PE/Sciex API 3000 triple-quadrupole mass spectrometer.

The frontal affinity chromatography system/mass spectrometer system is shown in FIG. 15. Syringe pumps (Harvard Instruments Model 22) were used to deliver solutions, and a flow-switching valve was used to toggle between the assay buffer and the solution containing the compound mixture. This solution was then pumped through the column to achieve equilibrium. Effluent was combined with suitable organic modifiers to assist in the generation of a stable electrospray and detectability of the sprayed components using a triple-quadrupole MS system (PE/Sciex API 3000). This configuration allows for maximum flexibility in compound introduction. Full operation of FAC/MS methods requires frequent flow switching between two solutions connected to the head of the column. An Upchurch microinjection valve allows syringe contents to be exchanged during operation. Columns were interfaced to the FAC system using Luer-capillary adapters (Luer Adapter, Ferrule and Green Microtight Sleeve from Upchurch (P-659, M-100, F-185X)). All other connections between components were achieved using fused silica tubing.

Typical FAC/MS experiments involved infusion of mixtures of compounds containing 1-200 nM of each compound, including coumarin and fluorescein as void markers, folic acid (micromolar substrate) and pyrimethamine and trimethoprim (nM inhibitors). Before the first run, the column was flushed with 0.05 M $NH_4OAc$ buffer (pH 6.6, 100 mM NaCl) for 30 min at different flow rates (from 1 to 5 L.min$^{-1}$) to remove any glycerol and non-entrapped protein and then equilibrated with 2 mM $NH_4OAc$ for 30 min at different flow rates (from 1 to 5 L.min$^{-1}$). All compounds tested were present in 2 mM $NH_4OAc$ and were delivered at a rate of 5 L.min$^{-1}$ using the syringe pump. The makeup flow (used to assist in the generation of a stable electrospray) consisted of methanol containing 10% (v/v) $NH_4OAc$ buffer (2 mM) and was delivered at 5 L.min$^{-1}$, resulting in a total flowrate of 10 μL.min$^{-1}$ entering the mass spectrometer. The mass spectrometer was operated in multiple reaction monitoring (MRM) mode with simultaneous detection of m/z 147 to m/z 103 (coumarin); m/z 249 to m/z 177 (pyrimethamine); m/z 291 to m/z 230 (trimethoprim); m/z 333 to m/z 287 (fluorescein) and m/z 442 to m/z 295 (folic acid).

Characterization of Column Performance

Columns of 10 cm length were prepared containing no protein (blanks); initial loadings of 50 pmol active DHFR; or 50 pmol of DHFR that was partially denatured by boiling prior to use or 50 pmol of HSA (selectivity control). In all cases FAC/MS measurements were performed using the five compound mixture described above and the resulting frontal chromatograms were used to evaluate non-selective interactions of compounds with the column, the reversibility of binding, the potential for regeneration of columns and the level of leaching of entrapped protein.

Columns that contained active DHFR were further characterized by monitoring the breakthrough volume (obtained by multiplying flowrate by breakthrough time) as a function of analyte concentration using either pyrimethamine or trimethoprim. In each case, the data were fit to the following equation:[17a]

$$V = V_0 + \frac{B_t}{[A] + K_d} \quad (1)$$

where $V_0$ is the void volume (μL), V is the retention volume (μL), [A] is the analyte concentration (μM), $K_d$ is the binding constant of the ligand to the protein (μM) and $B_t$ is the total picomoles of active protein in the column, based on one active site per enzyme molecule.

Characterization of Protein Leaching

DHFR was fluorescently labeled using 5-(and -6) carboxyfluorescein, succinimidyl ester. A reaction mixture containing 0.58 mM DHFR, 1.9 mM 5-(and -6) carboxyfluorescein, succinimidyl ester and 150 mM sodium bicarbonate was incubated at room temperature for 2 hours. The mixture was then exhaustively dialyzed at 4 EC against 25 mM HEPES (pH=7.5, 5×1000-fold excess over a 40 hour period) to remove unbound fluorescein. Columns containing fluorescently-labeled DHFR were prepared as described above. The running buffer used for FAC/MS was passed through the column at a flow rate of 5 uL.min$^{-1}$ and fractions were collected over a period of 1 hr for 8 hours. The fluorescence emission intensity of each fraction was compared to a standard curve of emission intensity vs. concentration of fluorescently-labeled DHFR stock to determine the concentration of DHFR present in the eluted buffer. After the 8 hour elution experiment the monolith was dissolved by infusing 25 μL of 1 M NaOH. The column contents were then neutralized with 1 M Tris.HCl, pH 8.3 and the emission intensity was compared to a calibration curve to determine the concentration of DHFR remaining in the column. All fluorescence measurements were made using a Tecan Saphire microplate reader operated in top-read mode using an excitation wavelength of 488 nm, an emission wavelength of 515 nm with 5 nm bandpasses in both the excitation and emission paths.

DHFR Stability in 2 mM Ammonium Acetate

DHFR was diluted to 40 nM in 2 mM ammonium acetate, (which therefore contained 3 μM HEPES and 2 μM NaCl) and was incubated for 8 hours. At 1 hour intervals 100 μL aliquots were mixed with 100 μL of a solution containing 50 mM Tris.HCl pH=7.5, 2 mM DTT, 100 μM NADPH and 100 μM DHF. DHFR activity was measured by monitoring the decrease in absorbance at 340 nm using a Tecan Saphire microplate reader. Activity data is reported relative to the activity obtained from a DHFR sample that was diluted in 50 mM Tris.HCl, pH 7.5, containing 2 mM DTT.

Example 18

Column Formation and Optimization

It was desirable that the bioaffinity columns be fabricated using protein-compatible processes, thus several issues were addressed to produce a viable monolithic bioaffinity column. Goals to achieve when developing monolithic bioaffinity columns were: 1) to produce a biocompatible column matrix that entrapped biomolecules in an active form; 2) to have spinodal composition occur after column loading but before gelation of the silica phase to promote macroporosity; 3) to avoid shrinkage and cracking of the column, which would introduce unwanted flow channels; 4) to minimize protein leaching after gelation of the silica, and; 5) to minimize non-selective interactions between small molecules and the silica matrix. A variety of parameters were optimized to achieve this goal, including the silica precursor (TEOS vs. DGS), silica concentration (1-10 mol %), gelation pH (5 to 8), ionic strength (0 to 100 mM), and PEO concentration (2-12% w/v) and molecular weight (2 kDa-100 kDa). While several compositions produced viable columns, the best performance was obtained using a composition derived from the protein compatible precursor DGS which contained an initial level of 3.3 mol % $SiO_2$. Lower levels led to columns that would slowly dissolve in the mobile phase, while higher levels gelled too quickly to allow facile column loading. Optimal gelation conditions were achieved under mild conditions at 4° C., pH 7 with an ionic strength of 25 mM. Macroporosity could be obtained using a variety of PEO concentrations and molecular weights (see below), however, columns that contained 8% w/v of 10 kDa PEO were selected. Phase separation occurred for molecular weight values of 10 kDa or higher, and at levels of 2% w/v or higher for 10 kDa or higher molecular weight PEO. An optimal level of 8% w/v for 10K PEO was selected owing to the good homogeneity and reproducibility obtained for forming columns using this composition, and because higher levels or molecular weights of PEO produced solutions that were too viscous to allow facile loading of the column.

Early versions of columns used untreated, NaOH, methacryloxypropyl-trimethoxysilane or 3-glycidoxypropyltrimethoxysilane-treated capillaries as supports. However, it was often observed that the monolith could be pushed out of the capillary at higher flow rates. To overcome this problem the inner surface of the capillary was pretreated with APTES, which provided electrostatic bonding between the anionic silica monolith and the cationically modified capillary surface. In such columns, flow rates as high as 500 µL.min$^{-1}$ could be achieved with no occurrences of monolith detachment from the capillary.

Example 19

Column Characterization

Figure 16:
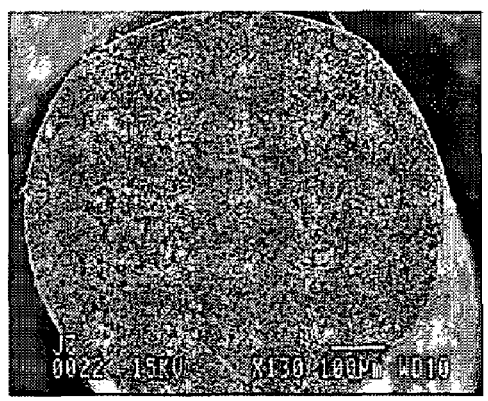
FIG. 16 shows SEM images of a sol-gel derived column containing DGS/PEO/APTES after 5 days of aging. Panel A: image of monoliths formed in 1 mm capillaries that pulled away from the capillary wall and were removed from the capillary under flow; Panel B: magnified image of a monolith in a 250 μm capillary showing the meso and macro pore distribution within the sol-gel derived monolith.
Figure 16:
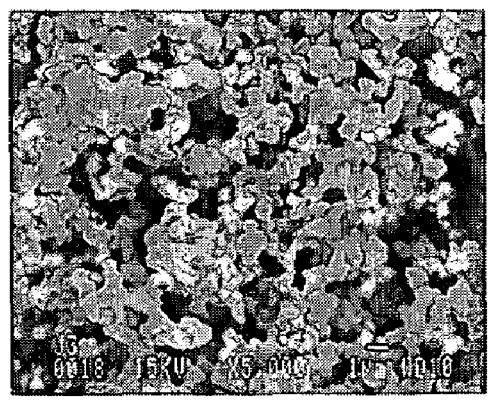

FIG. 16 shows scanning electron microscopy images of the DGS/PEO/APTES monolithic silica stationary phase. Panel A shows an image of a 1.0 mm diameter column that had been extruded from an uncoated capillary, and shows that the silica forms a self-supporting monolith. Panel B shows a high magnification image of a monolith within a 250 µm capillary, showing the macroporous nature of the silica skeleton. The silica matrix appears to be composed primarily of silica beads that are 1-2 µm in diameter and are linked together to form a continuous monolith. The voids (through-pore spaces) are on the order of a microns in diameter (see mercury intrusion porosimetry data below), and provide sufficient void volume to allow good flow of liquids with low backpressure. Overall, the macroporous morphology of the columns appears to be quite similar to that reported by Tanaka for reversed phase columns (skeleton size of 1-2 µm, through-pore diameter of 2-8 µm$^{10a}$), although it is important to note that in the case of Tanaka's columns the PEO was removed by pyrolysis before imaging.

Figure 17:
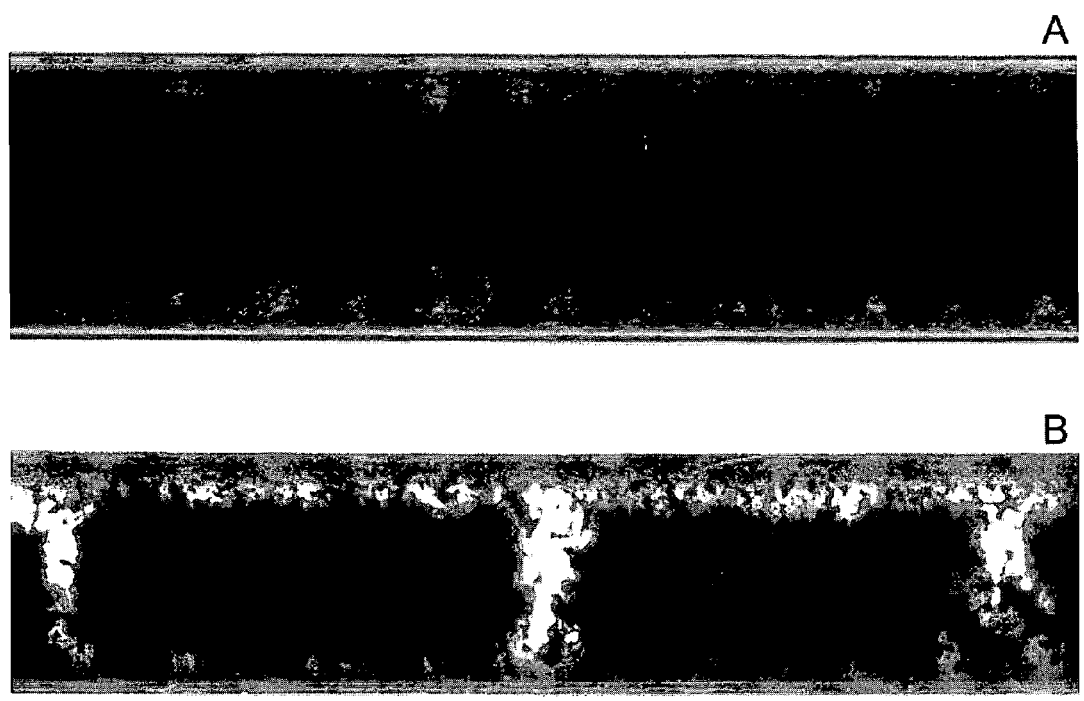
FIG. 17 shows brightfield images of a filled capillary (250 μg/m i.d.) after 3 months of aging in buffer (Panel A), and after 24 hours of storage in a dessicator (Panel B).

Attempts to image monoliths within 150-250 µm i.d. capillary columns via SEM showed that the introduction of the columns to ultrahigh vacuum (UHV) produced pullaway of the monolith from the capillary wall. To avoid UHV, the monoliths were imaged using brightfield microscopy. FIG. 17 shows a brightfield image of a filled capillary (250 µm i.d.) after 3 months of aging in buffer (Panel A), and clearly shows that the monolith completely fills the capillary with no pullaway. The lighter areas at the edges of the capillary in this image are due to differences in light diffraction. This was confirmed by testing the flow through 3 month old columns, which was identical to that obtained from fresh columns (data not shown). Panel B shows the same monolith after 24 hrs of storage in a dessicator. Upon removal of entrapped water, the silica monolith shrinks significantly and exhibits cracking and pullaway. These results show that columns should be stored in a wet state to maintain column integrity. Such storage conditions are also desirable to maintain the activity of entrapped proteins.

Mercury intrusion porosimetry was done on PEO-doped samples to better assess the nature of the macropores in the various materials. Table 11 shows the data obtained for samples containing 8 wt % of 2 kDa, 10 kDa and 100 kDa PEO. While all materials contained macropores, the size and proportion of macropores was highly dependent on the molecular weight of the PEO used. For 2 kDa PEO doped samples, only 5% of the pore volume was occupied by macropores with an average diameter of 1.2 µm. Columns formed from such materials did not show good flow properties, and thus were not examined further. Samples containing 10 kDa PEO (which were used for subsequent FAC/MS studies described below) had a much higher proportion of macropores (23%) with an average pore diameter of ~0.5 µm. Increasing the molecular weight of PEO to 100 kDa led to a similar proportion of macropores (20%), but in this case the average macropore diameter was much higher than was observed with 10 kDa PEO (almost 3 µm). While such materials led to columns that showed good flow properties, the material underwent phase separation and gelation rapidly, which made it difficult to reproducibly fill the columns.

BET measurements were performed on PEO-doped samples to assess the morphology of the mesopores within the silica skeleton (note: measurements were done only for samples that were not pyrolyzed). Table 12 shows the mean pore diameter, surface area and volume occupied by mesopores within the column. Although the drying process decreases pore diameters by a factor of ca. 10-fold,[55] the differences in the pore sizes of the dried samples are likely to reflect the relative pore size differences in the wet, chromatographic matrix. While PEO is primarily responsible for the formation of macropores in the present materials, it is evident that the addition of 10 kDa PEO, dramatically alters the fraction of mesopores (2-50 nm diameter) relative to micropores (<2 nm) in favor of mesopores, although it leads to only minor decreases in surface area relative to pure DGS. The addition of PEO also produces a higher total pore volume and a slightly larger average mesopore diameter, both of which should result in somewhat better flow properties. When considered together with the SEM and Hg intrusion porosimetry data, it is apparent that the columns have the desired meso/macroporous morphology.

Example 20

Bioaffinity Column Performance

Figure 18:
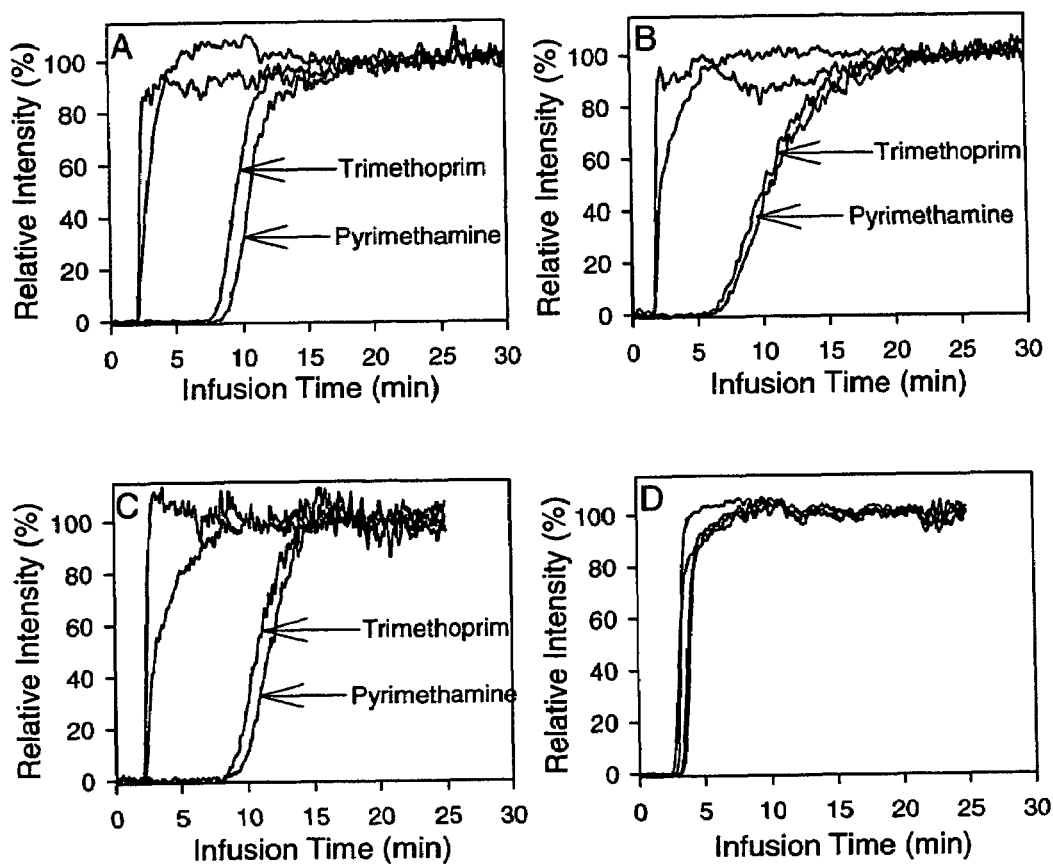
FIG. 18 shows FAC/MS data showing the effects of surface modification on non-selective adsorption. Panel A: unmodified DGS/PEO monoliths; Panel B: DGS/PEO monoliths containing 0.3% w/v DMDMS; Panel C: DGS/PEO monoliths containing 0.03% w/v poly(allylamine) MW 17,000; Panel D: DGS/PEO monoliths containing 0.3% w/v APTES. The order of elution for all chromatographs is: Methotrexate, fluorescein, trimethoprim, pyrimethamine.

A consideration in the development of bioaffinity columns for FAC/MS applications is to minimize non-selective adsorption of analytes to the column matrix while maximizing the retention of compounds owing to selective binding to the entrapped protein. FIG. 18 shows frontal chromatograms of unmodified columns relative to columns containing dimethyldimethoxysilane, aminopropylsilane or poly(allylamine)-derivatized silica. These additives allowed the examination of charged and uncharged additives and to modify the hydrophobicity of the column so as to modulate interactions of analytes with the silica. As shown in Panel A, the unmodified silica has a tendency to retain cationic species (pyrimethamine and trimethoprim) but does not retain either anionic or neutral species. Addition of either DMDMS or PAM did not significantly alter the retention properties, possibly owing to the low levels at which these could be employed before reducing column performance. However, even low levels of APTES led to almost complete removal of interactions between the silica matrix and cationic analytes, while retaining the low degree of non-selective adsorption of anionic and neutral species, in agreement with previous observations by Zusman for sol-gel based glass fiber affinity columns.[34] Higher levels of APTES caused retention of anionic species, and thus 0.3% APTES was found to be optimal for minimizing non-selective retention. Recent studies using time-resolved fluorescence anisotropy to probe adsorption of the charged fluorescent probes onto APTES modified silica surfaces confirms that 0.3% (v/v) APTES effectively creates a zwitterionic surface with no net attraction or repulsion of charged species.[56] This level of APTES is also the maximum amount that can be used before flocculation of sols will occur. Importantly, this surface maintained its ability to block non-selective retention over a period of months, indicating that the APTES formed a stable surface coating that did not change in composition with time.

Figure 19:
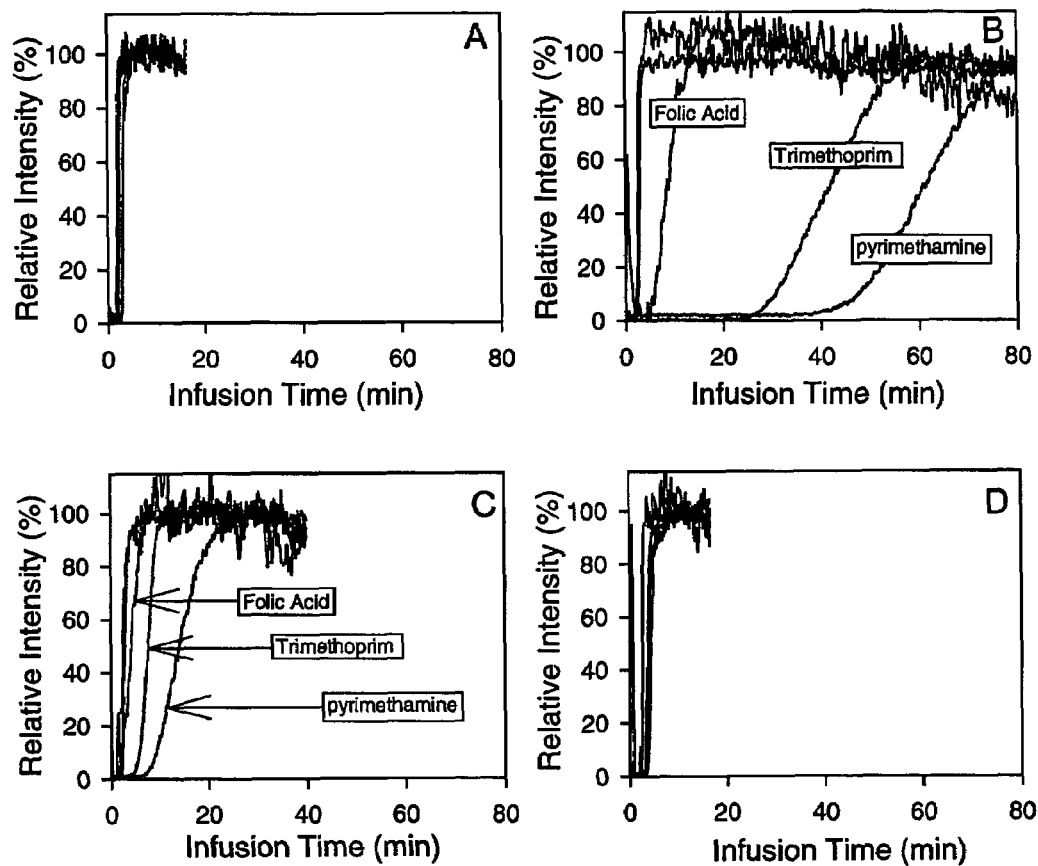
FIG. 19 shows typical FAC/MS traces obtained using protein-loaded and blank DGS/PEO/APTES monolithic columns. Panel A: blank columns containing no protein; Panel B: column containing 50 pmol DHFR (initial loading); Panel C: column containing an initial loading of 50 pmol of heat-denatured DHFR; Panel D: columns containing and initial loading of 50 pmol of HSA. Coumarin, pyrimethamine, trimethoprim and folic acid were infused at 20 nM. Fluorescein was infused at 100 nM. All traces are normalized to the maximum signal obtained after compound breakthrough.

FIG. 19 shows FAC/MS traces obtained for elution of mixtures of DHFR inhibitors and control compounds through DGS/PEO/APTES columns containing no protein, active DHFR, partially denatured DHFR, or HSA, a protein that does not bind DHFR inhibitors. The blank column shows the expected breakthrough of all compounds in the first few minutes, indicative of minimal non-selective interactions, showing that normal-phase silica chromatography had been suppressed. Panel B shows significant retention of the two DHFR inhibitors, trimethoprim ($K_d$=4 nM, elution time of 39 min) and pyrimethamine ($K_d$=45 nM, retention time 55 min), less retention of a weak inhibitor (folic acid, $K_d$=11 μM, retention time=7 min) and no retention of non-selective ligands (fluorescein, coumarin, retention time=2 min). This result indicates that DHFR is active when entrapped in the column, in agreement with recent results from showing good activity of DHFR when entrapped in DGS derived materials.[43] Upon boiling DHFR prior to entrapment, all DHFR-binding ligands show significantly reduced retention times, consistent with partial denaturation of the protein. It should be noted that DHFR is known to be remarkably stable to thermal denaturation, and that thermal unfolding of DHRF is partially reversible.[57] Thus it is not surprising that partial binding affinity is retained even after heat denaturation. As a secondary control, a column containing entrapped HSA was examined. As shown in Panel D there is essentially no binding beyond that obtained in a blank column. Thus, retention of the ligands is a consequence of selective interactions between the ligands and DHFR. The reversal in the expected elution times for trimethoprim and pyrimethamine (based on their respective $K_d$ values) is not fully understood at this time, but may be related to differences in on and off rates, which are likely to play a significant role in determining the overall retention time of compounds on the column.

Figure 20:
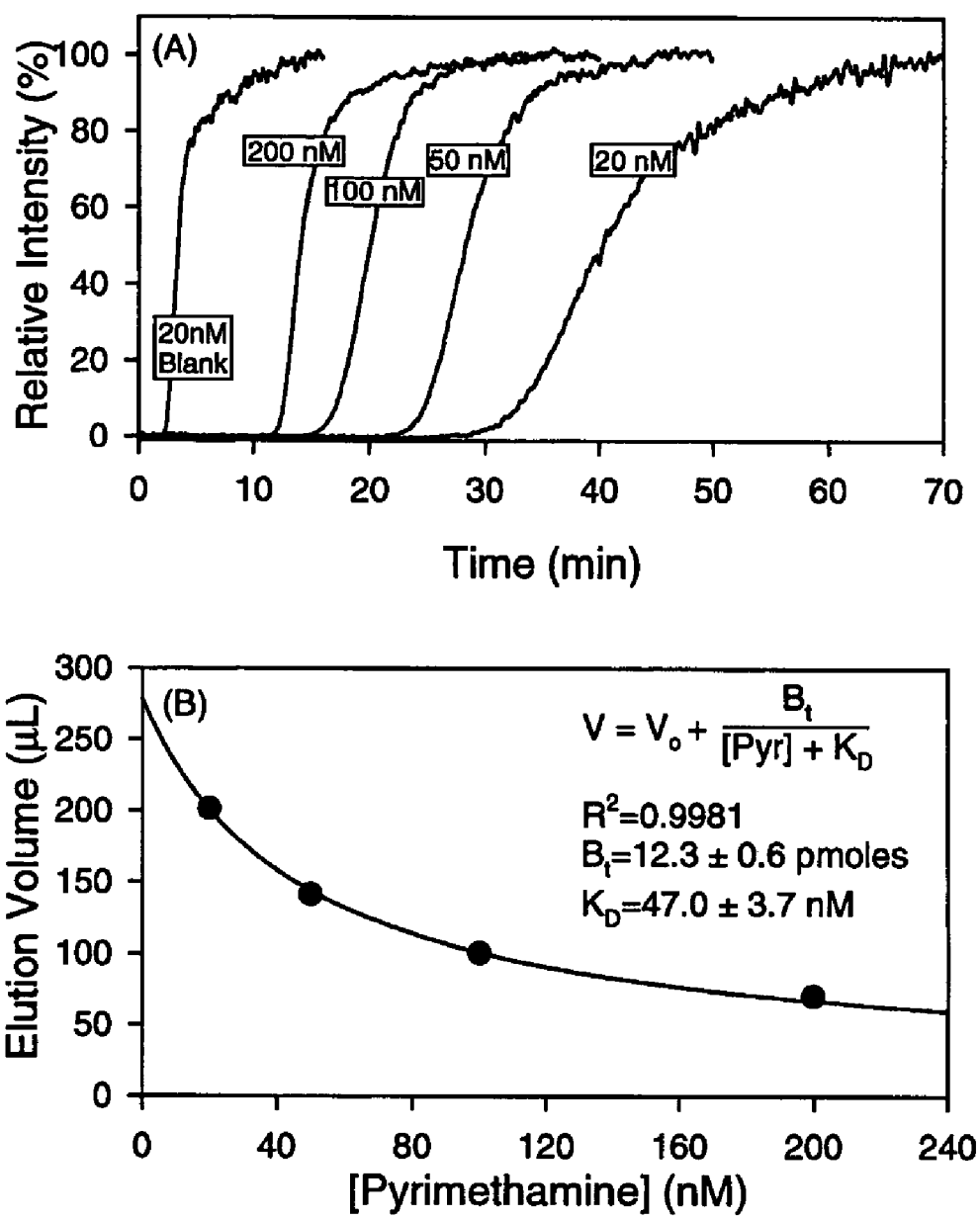
FIG. 20 shows the determination of $K_d$ and $B_t$ values for DHFR columns based on the effect of ligand concentration on breakthrough volume. Panel A: Superimposed FAC/MS traces at 4 different ligand concentrations relative to a blank column; Panel B: Plot of V vs. [A]. Note that the data is obtained from the first run performed on four individual DHFR loaded columns and one blank column.
Figure 21:
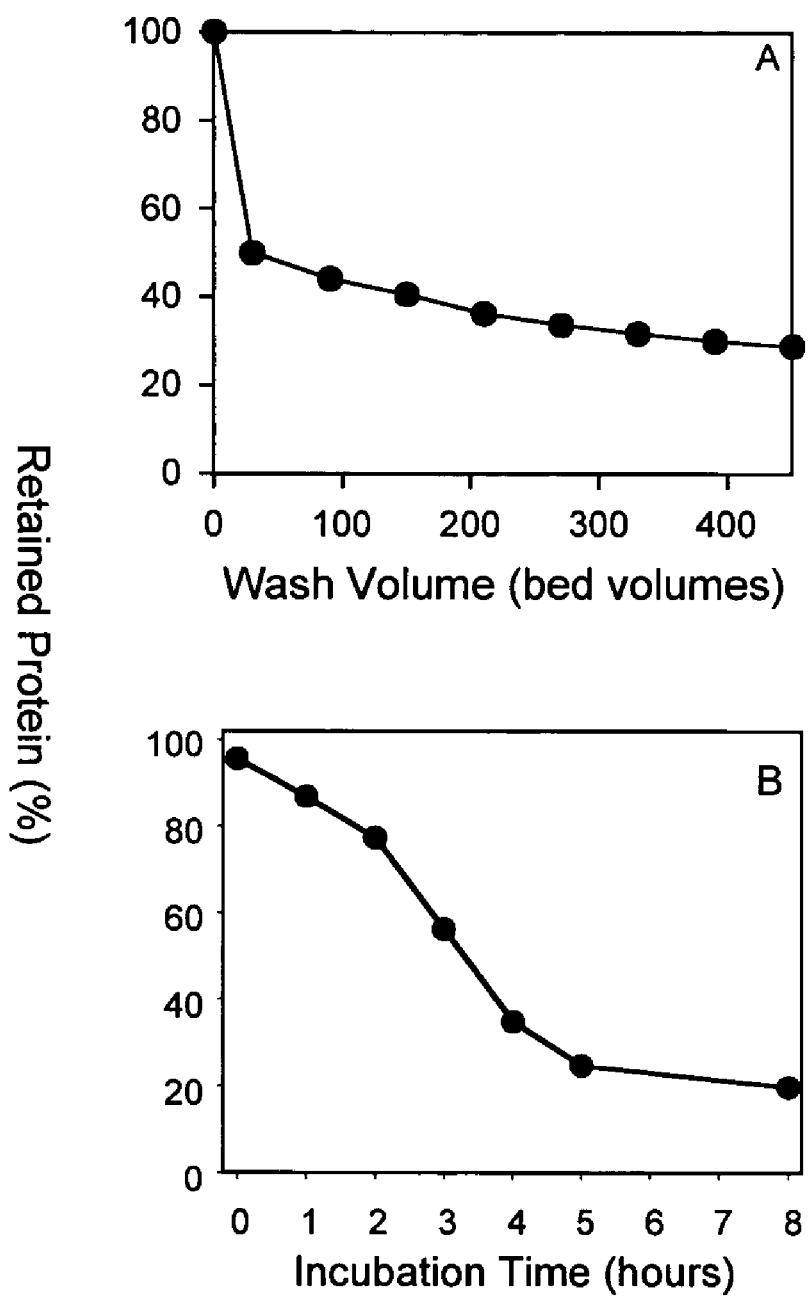
FIG. 21 shows the contributions to loss of column performance due to leaching and denaturation of DHFR. Panel A: Amount of fluorescein-labeled DHFR remaining within macroporous monolithic columns after washing 450 bed volumes through the column over 8 hours. Panel B: Effect of incubation in 2 mM ammonium acetate (used as FAC/MS running buffer) on DHFR activity.

To further explore the properties of the DHFR-doped columns, the effect of ligand concentration on elution time was examined for both pyrimethamine and trimethoprim. As the concentration of ligand increases, one expects the column to saturate more rapidly for a given flow rate, and thus the compound is expected to breakthrough earlier. By plotting elution volume against analyte concentration one can determine the amount of protein immobilized ($B_t$) and the dissociation constant of the protein directly on the column. FIG. 20 shows breakthrough curves for pyrimethamine at various concentrations, and the resulting plot of V vs. [A]. From this data one extracts a total protein concentration of 12 pmol on the column, and a $K_d$ of 47 nM. The $K_d$ value is essentially identical to that in solution (37 nM) and is in excellent agreement with the value obtained for DHFR entrapped in DGS derived materials (46 nM).[43] The data obtained from trimethoprim provided a $K_d$ value of 21 nM and a $B_t$ value of 7 pmol (data not shown). The $K_d$ value for trimethoprim in DGS is 3 nM, thus, the affinity of the inhibitor is somewhat lower than previously reported, but is still in the nM range and therefore would be considered a hit in a high-throughput screen. The higher $K_d$ value for trimethoprim obtained by FAC/MS may be the result of the low ionic strength buffer used in these experiments. The $B_t$ values indicate that only 15-25% of the initially loaded protein remained active and accessible. The remainder (75-85%) of the initial protein present was therefore either denatured, inaccessible or removed from the column during column conditioning. To distinguish between these possibilities, two experiments were performed. To test protein leaching, DHFR was fluorescently labeled and entrapped in the column. The column was then washed with 2 mM ammonium acetate buffer for 8 hours, and the amount of protein remaining in the column each hour and at the end of the 8 hour wash was determined. As shown in FIG. 21a, a large fraction of protein leached in the first hour (corresponding to the time used to condition the column), after which leaching of protein occurred slowly. After 8 hours there was still ~30% of the initial protein entrapped in the column and leaching was minimal. Thus, leaching of protein is not the main reason for the lack of reusability. In a second experiment, the column was flushed for 8 hours with 2 mM ammonium acetate (the running buffer) before the binding assay. In this case there was a dramatic decrease in binding performance (>80%), which was attributed to denaturation of the protein in the presence of the low ionic strength buffer. This was confirmed by incubating the protein in 2 mM ammonium acetate buffer and assaying enzyme activity every hour. As shown in FIG. 21b, the protein retained only 20% of its initial activity after this treatment. Taken together, these experiments demonstrate that the use of low ionic strength buffers, which are optimal for ESI-MS, result in denaturation of DHFR, causing the loss of column performance.

Figure 22:
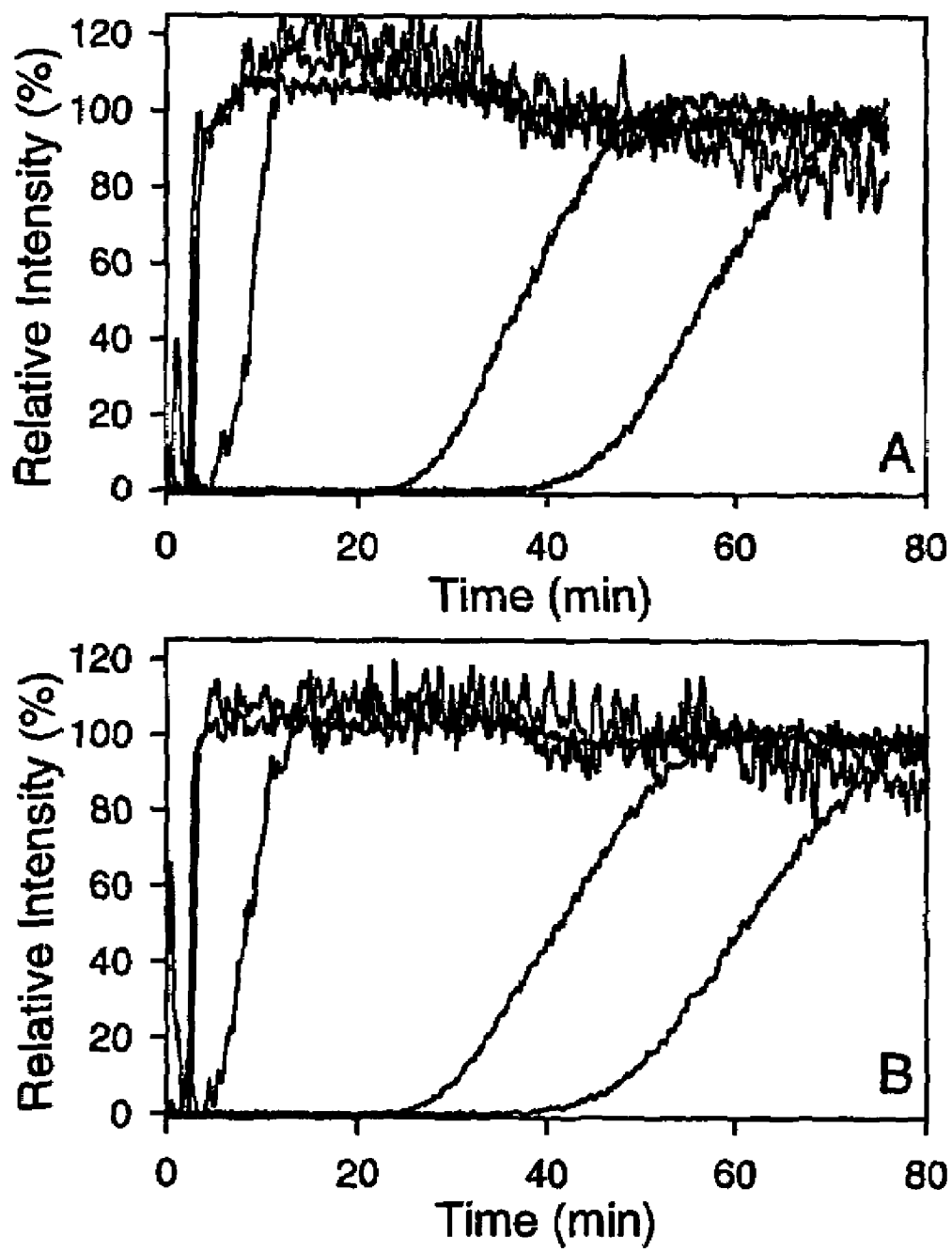
FIG. 22 shows the column to column reproducibility for elution of 5 compounds. Panels A and B show FAC/MS data obtained for two different columns cut from one continuously filled capillary. Columns were infused with a solution containing 20 nM of coumarin, folate, trimethoprim and pyrimethamine and 100 nM Fluorescein in 2 mM ammonium acetate. The order of elution was coumarin (2.7 and 2.6 min), fluorescein (3.1 and 2.9 min), folate (8.9 and 8.4 min), trimethoprim (37.2 and 41.4 min) and pyrimethamine (56.7 and 61.4 min).

FIG. 22 shows the reproducibility between columns within the same batch (i.e., cut from the same capillary). In this case, three different 10 cm columns were cut from the midsection of a 1 m long capillary and were examined after washing 30 bed volumes of buffer through the column over a period of 1 hr to remove glycerol and any loosely adsorbed protein. The data were all obtained for the first run of compounds through the columns. It is clear that the columns showed acceptable reproducibility, with the relative standard deviation between columns being in the range of 5% or less. Reproducibility between columns obtained from different batches was slightly poorer, showing RSD values on the order of 8% (data not shown). These data suggest that the sol-gel composition and processing methods used to form the column lead to reproducible column performance, and make it possible to directly compare data obtained from different columns. This is further supported by the data shown in FIG. 20, where data obtained from four different columns was combined to generate reliable $K_d$ and $B_t$ values with $r^2$>0.998.

Figure 23:
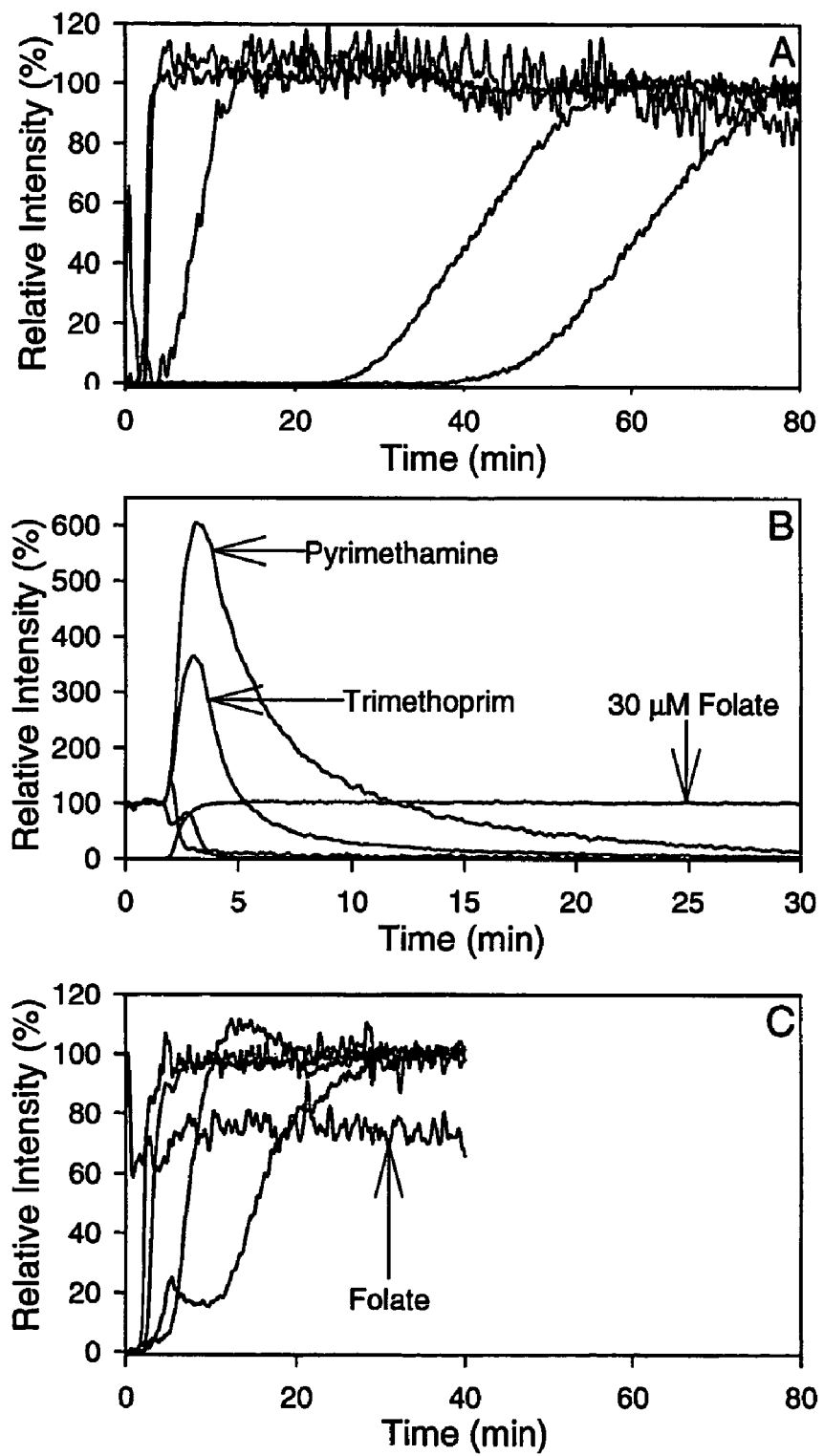
FIG. 23 shows the run-to-run reproducibility and column regeneration for a 5 day old DGS/PEO/APTES column containing an initial loading of 50 pmol of DHFR. The order of elution for panel A (initial run) was coumarin, fluorescein, folate, trimethoprim and pyrimethamine. After re-equilibrating the column with 2 mM ammonium acetate, 30 mM folate was flowed through the column for 40 min to displace tightly-bound affinity analytes in panel B. The column was then re-equilibrated with 2 mM ammonium acetate before FAC was repeated in panel C.

FIG. 23 shows the reproducibility between runs (Panels A and C) and the regeneration of the columns (Panel B) using a weak affinity ligand (folic acid) to displace stronger binding ligands (pyrimethamine and trimethoprim). The displacement of tight binding ligands (panel A) by a known weak binder (Panel B) can be used to confirm their specificity for the catalytically relevant site on the surface of the target protein. The retention time for pyrimethamine dropped from 60 min to 15 min while those for trimethoprim dropped from 40 min to 7 min after column regeneration (panels A and C). Thus even after washing the column with an excess of a weak ligand to aid in displacement of stronger ligands, the original column activity was not recovered. This is consistent with the data presented above (FIG. 21), which show that prolonged exposure of the entrapped protein to the low ionic strength running buffer leads to irreversible denaturation of the entrapped protein. It is also possible that binding of the strong ligand led to partial irreversible inhibition of the protein.

Discussion for Examples 18-20

Meso/macroporous sol-gel based monolithic bioaffinity columns are ideally suited for the screening of compound mixtures using frontal affinity chromatography with mass spectrometric detection for identification of specific compounds in the mixture. The ability to interface the capillary columns directly to an electrospray (ESI) mass spectrometer is a key advantage of the new columns, and can make them suitable for HTS of compound mixtures using FAC/MS. While direct comparison to bead-based columns was not done in the present study, the monolithic columns clearly provide advantages in terms of ease of column loading and control over protein loading. Columns were formed simply by mixing the hydrolyzed silane with the polymer and protein-doped buffer and pumping the mixture into the capillary prior to spinodal decomposition and gelation. This one-step column fabrication method leads to good column-to-column reproducibility. The monolithic columns retained up to 25% of the loaded protein in an active form based on the $B_t$ values reported above. The monolithic columns also had low backpressures (due to the macroporous nature of the material), which allows the use of a low-pressure syringe pump for pumping of eluents. The ability to operate at low pressures and low flowrates makes the monolithic columns amenable to direct interfacing with ESI/MS, with no need for flow splitting. This maximizes sensitivity and thus results in an ability to use low levels of compounds and hence small amounts of immobilized protein (ca. 10 pmol). This latter point is of significant importance when expensive and/or low abundance proteins are used as targets for FAC/MS based screening. Library compounds may be equally valuable and available in small quantities, making this technique more attractive.

One of the major advances in the development of the new columns was the use of the biocompatible sol-gel precursor DGS for column fabrication. Recent studies from the present inventors have conclusively demonstrated that DGS and related sugar-modified silanes are able to maintain the activity of a wide variety of proteins, and in particular are able to stabilize proteins that denature readily when entrapped in materials derived form alkoxysilanes such as tetraethylorthosilicate.[43] The evolution of glycerol as a byproduct of DGS hydrolysis maintains the entrapped proteins in an active state during column aging, yet is readily removed from the column during the initial column flushing step owing to its small size relative to the protein, avoiding elution of glycerol into the mass spectrometer. The ability to remove entrapped glycerol from DGS derived materials by washing has been previously confirmed by thermogravimetric analysis.[44]

A key issue that was examined as part of column optimization was minimization of non-selective retention mechanisms, which could result from interactions of compounds with the silica matrix. Since silica is polar and anionic, it is expected that interactions with polar and cationic compounds might occur, as was observed in the present work. Counterbalancing of the anionic charge using the cationic silane APTES resulted in a remarkable reduction in non-selective retention, while at the same time not producing significant changes in entrapped protein behaviour. APTES could be easily incorporated into the column by adding it to a buffered PEO/protein solution, and the level could be adjusted simply by altering the APTES concentration in the starting buffer mixture.

While the current work has focused on entrapment of a soluble enzyme, the sol-gel method employed herein is also amenable to the entrapment of a wide range of important drug targets, including membrane-bound enzymes and receptors,[58] and even whole cells.[55] Furthermore, entrapment into DGS derived materials allows immobilization of labile enzymes, such as Factor Xa and Cox-II, which are difficult to immobilize by other methods.[43] Thus, the monolithic columns may find use in screening of compound mixtures against a wide variety of useful targets.

Overall, monolithic silica columns containing entrapped proteins are shown to be amenable to bioaffinity based screening of small molecule-protein interactions using frontal chromatography in conjunction with mass spectrometric detection. The new columns are formed using a biocompatible one-pot processing method involving the addition of a buffered aqueous solution containing polyethylene oxide (PEO, MW 10 kDa) and the protein of interest to a hydrolyzed solution of DGS, followed by loading of the column. The resulting material retains protein activity, and at the same time provides the required pore distribution that is needed to obtain good flow of eluent with low backpressure. Inclusion of a small amount of APTES is shown to reduce non-selective adsorption, resulting in a column that retains compounds primarily as a result of bioaffinity interactions with entrapped proteins. Formation of columns within 150-250 µm i.d. fused silica capillaries provides a system that requires only very small amounts of protein (50 pmol loading, 12 pmol active protein) to produce a useful bioaffinity column. Such columns are suitable for pressure-driven liquid chromatography and can be operated at relatively high flow rates (up to 500 $\mu L.min^{-1}$) with low backpressures. More importantly, the operation of these columns with low ionic strength eluents allows direct interfacing to an electrospray mass spectrometer, allowing identification of small molecules using the multiple reaction monitoring mode, although such buffers do lead to relatively rapid denaturation of the entrapped protein. The ability to detect inhibitors present in compound mixtures via retention time combined with MS detection can be very powerful for high-throughput screening of compound mixtures.

Example 21

Activity and Inhibition of Src Protein Tyrosine Kinase Entrapped Within Sugar-Modified Sol Gel Derived Silica Gel Materials: Diglycerylsilane (DGS) was prepared as previously reported[6,44] and N-(3-triethoxysilylpropyl)gluconamide (GLTES) was prepared as described above (see Example 1). Src kinase, human recombinant, expressed in insect cells (product number S5439), adenosine triphosphate, trisodium salt (ATP), bovine serum albumin (BSA) and dithiothreitol (DTT) were purchased from Sigma-Aldrich (Oakville, ON). Biotin(EEEEY)$_n$ (denoted in this study as P44000), anti-phosphotyrosine(PY20)-cryptate and XL665-conjugated streptavidin were purchased from CIS Bio International (Bedford, Mass.). 384-well transparent bottom black microplates with a well volume of 120 L were acquired from BD Biosciences (Franklin Lake, N.J.). The biotinylated peptides $bE_4Y$ (denoted here P1037), $b(E_4Y)_2$ (P1716) and $b(E_4Y)_3$ (P2396) were synthesized by Biosource International. YIYGSFK, YIYGSFKb (P1104) and bENDpYINASL were obtained from AnA Spect (La Jolla, Calif.). Staurosporin and Src Kinase inhibitor I (4-(4-phenoxyanilino)-6,7-dimethoxyquinazoline) were obtained from EMD Biosciences (Darmstad, Germany). All reagents were used as received without further purification. All solutions were made with water that was distilled and deionized through a Milli-Q Synthesis A10 4-stage water purification system.

Methods:

(a) Encapsulation of Src: The sol was prepared by sonicating DGS (400 mg) and water (1000 L) ($H_2O$:Si molar ratio (R-value) of 13) at 0 ,C for 45 min to hydrolyze the monomer. Equal portions of the resulting sol and 0.2 M GLTES in 50 mM MOPS pH 7.8 containing 10 mM $MgCl_2$, 0.4 mg.mL$^{-1}$ BSA and 1 mM DTT were mixed so as to obtain a molar GLTES:DGS:water ratio of 0.2:2:100 (R=45). For studies involving P44000 the buffer used was 50 mM HEPES containing 10 mM $MgCl_2$, 0.4 mg.mL$^{-1}$ BSA and 1 mM DTT, since this buffer was recommended by the supplier for use with the peptide. The buffer also contained 2 mM ATP, except for inhibition studies, where no ATP was added. Immediately after mixing the solutions of DGS and GLTES, a solution of Src (50 pM) in an identical buffer system was added to reach a concentration in the sol of 5 pM. The final molar ratio of water to silica was 63. The sol was briefly and carefully mixed to obtain rapid homogenization and loaded in portions of 20 L into a 384-well microplate. Gelation of the sol generally occurred in less than 1 min. Sols composed of DGS or DGS and PEO were prepared using a similar procedure, except that GLTES was substituted with a solution of 50 mM MOPS or 4 or 8 mM PEO (10 KDa) in 50 mM MOPS. TEOS and TMOS based gels were prepared as described elsewhere.[22,25] The concentration of the enzyme was identical in all sol-gel derived materials.

Once filled, the microwell plates were covered with Parafilm™ and over each well a small orifice was opened with a syringe in order to allow slow drying of the gel. The gel was aged at 4 ,C for 5 days before assays were performed, unless otherwise stated. For reusability studies the gels were stored at 4 EC in a minimal volume of buffer to maintain hydration.

Figure 29:
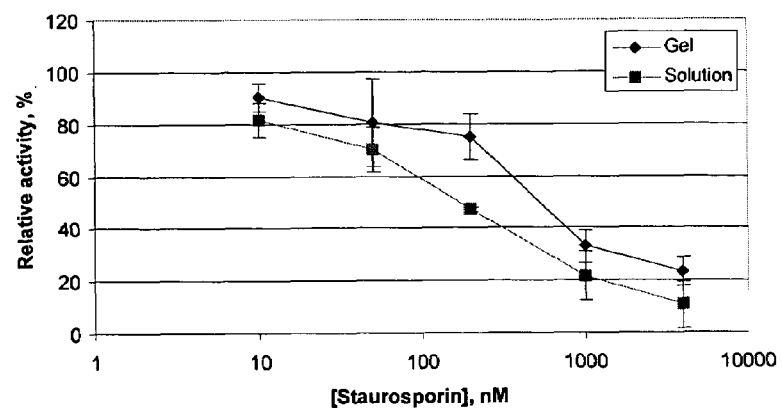
FIG. 29 shows the effect of increasing concentration of PTK inhibitors on free and entrapped Src activity. a) Staurosporin, [P1716]=8 M, [ATP]=40 M; b) Src Kinase Inhibitor I, [P1716]=4 M, [ATP]=20 M; c) YIYGSFK, [P1716]=8 M, [ATP]=40 M.
Figure 29:
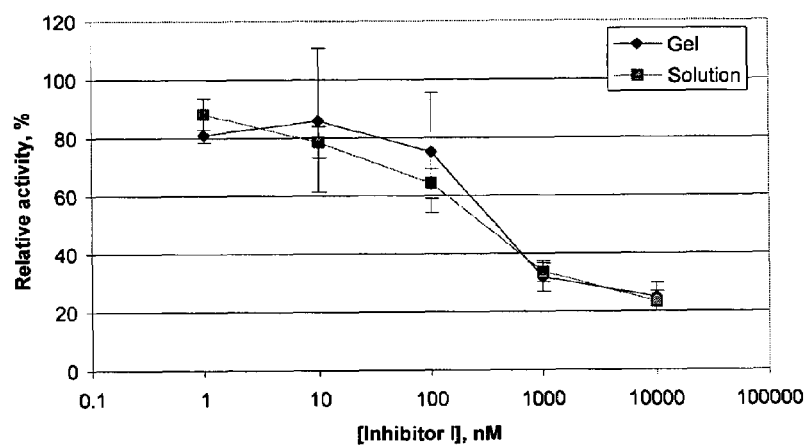
Figure 29:
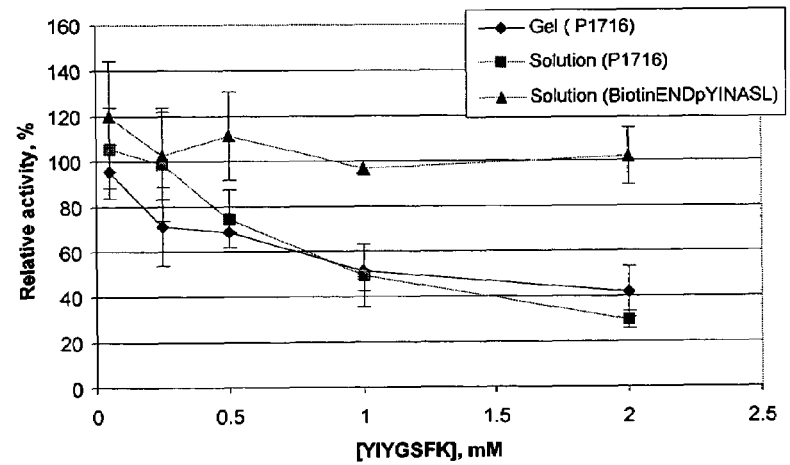

(b) Activity measurements: After aging, the gels were carefully washed 3 times for 20 min per wash with 50 mM MOPS, pH 7.8 to remove entrapped glycerol. Failure to wash the gels resulted in poor activity for the entrapped enzyme. After washing, 20 L of a solution containing 1 mM ATP and different concentrations of the biotinylated substrates in 50 mM MOPS, pH 7.8 was loaded on top of the gels and incubated for 16 h at 30 ,C (longer incubation times did not increase the S/B ratio for detection of phosphorylated peptides). For inhibition studies, 10 L solutions of inhibitors were loaded on top of the gels and preincubated for 2 h before the reaction mixture was added. The sample was then incubated for a further 16 h before activity measurements were performed. The concentration of ATP and P1716 used for these experiments is indicated in FIG. 29. The reusability of the entrapped Src was examined by washing the gel three times with MOPS buffer after measuring the activity (20 min per wash) to remove the components of the detection mixture and products of the reaction, and then assayed again with the reaction mixture containing ATP and biotinylated substrates. This operation was repeated once a day for eight consecutive days. For solution based assays the gel was replaced with 20 L of 5 pM Src in 50 mM MOPS and activity was measured as described for entrapped Src.

The phosphorylation of the biotinylated peptides was assessed by fluorescence resonance energy transfer coupled with time resolved detection (TR-FRET).[40b] Immediately after incubation with substrate was complete, 60 L of a mixture of anti-phosphotyrosine(PY20)-cryptate (Eu-labelled antibody) and XL665-conjugated streptavidin (Cy5-streptavidin) were added to achieve a final concentration of 4 nM and 200 nM, respectively (detection cocktail). The plates with the detection cocktail were incubated for one hour at room temperature and the fluorescence was measured from the bottom of the plates using an excitation wavelength of 304 nm after a 50 µs delay with a TECAN Safire microplate reader (TECAN, Austria GmbH). Longer incubation times did not lead to improvements in S/B ratios. The mean of three measurements was recorded from each well. The relative quantity of phosphorylated peptides was determined from the ratio of emission intensity values at 665 nm (Cy5) and 584 nm (Eu), in samples and negative controls lacking the substrate or the enzyme. The results are expressed as signal/background ratios (S/B), and are the mean the standard deviation of two independent experiments.

Results and Discussion (a) The Detection System

Figure 24:
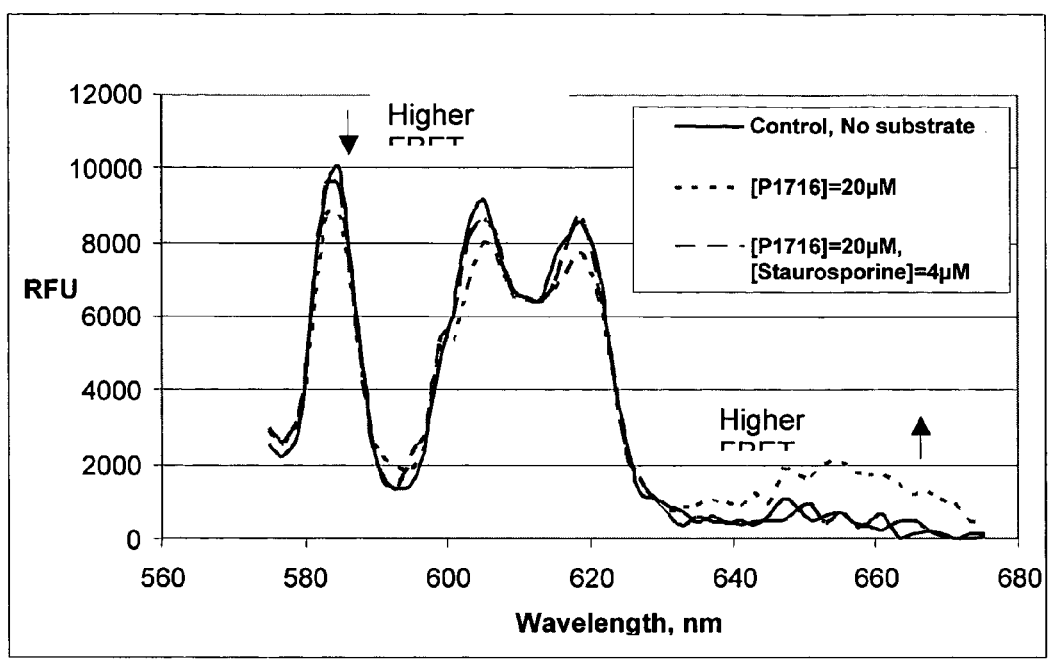
FIG. 24 shows TR-FRET spectra of Src PTK reaction products, with or without the substrate (P1716) and the inhibitor (Staurosporine).
Figure 25:
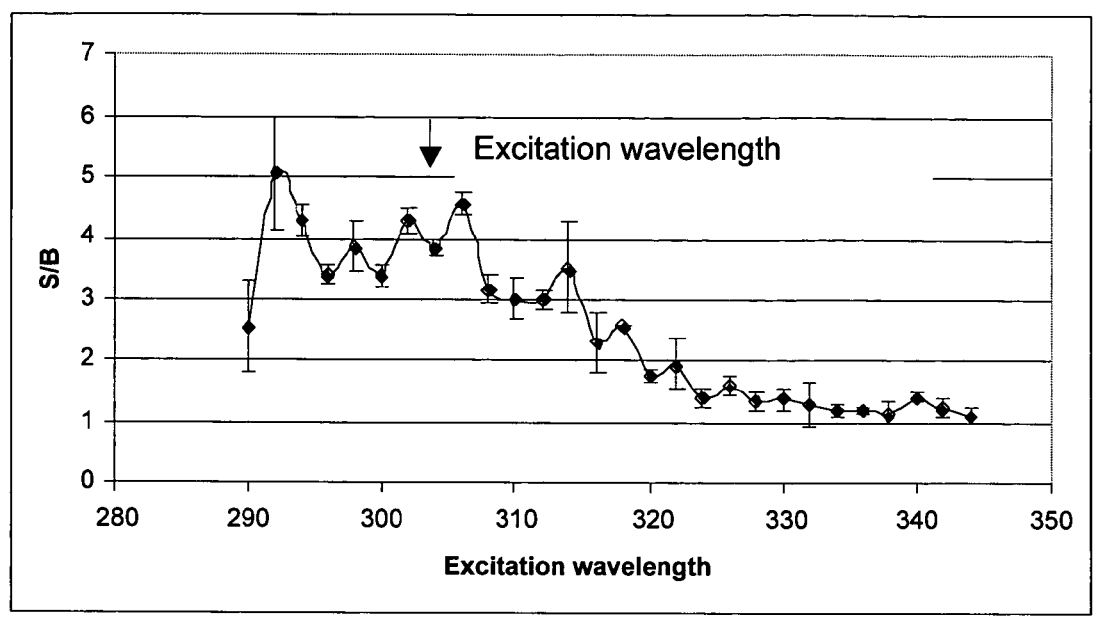
FIG. 25 shows the effect of excitation wavelength on S/B ratio in a solution containing bENDpYINASL and detection cocktail.

Of the numerous methods to assay PTK activity, homogeneous time resolved fluorometry linked with fluorescence resonance energy transfer (TR-FRET) is one of the most specific and simple. The assay doesn t require the use of radioactive isotopes and the whole procedure can be carried out in solution without the need for washing steps. The TR-FRET system used in this study to detect the formation of phosphorylated peptides utilizes the reaction of the biotinylated phosphopeptides with both a europium cryptate-labeled anti-phosphotyrosine antibody and Cy5 labeled streptavidin. When these two fluorophores come in close proximity upon binding to the phosphopeptide, resonance energy transfer between them can be detected after a lag time of 50 s, providing a specific signal related to the presence of a phosphorylated peptide. Use of delayed fluorescence eliminates scattering and short lived fluorescence signals, dramatically improving the S/B ratio. To avoid the effect of differences in probe concentration or quenching between samples it is common to measure the ratio between the emission intensity of Cy5 labeled streptavidin at 665 nm and europium cryptate at 620 nm.[40] It was found, however, that the ratio of emission intensities at 665 nm (Cy5) and 584 nm (Eu) provided a higher S/B, and thus used this ratio to measure TR-FRET (FIG. 24). Excitation wavelengths between 320 and 340 nm are commonly used for TR-FRET using Europium cryptates.[40] However, the measurement of S/B at different excitation wavelengths in the present system indicated that excitation at 304 nm provided the highest S/B (FIG. 25). To test the feasibility of using TR-FRET for heterogeneous systems containing both the gel and the detection cocktail in solution, the S/B ratio of a solution containing 20 L of 100 nM Biotin-ENDpYINASL and 60 L of the detection cocktail was measured and then the mixture was loaded on top of gels with different compositions (see FIG. 27 for a list of gel compositions). The S/B ratio of the solution of biotinylated phosphopeptide and detection cocktail loaded on top of the gels wasn t significantly different from that of the solution itself (i.e., in the absence of the gel), which indicates that the gels were transparent to the emission fluorescence and didn t affect the fluorimetric detection of biotinylated phosphopeptides.

(b) Performance of Entrapped Src Kinase

The most commonly used substrate for PTK studies is the synthetic polypeptide b(EEEEY)$_n$, which has a molecular weight of 44 KDa (denoted P44000 in this study). The multiple tyrosine residues in this peptide facilitate both the phosphorylation reaction and the binding of the anti-phosphotyrosine antibody. However, the large size of this substrate proved to be an obstacle for assaying the activity of Src Kinase entrapped in sol-gel derived materials, because the size of the pores (~10 nm diameter[21]) is too small to allow the diffusion of such a large substrate to the sites where the enzyme is encapsulated. To achieve better accessibility of the substrates to the enzyme, shorter peptides with a similar structure were designed (Table 13). Multiple anionic glutamic acid residues were included in the peptide to help minimize non-specific interactions of the peptide with the anionic silica surface. In addition to the synthetic substrates, the well known PTK substrate YIYGSFKb was also included in the study (denoted as P1104).[59]

Figure 26:
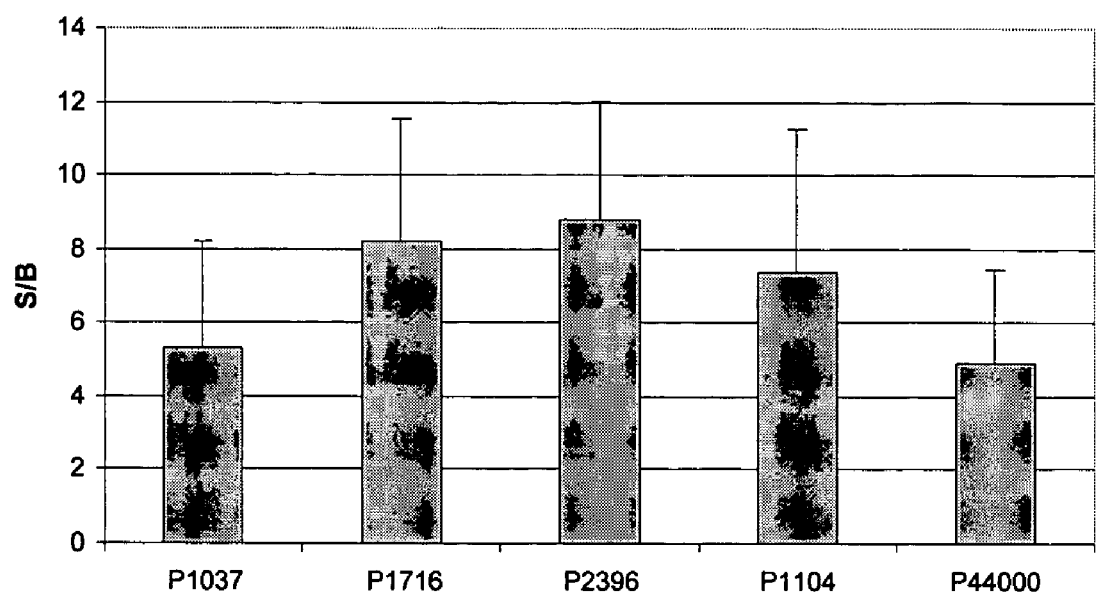
FIG. 26 shows the relative Src PTK phosphorylation activity of different substrates in solution.

The assay of these peptides in solution showed an slight increase in the S/B ratio as the number of tyrosine residues increased in the molecule from 1 to 3 (i.e., from P1037 to P1716 to P2396) (FIG. 26), although it should be noted that there are relatively large errors in the S/B values in all cases. For P44000 this ratio was somewhat lower, which could be due to a stoichiometrically insufficient quantity of antityrosine labeled antibody, considering the large number of tyrosine residues in this peptide.

Src was then entrapped in a series of different sol-gel derived materials, and signaling magnitude was optimized using the material that provided the best Src activity (see below). The signal magnitude over background for entrapped Src was optimized in terms of both the concentration of peptide and the amount of entrapped Src. Increasing the concentration of the peptide substrates increased the S/B ratio up to a saturation plateau of S/B=6. However, above a concentration of ca. 10 μM of peptide, the S/B ratio decreased due to an excessive quantity of phosphorylated peptide in relation to the components of the detection mixture. In such a situation there is a high probability that the peptide will not bind to both the antibody and the streptavidin, as these proteins are limiting reagents in the mixture. Hence, the extent of TR-FRET will decrease as peptide concentration increases beyond the stoichiometrically optimal value. Increasing the concentration of the enzyme in the gel also led to a higher S/B ratio, but again the S/B ratio reached a plateau at an enzyme level of 5 ng/well (5 pM in the gel), which is likely indicative of complete substrate phosphorylation at this enzyme level.

Figure 27:
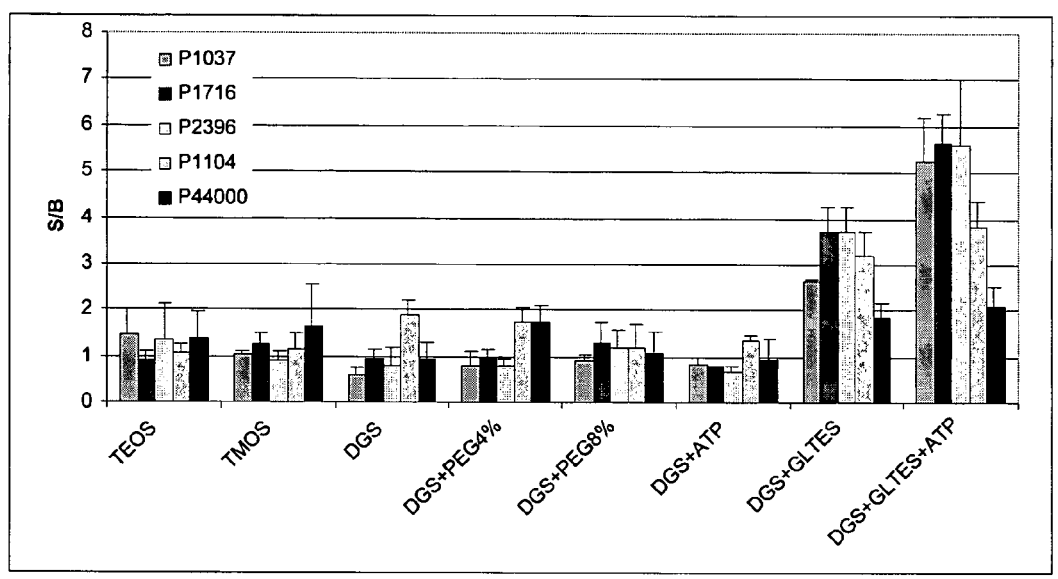
FIG. 27 shows the relative activity of Src PTK entrapped in different sol-gel systems.

The nature of the silica material also had a marked effect on the S/B ratio obtained from fluorimetric assays of entrapped Src, as shown in FIG. 27. Entrapment of Src in TMOS, TEOS or DGS-derived materials did not lead to significant signal above background. In the case of TMOS and TEOS, it is possible that the high acidity and high concentration of alcohol present in sols derived from these precursors led to the denaturation of encapsulated Src. However, the lack of substantial signal in DGS-derived materials, which are formed under neutral conditions and release the biocompatible molecule glycerol, suggests that the activity is not dependent solely on the biocompatibility of the starting material, but may also dependent on other factors, such as the pore size or polarity of the final material. DGS-derived materials have a pore diameter that is only slightly larger that is obtained for TEOS derived materials (3.1 nm for DGS vs. 2.6 nm for TEOS after drying).[6] Addition of 10 K PEO, which creates macropores in sol-gel derived materials, did not improve the S/B ratio, possibly owing to significant leaching of Src from the macropores during the initial washing steps. Addition of PEO does not have a major influence on the diameter of mesopores (pore diameter is 3.5 nm for dried samples),[44] and thus it is possible that Src entrapped in mesopores was not accessible to the polypeptide analytes.

The addition of GLTES, which contains a gluconamide moiety that is covalently attached to the silica surface through a triethoxysilane group, at levels of up to 10 mol % with respect to DGS, resulted in a significant improvement in the S/B ratio. Inclusion of 1 mM ATP, a substrate for Src Kinase, to GLTES doped glasses further improved the S/B ratio to the point where it was almost equivalent to that in solution. Further increases in the mole fraction of GLTES or the concentration of ATP did not lead to further improvements in the activity of entrapped Src. These results indicate that all of the short peptides (P1037, P1716, P2396 and P1104) were able to enter the glass and interact with entrapped Src, while the large peptide P44000 was not. Assays of the external solution after incubating a Src loaded gel in buffer for 16 h showed no appreciable signal above background, indicating that the fluorescence response was not due to Src that had leached from the gel.

While the role of GLTES in improving the activity of entrapped Src is not fully understood at this time, possible reasons for this effect (while not wishing to be limited by theory) include surface modification of the silica, resulting in fewer anionic silanolate sites that are available for interaction with ATP and the anionic peptide substrates (which could lead to analyte exclusion from the matrix)[29,60,61] alterations in protein hydration and/or excluded volume, which prevent protein denaturation,[62] or improved accessibility of the entrapped enzyme to analyte owing to larger mesopores (the pore diameter of 10% GLTES glasses was 7.3-0.3 nm after drying, while the pore diameter of DGS derived glasses was 4.6-0.1 nm after drying). Increases in pore sizes has previously been observed for sugar-doped silica materials,[63] providing support for the ability of sugars to alter pore morphology.

Again, while not wishing to be limited by theory, the improvement in Src activity upon addition of ATP to GLTES doped DGS glasses is likely based on the known ligand-stabilization effect that has been reported for several proteins, both in solution[64,65] and when entrapped in sol-gel derived materials.[66,67] It is known that the dynamics of protein are greatly restricted in sol-gel derived silica relative to solution.[68] However, for many enzymes the motion of a large part of the molecule is desirable for achieving an active conformation. For Src and other PTKs in particular, the N-terminal lobe is moved away from the C-terminal lobe by 141 in the open (inactive) conformation when compared with the lobes in the closed (active) conformation.[59] During the process of encapsulation, when the gel is being shaped, it is possible that some enzyme molecules can be trapped in an inactive conformation. Then, depending on the interactions between the silica and the protein these molecules may not be able to undergo the required conformational rearrangement that leads to an active conformation. If ATP is added after entrapment of Src, it must diffuse through the pores of the silica, reach the Src and phosphorylate it to generate the active conformation. However, the rearrangement of the enzyme into an active conformation is likely hindered by the surrounding silica matrix. By adding ATP prior to the formation of the gel, the enzyme is able to adopt an active conformation before entrapment, which likely increased the number of Src molecules encapsulated in an active conformation, producing a higher overall activity.

Figure 28:
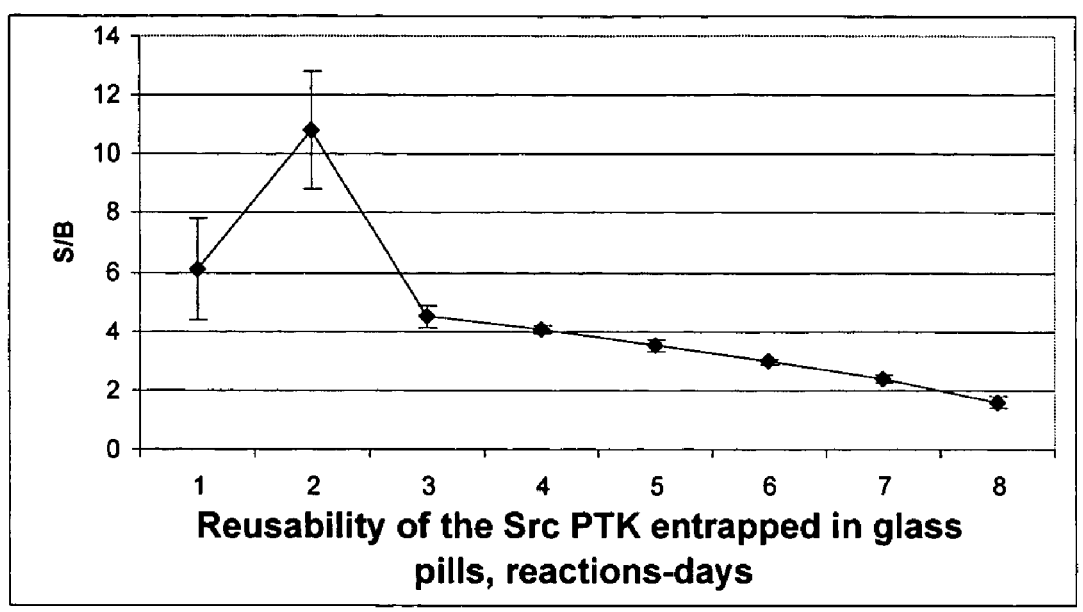
FIG. 28 shows the reusability of entrapped Src PTK. The enzyme activity was tested using P1716 as substrate.

FIG. 28 shows the S/B ratio of repeated assays of the entrapped Src, and shows that the enzyme retains approximately 30% of its initial activity after eight assay cycles. Analysis of the activity of the external solution indicated that the loss of activity with reuse was not due to protein leaching. Thus, the loss of activity is consistent with slow denaturation of the entrapped protein with repeated use. Assaying of entrapped Src that had been stored in ATP loaded silica for long periods at 4 EC indicated that the entrapped enzyme remained fully active for at least 90 days, thus the loss of activity upon reuse is not due to aging time, but rather is related to repeated assaying of the enzyme.

An unexpected finding was that the observed S/B ratio obtained upon assaying entrapped Src was reproducibly higher in the second assay cycle than in the initial cycle. Such behaviour has been observed previously for enzymes such as Factor Xa, dihydrofolate reductase and γ-glutamyl transpeptidase when entrapped in DGS derived materials.[43] While the origin of this effect is not fully understood and while not wishing to be limited by theory, it is possible that: 1) the long incubation used in the first cycle removed any residual glycerol, improving enzyme performance; 2) the introduction of the substrates in the initial assay cycle caused a higher fraction of the entrapped enzyme to adopt an active conformation; or, 3) the substrates remained in the gel after the first assay, leading to a higher amount of phosphorylated substrate for binding to the proteins in the detection cocktail.

(c) Inhibition of Entrapped Src Kinase

One of the most important applications of immobilized enzymes is their use as targets for the screening of potential inhibitors. In this study, three common inhibitors of PTK activity, staurosporin, an ATP competitive inhibitor, YIYGSFK, a peptide competitive inhibitor and Src Kinase inhibitor I,[69] which is both an ATP and peptide competitive inhibitor, were tested against Src both in solution and when the enzyme was entrapped in the GLTES/DGS derived silica matrix. As shown in FIG. 29, increasing concentrations of these inhibitors reduced the activity of entrapped Src in a manner that was essentially identical to that observed in solution. As shown in Table 14, the $IC_{50}$ values obtained in the silica matrix are close to the values obtained in solution, indicating that entrapped Src can be useful for inhibitor screening. These results are in agreement with recent results for other enzymes entrapped in DGS-derived materials, where it was observed that inhibition constants for binding of inhibitors to various entrapped enzymes were within error of the solution values.[43]

In the case of the peptide based inhibitor, it is possible that the observed decrease in S/B at higher inhibitor levels could simply be due to competition between phosphorylated YIYGSFK and biotinylated phosphopeptide for the anti-phosphotyrosine antibody in the detection cocktail. To prove that this was not the case, a reaction mixture containing only YIYGSFK with Src was prepared under identical conditions and after 16 h, a 200 nM solution of Biotin-ENDpYINASL was added to the reaction mixture. Increasing concentrations of YIYGSFK in the reaction did not affect the TR-FRET signal produced by Biotin-ENDpYINASL, indicating that YIYGSFK did not interfere with signal development. Hence, the observed decrease in the S/B ratio in the presence of this peptide shows that it effectively inhibits the phosphorylation reaction of entrapped Src when a biotinylated substrate (P1716) is present in the solution.

Overall, these results show that encapsulated PTKs can be used to study both phosphorylation reactions and inhibition of such reactions, and demonstrate that significant potential exists for the development of sol-gel based biosensors and HTS systems aimed at detection of PTK substrates and inhibitors Example 22

ATP Detection Using Firefly Luciferase Entrapped in Sol-Gel Derived Silica Containing Non-Hydrolyzable Sugar Moieties In this work, sol-gel precursors that are based on covalent linkage of D-gluconolactone or D-maltonolactone to aminopropyltriethoxysilane to form N-(3-triethoxysilylpropyl) gluconamide (GLTES-1) or N-(3-triethoxysilylpropyl)maltonamide. (MLTES-2) were prepared. Diglycerylsilane (DGS), GLTES, MLTES and allylgluconamide (allyGL) were prepared by methods described above. For DGS based sol-gel preparations, sols were prepared by sonicating DGS (400 mg, 1.34 mM) and water (1000 L) at $0,C$ for 45 min to hydrolyze the monomer. The resulting sol was mixed with equal portions of Tricine buffer (25 mM, pH 7.8) containing 5 mM $MgSO_4$, 0.1 $mg.mL^{-1}$ BSA, 0.5 mM DTT and 0.5 mM EDTA. The buffer also contained either 0.2 M allylGL or a range of concentrations of GLTES or MLTES, respectively, to obtain a sugar/DGS molar ratio of 0.05, 0.1, 0.15, 0.2 or 0.25. Immediately after vortexing the sol, a solution of Firefly luciferase from *Photinus pyralis* was added at a volume ratio of 30:1 sol:enzyme solution. The sol was very briefly and carefully mixed to obtain a homogeneous solution and was then loaded in portions of 62 L into a 96-well white microplate. The total quantity of protein per well was 200 ng (3 pM). TEOS-derived materials were prepared using a similar procedure, except that DGS was replaced by a TEOS-derived sol that was prepared by sonicating with a diluted hydrochloric acid, as described elsewhere.[22] The concentration of the enzyme in all gels was the same. TEOS was also prepared by a procedure in which the hydrolyzed sol containing TEOS was combined with an equal volume of deionized water and rotoevaporated until the volume was reduced to half,[70] with the aim of removing the ethanol liberated during the hydrolysis. The obtained sol was then mixed with the buffer solution and the enzyme as described above. Sodium silicate-based gels were prepared from 0.9 mL sodium silicate solution and 4 mL of water. This solution was agitated for 1 min with 2.0 g Dowex 50WX8-100 resin and vacuum filtered consecutively through a filter paper in a Buchner funnel and a 0.45 M membrane filter with the aid of a syringe.[71] The resulting sol was then combined with the buffer and the enzymes in the same proportions as for previous sols. In all cases, the plates were covered with Parafilm™ and over each well a small orifice was opened with a syringe in order to allow slow drying of the gel. The gel was aged at $4,C$ for 5 days forming a glass disk that adhered to the bottom of the wells.

To compare the activity of the enzyme in different sol-gel preparations, 50 L of 0.6 mM ATP in Tricine buffer of the same composition as used for gel preparation was added to each well and the reactions were started by adding 50 L of 100 M luciferin in Tricine buffer. The supernatants after the first washing were loaded in separated wells in order to measure the activity of leached enzyme. Kinetic constants were determined in relation to Luciferin and ATP, fixing the concentration of ATP at 0.3 mM (for determination of luciferin $K_M$ and $k_{cat}$ values) and fixing the concentration of Luciferin at 50 M (for determination of ATP $K_M$ and $k_{cat}$ values). The reusability of the enzyme was tested as above for several consecutive cycles: the silica disks were washed once and stored at 4 ,C for 1 week between cycles. Determination of ATP was done using 80 L of 200 M luciferin and 20 L of aqueous ATP solutions in the range between 1 and 100 pM.

The activity of the enzyme was determined by measuring integrated light emission over a 100 ms span, 5 min after the reaction started, using an ANALYST HT platereader (Molecular Devices Co., California). ATP detection assays were performed in a TR717 Microplate Reader (PE Applied Biosystems, CA) with an integration time of 30 s. All the results are reported as the mean ±SD of three independent samples.

Figure 30:
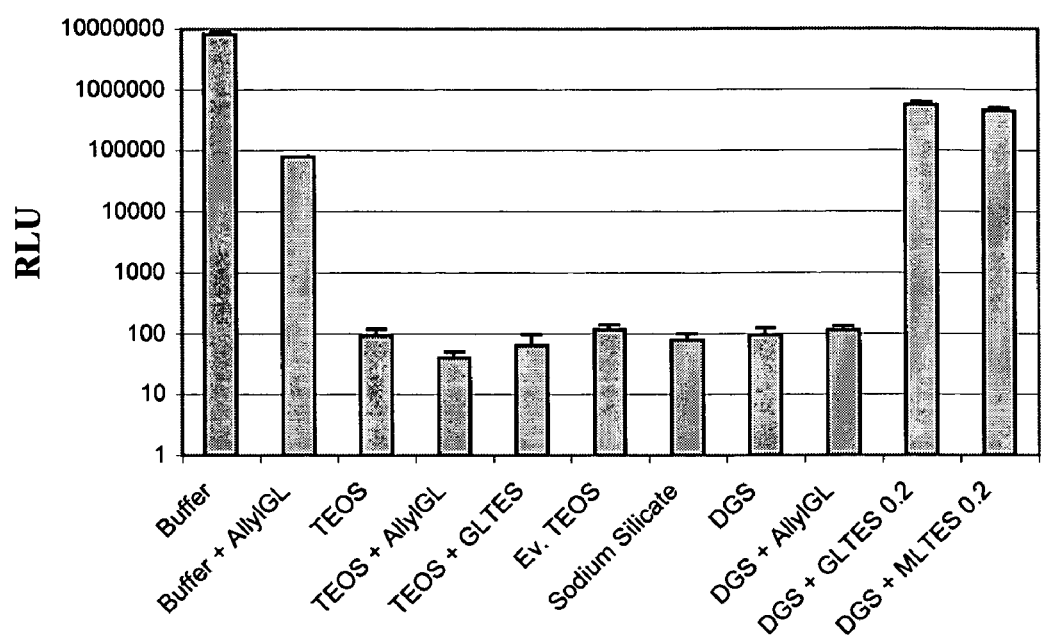
FIG. 30 shows the relative activity of luciferase entrapped in a variety of different sol-gel derived materials.

FIG. 30 shows the relative activity of FL in materials derived from TEOS, evaporated TEOS, sodium silicate, DGS, DGS:GLTES and DGS:MLTES, respectively. No activity was detected in any of the commonly used, unmodified silica-derived materials, including DGS derived glasses. However, there was substantial enzymatic activity observed for sugar-modified sol-gel derived silica containing a 0.1-0.25 mole ratio GLTES or MLTES. It must be noted that such materials are the first sol-gel based bioencapsulates to show any appreciable FL activity. The covalent incorporation of gluconamide or maltonamide into the silica matrix results in a material that shows less shrinkage, higher retention of water, larger pores and higher enzyme activity than alkoxysilane or DGS-derived materials, as described above (see FIG. 5).

To demonstrate the desirability of covalently tethering the sugar to the silica, assays were performed in TEOS and DGS derived materials that had free allylGL (0.1 mole ratio); such materials did not show any enzymatic activity. The results suggest that the ability of the matrix to retain water coupled with the lower degree of crosslinking leads to less pore collapse and thus maintains the entrapped protein in a more hydrated and hence solution-like environment. It is also likely that the coverage of the silica pore surface with non-hydrolyzable sugars may reduce adsorption of protein onto the silica surface, thus reducing the tendency for protein denaturation. Importantly, the use of a biocompatible precursor, such as DGS, without the non-hydrolyzable sugar, did not provide improved stability for entrapped FL. This indicates that the enzyme activity is as much dependent on the nature of the final material as it is on the processing method used to form the silica.

The $K_M$ values of the enzyme entrapped in 0.2 mol:mol GLTES:DGS materials in relation to luciferin and ATP were 4.9'1.3 and 5.2±0.4 M respectively, just slightly higher than the corresponding values in solution, 2.4±0.2 and 3.4±0.1M. This result shows that the accessibility of substrates to the enzyme in the sugar-modified sol-gel derived silica was relatively high. The present results also demonstrate higher accessibility of the substrates to the enzyme in relation to the data reported for other immobilization methods. For example, the $K_M$ values for luciferin and ATP in a system where the FL was covalently immobilized in agarose beads were 12.5 and 177.3 M, respectively;[72] in epoxy metacrylate the values were 89 and 6.6 M;[73] and in sepharose 5.5 and 300 M respectively.[74]

Figure 31:
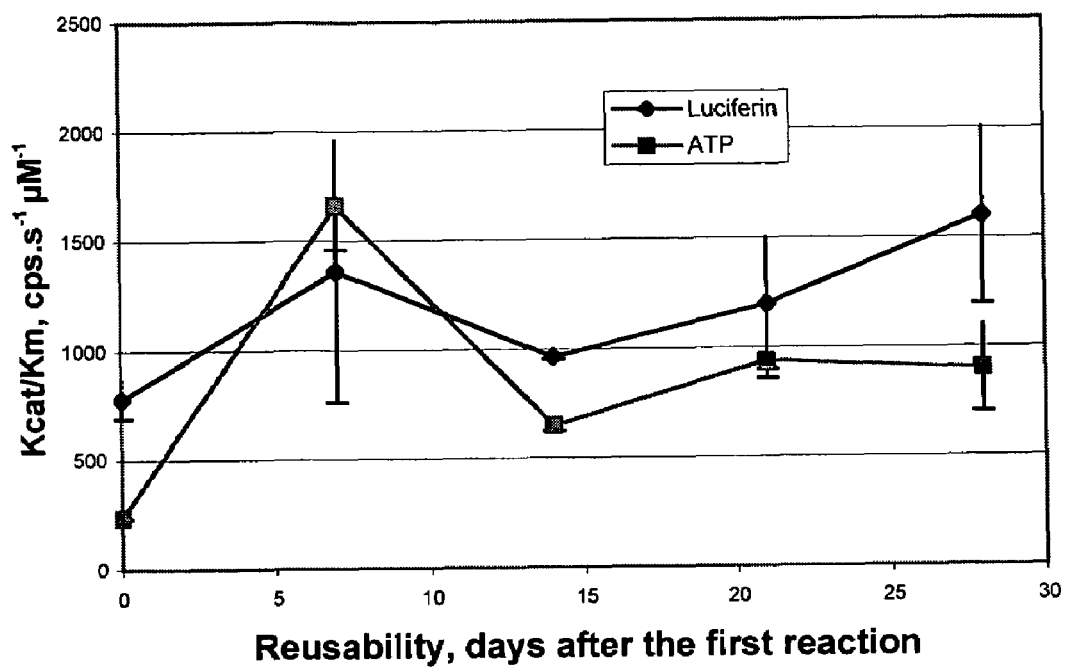
FIG. 31 shows the variation of catalytic efficiency with the reuse of firefly luciferase entrapped in 0.2 M/M GLTES/DGS gel.

The kinetic parameters of the entrapped enzyme were highly stable after reusing the gel in catalytic reactions over 5 cycles (FIG. 31). Measuring the enzymatic activity in the washing solution prior the assay of the activity in the gel produced <1% of the activity in the gel, which rules out leaching of the enzyme from the gel as the source of the activity. It is significant that the catalytic efficiency of the encapsulated enzyme dramatically increased after the first use. This phenomenon is a unique finding related to activity measurements in sol-gel derived glasses.[43] While this phenomenon is not completely understood and while not wishing to be limited by theory, it is possible that during the drying of the gel, part of the enzyme became highly adsorbed to the silica surface. The interaction with at least one of the substrates during the first catalytic cycle may change the conformation of the enzyme releasing it to the void volume of the pores and making the protein available for both substrates in the second catalytic cycle.

Figure 32:
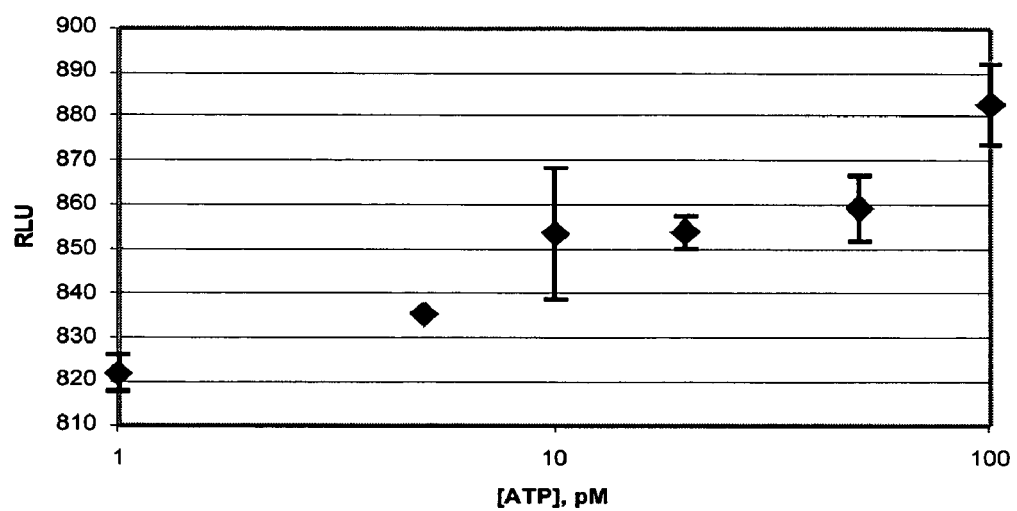
FIG. 32 shows the sensitivity towards ATP of FL entrapped in 0.2 mol:mol GLTES/DGS.

The FL-DGS-GLTES system was used as a sensor with high sensitivity towards ATP detection. We were able to measure a concentration as little as 1 pM ATP (FIG. 32), which means a quantity of 20 amol ATP in our initial volume of 20 L (note: the value of the blank was 760-5 RLU). This level of ATP corresponds to the total quantity found in about 20 cells. This is significantly lower than the values of ATP detection reported elsewhere using immobilized FL (ca. 1 fmol).[73,75] Furthermore, this is the first time FL has been encapsulated in a sol-gel system in a reusable format, highlighting the advantages of silica materials with covalently bound sugars for entrapment of proteins. This work paves the way for further development of devices based on FL doped silica that can allow for continuous detection of biowarfare agents or determination of contaminants in food or pharmaceutical products with high sensitivity.

Example 23

Factor Xa Entrapped in Sol-Gel Derived Silica Containing Non-Hydrolyzable Sugar Moieties Diglycerylsilane (DGS), and N-(3-triethoxysilylpropyl) gluconamide (GLTES), N-(3-triethoxysilylpropyl)maltonamide (MLTES) and allylgluconamide were prepared by methods described in the above experiments. S2222 was acquired from Chromogenix (Italy). Tris-HCl 50 mM pH 8.3, containing also 0.5 M NaCl and 5 mM $CaCl_2$ was used to prepare the gels and to carry out the reactions. A solution of Factor Xa was added to reach a concentration in the sol of 0.56 g/mL (13 nM). 96-well transparent microplates were used. To test the relative activity in different sol-gel preparations a solution of S2222, 400 M in buffer was added on top of the gel and absorbance at 405 nm was measured in a microplate reader (TECAN Safire). A total of 45 readings were taken from each well over a total time of 8 min.

After aging for 5 days, the gels were carefully washed 3 times for 20 min per wash with 50 mM Tris-HCl buffer pH 8.3. Then 200 L of S2222 (0, 100, 133, 200, 250, 400, 600, 800 M) were loaded on top of the gels and absorbance at 405 nm was measured in the microplate reader. A total of 45 readings were taking from each well during a total time of 8 min.

The values of absorbance were transformed to moles with the aid of a calibration curve previously determined for p-nitroaniline. For all assays the rate of product formation was evaluated from at least 20 data points after the first three minutes of reaction where the slope of the curve was still linear. The $K_m$ and $k_{cat}$ values were calculated by generating double reciprocal (Lineweaver-Burke) plots.

After the measurements, the silica monoliths were washed once with 150 L of 50 mM Tris-HCl for 20 min and the plates were covered with parafilm and stored at 4,C for further use. The measurements were repeated every 7 days.

To determine the kinetic constants in solution S2222 solutions in the same range of concentrations used in the gels were loaded on top of 60 L 0.56 g/mL solution of the enzyme.

Figure 33:
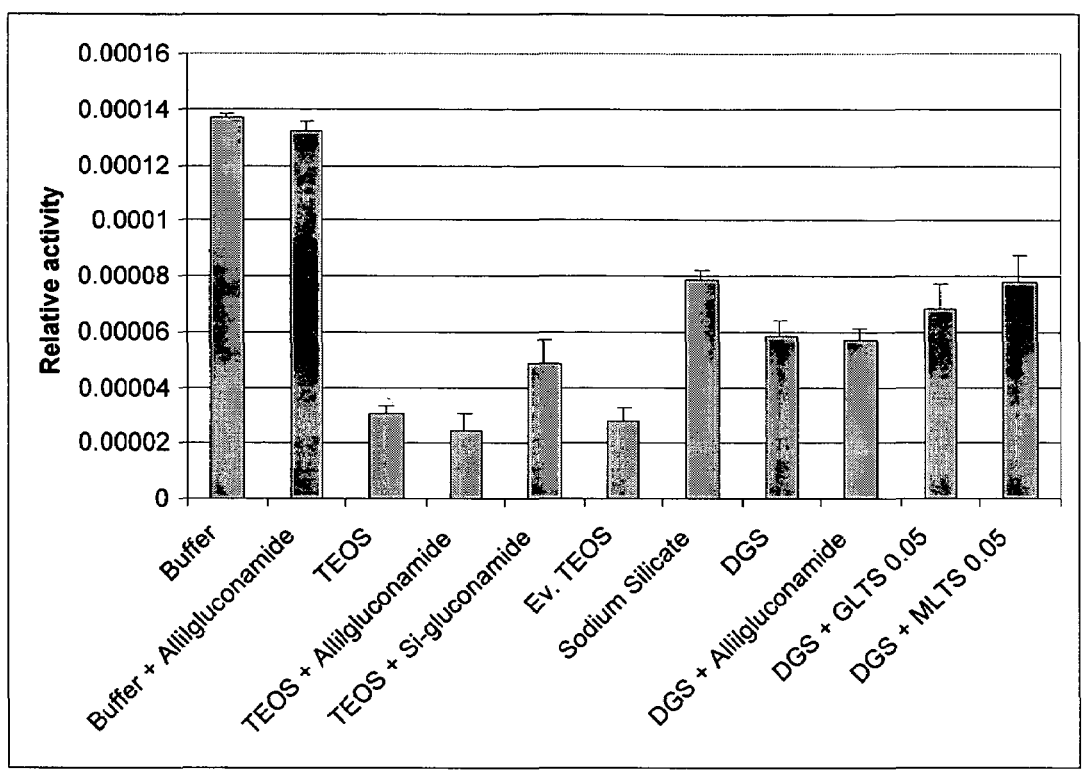
FIG. 33 shows the relative activity of Factor Xa entrapped in a range of preparations.

Factor Xa was tested in a range of preparations (see FIG. 33). While none of the immobilized Factor Xa samples showed activity that was equivalent to solution, it was observed that of all the immobilized enzyme samples, the highest activity was obtained from DGS derived samples that contained either GLTES or MLTES. Interestingly, addition of GLTES to TEOS derived materials also provided some improvement in activity relative to undoped TEOS materials. However, the activity was still lower than that obtained from DGS/GLTES samples. To ensure that the increased activity in such samples was due solely to entrapped enzyme, the leaching of enzyme from the materials was examined. In all cases, the leaching of the enzyme from gels, measured in the supernatant after the first washing of the gel, was always less than 1% of the activity of the enzyme in the gel.

Figure 34:
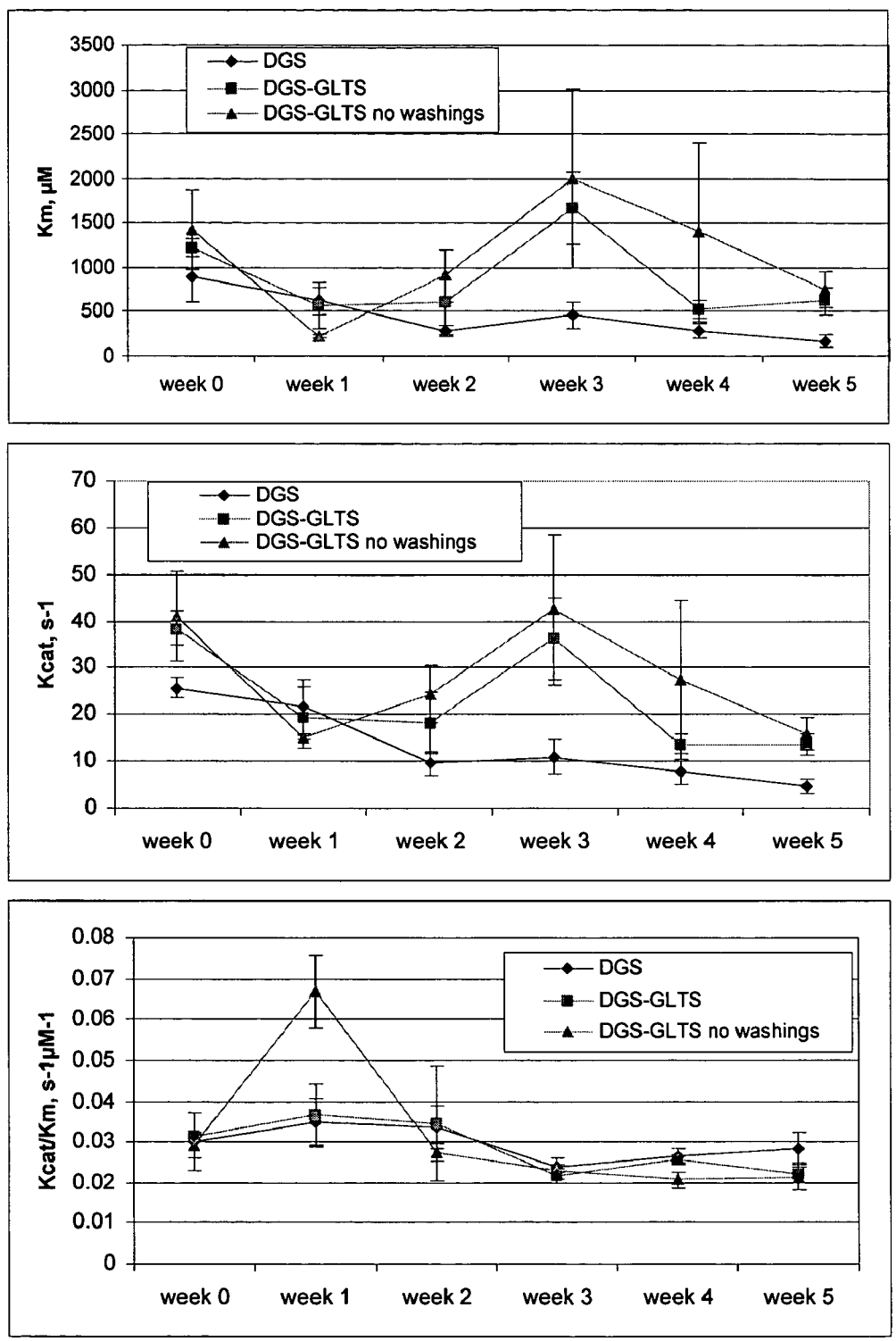
FIG. 34 shows the variation of catalytic efficiency with the reuse of Factor Xa entrapped in a 0.2 M/M GLTES/DGS gel.

The reusability of Factor Xa is shown in FIG. 34. In general, the $K_m$ value of the enzyme remained constant over at least 6 assay cycles, carried out over 5 weeks, when entrapped into GLTES doped DGS samples. The $k_{cat}$ value decreased by slightly more than a factor of two over 6 assay cycles, resulting in an overall decrease in catalytic efficiency of ca. 60%. DGS samples that did not contain GLTES showed lower initial activity, but also showed a decrease in catalytic efficiency on the order of 80%. Hence, addition of GLTES resulted both in higher initial activity and better long-term stability for entrapped Factor Xa.

Example 23

Figure 35:
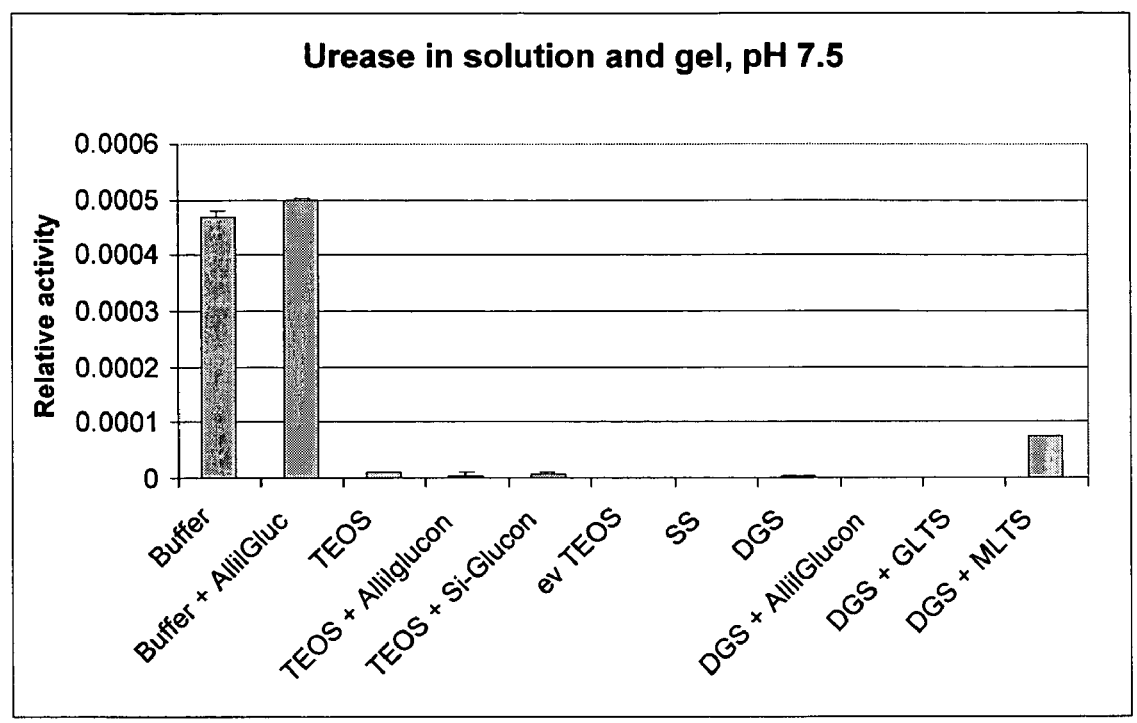
FIG. 35 shows the relative activity of urease entrapped in a range of preparations.

Urease Entrapped in Sol-Gel Derived Silica Containing Non-Hydrolyzable Sugar Moieties To further assess the ability of GLTES and MLTES to stabilize entrapped proteins, the activity of urease was examined within a variety of sol-gel derived materials. Urease was chosen for these studies as it has proven to be a particularly difficult enzyme to entrap in an active form in sol-gel derived materials. Urease (from Jack Beans) was tested in a range of preparations (see FIG. 35). Leaching of the enzyme from gels, measured in the supernatant after the first washing of the gel was always less than 1% of the activity of the enzyme in the gel. As expected, the entrapment of urease into TEOS, sodium silicate and DGS derived materials resulted in essentially not activity. Incorporation of GLTES into either TEOS or DGS also produced no appreciable activity. However, addition of MLTES resulted in approximately 20% of the activity observed in solution. These results are interesting as they suggest that specific sugar-modified silanes provide better stabilization of enzymes than others, depending on the enzyme under study. In the present case, the disaccharide maltonamidyl triethoxysilane provides better stabilization of urease than does the monosaccharide gluconamidylsilane. Thus, it is likely that assessment of a range of sugar-modified silanes will optimize the activity of specific enzymes.

Figure 36:
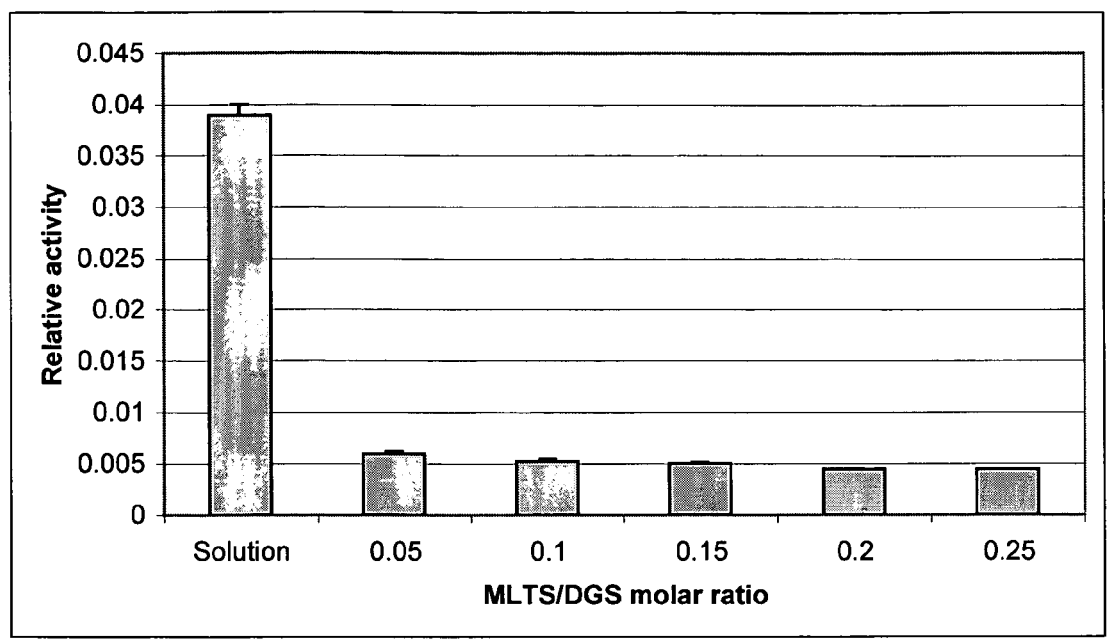
FIG. 36 shows the effect of mol/mol ratio of MLTES/DGS on urease activity.
Figure 37:
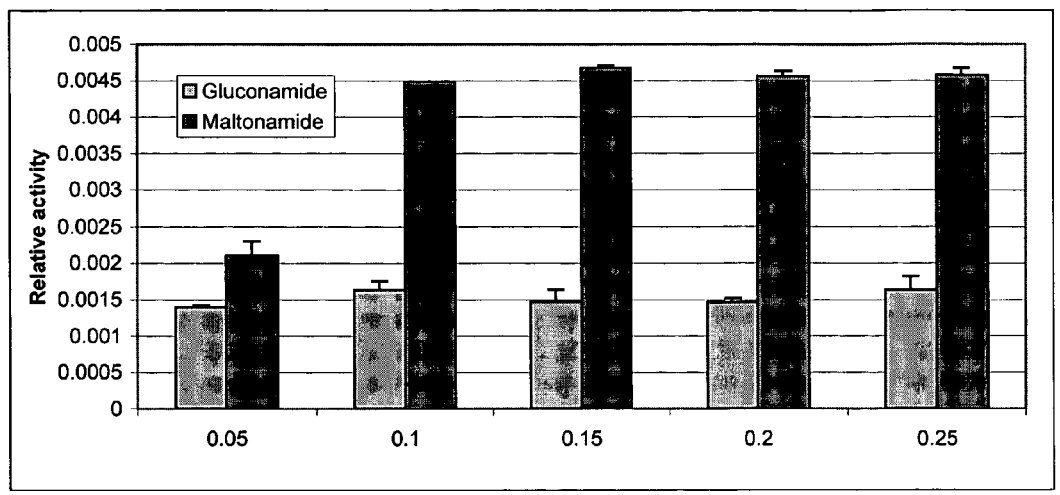
FIG. 37 shows urease activity in a range of gels with different mol/mol ratios of silinated sugars/DGS 7 days after the first measurement.

The effect of M/M ratio of MLTS/DGS on initial urease activity is shown in FIG. 36. In this case there does not appear to be a strong dependence on the concentration of MLTES. Interestingly, no activity was detected for urease entrapped in similar GLTS/DGS preparations. On the other hand, the activity of urease after 7 days of storage (following the initial activity assay) showed a concentration dependence for MLTES, with activity increasing and then plateauing as the concentration of MLTES increased (FIG. 37). The MLTES samples also showed higher overall activity after 7 days than was observed on day 1. In addition, after 7 days the activity of GLTES doped DGS materials increased significantly. These results, while not fully understood, may suggest that the initial assay cycle conditions the glass for further assays. In any event, the data show that activity does not decrease over a span of a week, even with reuse of the sample.

While the present invention has been described with reference to the above examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1]. A very clear discussion of the differences in flow characteristics between different types of silica may be found in Leinweber, F. C.; Lubda, D.; Cabrera, K.; Tallarek, U. Characterization of Silica-Based Monoliths with Bimodal Pore Size Distribution. *Anal. Chem.* 2002, 74, 2470-2477.

[2]. Nogues; J.-L.; Balaban; C.; Moreshead; W. V. U.S. Pat. No. 5,076,980 (to Geltech), 1991.

[3]. Premstaller, A.; Huber, C.; Oberarcher, H. World Patent Application WO0155713, Method and Apparatus for Separating Polynucleotides Using Monolithic Capillary Columns.

[4]. Control of pore size in macroporous sol gels: Tanaka, N.; Nagayama, H.; Kobayashi, H.; Ikegami, T.; Hosoya, K.; Ishizuka, N.; Minakuchi, H.; Nakanishi, K.; Cabrera, K.; Lubda, D. Monolithic Silica Columns for HPLC, Micro-HPLC, and CEC *J. High Resol. Chromatogr.* 2000, 23, 111-116.

[5]. (a) Merck column; http://www.chromolith.com/english/services/chromatographie/hplc/chromolith/intro.html. (b) Nakanishi; K.; Soga; N.; Minakuchi; T. PCT publication number WO98/29350 (to Merck Patent GmbH), 1998.

[6]. Brook, M. A.; Brennan, J. D.; Chen, Y. *Polyol-Modified Silanes as Precursors for Silica*, U.S. Provisional Patent Ser. No. 60/384,084 (to McMaster University), Filed May 31, 2002 and PCT Patent Application S.N. PCT/CA03/00790, Filed Jun. 2, 2003, Published as WO 03/102001 on Dec. 11, 2003.

[7]. Kikuta, K.; Ohta, K.; Takagi, K. Synthesis of Transparent Magadiite-Silica Hybrid Monoliths *Chem. Mater.* 2002, 14, 3123-3127.

[8]. Kang, J.; Wistuba, D.; Schurig, V. A silica monolithic column prepared by the sol-gel process for enantiomeric separation by capillary electrochromatography *Electrophoresis* 2002, 23, 1116-1120.

[9]. Pope, E. J. A.; Sano, Y.; Wang, S.; Sarkar, A. U.S. Pat. No. 5,023,208 (to Orion Laboratories Inc.), 1991.

[10]. Ishizuka, N.; Minakuchi, H.; Nakanishi, K.; Hirao, K.; Tanaka, N. Chromatographic characterization of macroporous monolithic silica prepared via sol-gel process *Coll. Surf. A: Physicochem. Eng. Asp.* 2001, 187488, 273-279. (b) Ishizuka, N., Minakuchi, H., Nakanishi, K., Soga, N., Nagayama, H., Hosoya, K., Tanaka, N. Performance of a Monolithic Silica Column in a Capillary under Pressure-Driven and Electrodriven Conditions. *Anal. Chem.* 2000, 72, 1275-1280 and references cited therein.

[11]. Nakanishi, K.; Soga, N.; Minakuchi, K. U.S. Pat. No. 6,531,060, Issued Mar. 11, 2003; Nakanishi, K.; Soga, N.; Minakuchi, K. U.S. Pat. No. 6,207,098, Issued Mar. 27, 2001; Nakanishi, K.; Soga, N.; U.S. Pat. No. 5,624,875, Issued Apr. 29, 1997.

[12]. (a) Brinker, C. J.; Scherer, G. W. *Sol-Gel Science*, Academic Press: San Diego, 1990. (b) Iler, R. K. *The Chemistry of Silica*, Wiley: New York, 1979. (c) Brook, M. A. *Silicon in Organic, Organometallic, and Polymer Chemistry*, Wiley: New York, 2000, Chap 10.

[13]. a) Hage, D. S. Survey of recent advances in analytical applications of immunoaffinity chromatography *J. Chromatog. B,* 1998, 715, 3-28 b) Hage, D. S.; Affinity Chromatography: A Review of Clinical Applications *Clin. Chem.* 1999, 45, 593-615; c) Weller, M. G; Immunochromatography c techniques—a critical review *Fresenius J. Anal. Chem.* 2000, 366, 635-645; d) Muronetz, V. I.; Sholukh, M.; Korpela, T. Use of protein-protein interactions in affinity chromatography *J. Biochem. Biophys. Methods* 2001, 49, 29-47; e) Baczek, T.; Kaliszan, R. Quantitative structure/retention relationships in affinity chromatography. *J. Biochem. Biophys. Methods* 2001, 49, 83-98; f) Burgess, R. R.; Thompson, N. E. Advances in gentle immunoaffinity chromatography. *Curr. Opin. Biotechnol.* 2002, 13, 304-308.

[14]. a) Hage, D. S.; Noctor, T. A. G.; Wainer, I. W. Characterization of the protein binding of chiral drugs by high-performance affinity chromatography interactions of R- and S-ibuprofen with human serum albumin. *J. Chromatogr. A,* 1995, 693, 23-32; b) Hofstetter, H.; Hofstetter, O. Schurig, V. Enantiomer separation using BSA as chiral stationary phase in affinity OTEC and OTLC. *J. Microcolumn Sep.* 1998, 10, 287-291; c) Hofstetter, O.; Lindstrom, H.; Hofstetter, H. Direct Resolution of Enantiomers in High-Performance Immunoaffinity Chromatography under Isocratic Conditions *Anal. Chem.* 2002, 74, 2119-2125. d) Fitos, I.; Visy, J.; Simonyi, M. Species-dependency in chiral-drug recognition of serum albumin studied by chromatographic methods. *J. Biochem. Biophys. Methods* 2002, 54, 71-84.

[15]. a) Hsieh, Y. L.; Wang, H.; Elicone, C.; Mark, J.; Martin, S. A.; Regnier, F. Automated Analytical System for the Examination of Protein Primary Structure *Anal. Chem.,* 1996, 68, 455-462; b) Wang, C.; Oleschuk, R.; Ouchen, F.; Li, J.; Thibault, P.; Harrison, D. J. Integration of immobilized trypsin bead beds for protein digestion within a microfluidic chip incorporating capillary electrophoresis separations and an electrospray mass spectrometry interface *Rapid. Commun. Mass. Spectrom.* 2000, 14, 1377-1383; c) Wang, S.; Regnier, F. E. Proteolysis of whole cell extracts with immobilized enzyme columns as part of multidimensional chromatography *J. Chromatogr. A* 2001, 913, 429-436; d) Peterson, D. S.; Rohr, T.; Svec, F.; Frechet, J. M. J. High-Throughput Peptide Mass Mapping Using a Microdevice Containing Trypsin Immobilized on a Porous Polymer Monolith Coupled to MALDI TOF and ESI TOF Mass Spectrometers *J. Proteome Res.* 2002, 1, 563-568; e) Peterson, D. S.; Rohr, T.; Svec, F.; Frechet, J. M. J. Enzymatic Microreactor-on-a-Chip: Protein Mapping Using Trypsin Immobilized on Porous Polymer Monoliths Molded in Channels of Microfluidic Devices. *Anal. Chem.* 2002, 4081-4088; f) Slysz, G. W.; Schriemer, D. C. On-column digestion of proteins in aqueous-organic solvents *Rapid Commun. Mass Spec.* 2003, 7, 1044-1050.

[16]. Prazeres, D.; Miguel F.; Cabral, J. M. S. in: *Multiphase Bioreactor Design*, Cabral, J. M. S.; Mota, M.; Tramper, J. (Eds.) Taylor & Francis Ltd., London, UK, 2001, pp. 135-180.

[17]. a) Schriemer, D. C.; Bundle, D. R.; Li, L.; Hindsgaul, O. Micro-Scale Frontal Affinity Chromatography with Mass Spectrometric Detection: A New Method for the Screening of Compound Libraries *Angew. Chem., Int. Ed. Engl.* 1998, 37, 3383-3387; b) Zhang, B.; Palcic, M. M.; Schriemer, D. C.; Alvarez-Manilla, G.; Pierce, M.; Hindsgaul, O. Frontal Affinity Chromatography Coupled to Mass Spectrometry for Screening Mixtures of Enzyme Inhibitors. *Anal. Biochem.* 2001, 299, 173-182.

[18]. a) Baynham, M. T.; Patel, S.; Moaddel, R.; Wainer, I. W.; Multidimensional on-line screening for ligands to the α3β4 neuronal nicotinic acetylcholine receptor using an immobilized nicotinic receptor liquid chromatographic stationary phase *J. Chromatogr. B* 2002, 772, 155-161; b) Moaddel, R.; Lu, L.; Baynham, M.; Wainer, I. W. Immobilized receptor- and transporter-based liquid chromatographic phases for on-line pharmacological and biochemical studies: a mini-review *J. Chromatogr. B* 2002, 768, 41-53; c) Moaddel, R.; Cloix, J.-F.; Ertem, G.; Wainer, I. W. Multiple Receptor Liquid Chromatographic Stationary Phases: The Co-Immobilization of Nicotinic Receptors, _-Amino-Butyric Acid Receptors, and N-Methyl D-Aspartate Receptors *Pharmaceut. Res.* 2002, 19, 104-107; d) Moaddel, R.; Wainer, I. W.; Immobilized nicotinic receptor stationary phases: going with the flow in high-throughput screening and pharmacological studies *J. Pharmaceut. Biomed. Anal.* 2003, 30, 1715-1724.

[19]. Seemann, H.; Winter, R.; Royer, C. A. Volume, expansivity and isothermal compressibility changes associated with temperature and pressure unfolding of staphylococcal nuclease *J. Molec. Biol.* 2001, 307, 1091-1102.

[20]. Gill, I., Bio-doped Nanocomposite Polymers: Sol-Gel Bioencapsulates. *Chem. Mater.* 2001, 13, 3404-3421.

[21]. Jin, W.; Brennan, J. D. Properties and applications of proteins encapsulated within sol-gel derived materials *Anal. Chim. Acta* 2002, 461, 1-36.

[22]. Zheng, L.; Reid, W. R.; Brennan, J. D. Measurement of Fluorescence from Tryptophan To Probe the Environment and Reaction Kinetics within Protein-Doped Sol-Gel-Derived Glass Monoliths. *Anal. Chem.* 1997, 69, 3940-3949.

[23]. Zheng, L.; Brennan, J. D. Measurement of intrinsic fluorescence to probe the conformational flexibility and thermodynamic stability of a single tryptophan protein entrapped in a sol-gel derived glass matrix *Analyst* 1998, 123, 1735-1744.

[24]. Edmiston, P. L.; Wambolt, C. L.; Smith, M. K.; Saavedra, S. S. Spectroscopic Characterization of Albumin and Myoglobin Entrapped in Bulk Sol-Gel Glasses *J. Coll. Int. Sci.* 1994, 163, 395-406.

[25]. Jordan, J. D.; Dunbar, R. A.; Bright, F. V. Dynamics of Acrylodan-Labeled Bovine and Human Serum Albumin Entrapped in a Sol-Gel-Derived Biogel *Anal. Chem.* 1995, 67, 2436.

[26]. Gottfried, D. S.; Kagan, A.; Hoffman, B. M.; Friedman, J. M. Impeded Rotation of a Protein in a Sol-Gel Matrix *J. Phys. Chem. B* 1999, 103, 2803-2807.

27. Doody, M. A.; Baker, G. A.; Pandey, S.; Bright, F. V. Affinity and Mobility of Polyclonal Anti-Dansyl Antibodies Sequestered within Sol-Gel-Derived Biogels *Chem. Mater.* 2000, 12, 1142.

28. Wambolt, C. L.; Saavedra, S. S. Iodide Fluorescence Quenching of Sol-Gel Immobilized BSA. *J. Sol-Gel Sci. Tech.* 1996, 7, 53-57.

29. Shen, C.; Kostic, N. M. Kinetics of Photoinduced Electron-Transfer Reactions within Sol-Gel Silica Glass Doped with Zinc Cytochrome c. Study of Electrostatic Effects in Confined Liquids *J. Amer. Chem. Soc.* 1997, 119, 1304-1312.

30. a) Braun, S.; Shtelzer, S.; Rappoport, S.; Avnir, D.; Ottolenghi, M. Biocatalysis by sol-gel entrapped enzymes *J. Non-Cryst. Solids,* 1992, 147, 739-743; b) Avnir, D.; Braun, S.; Lev, O.; Ottolenghi, M. Enzymes and Other Proteins Entrapped in Sol-Gel Materials *Chem. Mater.* 1994, 6, 1605-1614; c) Wang, R.; Narang, U.; Prasad, P. N.; Bright, F. V. Affinity of antifluorescein antibodies encapsulated within a transparent sol-gel glass *Anal. Chem.* 1993, 65, 2671-2675; d) Ellerby, L. M.; Nishida, C. R.; Nishida, F.; Yamanaka, S. A.; Dunn, B.; Valentine, J. S.; Zink, J. I. Encapsulation of Proteins in Transparent Porous Silicate Glasses Prepared by the Sol-Gel Method *Science,* 1992, 225, 1113-1115; e) Wu, S.; Ellerby, L. M.; Cohan, J. S.; Dunn, B.; El-Sayed, M. A.; Valentine, J. S.; Zink, J. I. Bacteriorhodopsin encapsulated in transparent sol-gel glass: a new biomaterial *Chem. Mater.* 1993, 5, 115-120; f) Dave, B. C.; Soyez, H.; Miller, J. M.; Dunn, B.; Valentine, J. S.; Zink, J. I. Synthesis of Protein-Doped Sol-Gel SiO2 Thin Films: Evidence for Rotational Mobility of Encapsulated Cytochrome c *Chem. Mater.* 1995, 7, 1431-1434; g) Yamanaka, S. A.; Nishida, F.; Ellerby, L. M.; Nishida, C. R.; Dunn, B.; Valentine, J. S.; Zink, J. I. Enzymatic activity of glucose oxidase encapsulated in transparent glass by the sol-gel method *Chem. Mater.* 1992, 4, 495-497; h) Dave, B. C.; Dunn, B.; Valentine, J. S.; Zink, J. I. Sol-Gel Encapsulation Methods for Biosensors. *Anal. Chem.* 1994, 66, 1120A-1127A; i) Blyth, D. J.; Aylott, J. W.; Richardson, D. J.; Russell, D. A. Sol-gel encapsulation of metalloproteins for the development of optical biosensors for nitrogen monoxide and carbon monoxide *Analyst* 1995, 120, 2725-2730; j) Aylott, J. W.; Richardson, D. J.; Russell, D. A. Optical Biosensing of Nitrate Ions Using a Sol-Gel Immobilized Nitrate Reductase *Analyst* 1997, 122, 77-80; k) Williams, A. K.; Hupp, J. T. Sol-Gel-Encapsulated Alcohol Dehydrogenase as a Versatile, Environmentally Stabilized Sensor for Alcohols and Aldehydes. *J. Am. Chem. Soc.* 1998, 120, 4366-4371.

31. a) Braun, S.; Rappoport, S.; Zusman, R.; Avnir, D.; Ottolenghi, M. Biochemically active sol-gel glasses: the trapping of enzymes *Mater. Lett.* 1990, 10, 1-5; b) Heichal-Segal, O.; Rappoport, S.; Braun, S. Immobilization in alginate-silicate sol-gel matrix protects b-glucosidase against thermal and chemical denaturation. *Biotechnology,* 1995, 13, 798-800; c) Reetz, M. T.; Zonta, A.; Simpelkamp, J.; Efficient immobilization of lipases by entrapment in hydrophobic sol-gel materials *Biotechnol. Bioengin.* 1996, 49, 527-534; d) Narang, U.; Prasad, P. N.; Bright, F. V.; Kumar, K.; Kumar, N. D.; Malhotra, B. D.; Kamalasanan, M. N.; Chandra, S. A Novel Protocol to Entrap Active Urease in a Tetraethoxysilane-Derived Sol-Gel Thin-Film Architecture *Chem. Mater.* 1994, 6, 1596-1598; e) Narang, U.; Prasad, P. N.; Bright, F. V.; Ramanathan, K.; Kumar, N. D.; Malhotra, B. D.; Kamalasanan M. N.; Chandra, S. Glucose Biosensor Based on a Sol-Gel-Derived Platform. *Anal. Chem.* 1994, 66, 3139-3144; f) Jordan, J. D.; Dunbar, R. A.; Bright, F. V.; Aerosol-generated sol-gel-derived thin films as biosensing platforms. *Anal. Chim. Acta* 1996, 332, 83-91; g) Yamanaka, S. A.; Dunn, B.; Valentine, J. S.; Zink, J. I. Nicotinamide Adenine Dinucleotide Phosphate Fluorescence and Absorption Monitoring of Enzymic Activity in Silicate Sol-Gels for Chemical Sensing Applications *J. Am. Chem. Soc.* 1995, 117, 9095-9096; h) Kauffmann, C.; Mandelbaum, R. T.; Entrapment of atrazine chlorohydrolase in sol-gel glass matrix. *J. Biotechnol.* 1998, 62, 169-176.

32. a) Bronshtein, A.; Aharonson, N.; Avnir, D.; Turniansky, A.; Altstein, M. Sol-Gel Matrixes Doped with Atrazine Antibodies: Atrazine Binding Properties *Chem. Mater.* 1997, 9, 2632-2639; b) Altstein, M.; Bronshtein, A.; Glattstein, B.; Zeichner, A.; Tamiri, T.; Almong, J. Immunochemical Approaches for Purification and Detection of TNT Traces by Antibodies Entrapped in a Sol-Gel Matrix *Anal. Chem.* 2001, 73, 2461-2467; c) Bronshtein, A.; Aharonson, N.; Turniansky, A.; Altstein, M. Sol-Gel-Based Immunoaffinity Chromatography Application to Nitroaromatic Compounds *Chem. Mater.* 2000, 12, 2050-2058; d) Cichna, M.; Knopp, D.; Niessner, R. Immunoaffinity chromatography of polycyclic aromatic hydrocarbons in columns prepared by the sol-gel method *Anal. Chim. Acta* 1997, 339, 241-250; e) Cichna, M.; Markl, P.; Knopp, D.; Niessner, R. Optimization of the Selectivity of Pyrene Immunoaffinity Columns Prepared by the Sol-Gel Method *Chem. Mater.* 1997, 9, 2640-2646; f) Schedl, M.; Wilharm, G.; Achatz, S.; Kettrup, A.; Niessner, R.; Knopp, D. Monitoring Polycyclic Aromatic Hydrocarbon Metabolites in Human Urine: Extraction and Purification with a Sol-Gel Glass Immunosorbent. *Anal. Chem.* 2001, 73, 5669-5676; g) Spitzer, B.; Cichna, M.; Markl, P.; Sontag, G.; Knopp, D.; Niessner, R. Determination of 1-nitropyrene in herbs after selective enrichment by a sol-gel-generated immunoaffinity column. *J. Chromatogr. A* 2000, 880, 113.

33. Cichna, M. Applicability of Enzyme Columns Prepared by Co-Immobilising_-Glucuronidase and Arylsulfatase by the Sol-Gel Method for Deconjugation of Glucuronides and Sulfates in Urine. *J. Sol-Gel Sci. Technol.* 2003, 26, 1159-1164.

34. Zusman R.; Zusman, I. Glass fibers covered with sol-gel glass as a new support for affinity chromatography columns: a review *J. Biochem. Biophys. Methods* 2001, 49, 175-187.

35. a) Sakai-Kato, K.; Kato, M.; Toyo'oka, T. On-Line Trypsin-Encapsulated Enzyme Reactor by the Sol-Gel Method Integrated into Capillary Electrophoresis *Anal. Chem.* 2002, 74, 2943-2949; b) Kato, M.; Sakai-Kato, K.; Matsumoto, N.; Toyo'oka, T. A Protein-Encapsulation Technique by the Sol-Gel Method for the Preparation of Monolithic Columns for Capillary Electrochromatography *Anal. Chem.* 2002, 74, 1915-1921; c) Sakai-Kato, K.; Kato, M.; Toyo'oka, T. On-line drug-etabolism system using microsomes encapsulated in a capillary by the sol-gel method and integrated into capillary electrophoresis. *Anal. Biochem.* 2002, 308, 278-284; d) Sakai-Kato, K.; Kato, M.; Nakakuki, H.; Toyo'oka, T. Investigation of structure and enantioselectivity of BSA-encapsulated sol-gel columns prepared for capillary electrochromatography. *J. Pharmaceut. Biomed. Anal.* 2003, 31, 299-309; e) Sakai-Kato, K; Kato, M.; Toyo'oka, T. Creation of an On-Chip Enzyme Reactor by Encapsulating Trypsin in Sol-Gel on a Plastic Microchip *Anal. Chem.* 2003, 75, 388-393; f) Kato, M.; Matsumoto, N.; Sakai-Kato, K.; Toyo'oka, T. Investigation of chromatographic performances and binding characteristics of BSA-encapsulated capillary column prepared by the sol-gel method. *J. Pharmaceut. Biomed. Anal.* 2003, 30, 1845-1850.

[36]. Macbeath, G.; Schreiber, S. L. Printing proteins as microarrays for high-throughput function determination. *Science* 2000, 289, 1760-1763.

[37]. (a) Gluconamides: (i) DePasquale, R. J.; Wilson, M. E. U.S. Pat. No. 4,591,652 (to SCM Corp., USA), 1986. (ii) Haupt, M.; Knaus, S.; Rohr, T.; Gruber, H. Carbohydrate modified polydimethylsiloxanes part 1. Synthesis and characterization of carbohydrate silane and siloxane building blocks *J. Macromol. Sci., Part A: Pure Appl. Chem.* 2000, A37, 323-341. (b) A related compound, the maltopentaose-modified silane: Enomoto, N.; Furukawa, S.; Ogasawara, Y.; Akano, H.; Kawamura, Y.; Yashima, E.; Okamoto, Y. Preparation of Silica Gel-Bonded Amylose Through Enzyme-Catalyzed Polymerization and Chiral Recognition Ability of Its Phenylcarbamate Derivative in HPLC. *Anal. Chem.* 1996, 68, 2798-2804.

[38]. Brook, M. A. *Silicon in Organic, Organometallic, and Polymer Chemistry*, Wiley: New York, 2000, Chap. 1.

[39]. Flora, K. K.; Brennan, J. D.; Baker, G. A.; Doody, M. A.; Bright, F. V. Unfolding of Acrylodan-Labelled Human Serum Albumin Probed by Steady-State and Time-Resolved Fluorescence Methods *Biophys. J.* 1998, 75, 1084-1096.

[40]. a) Glickman, J. F.; Wu, X.; Mercuri, R.; Illy, C.; Bowen, B. R.; He, Y.; Sills, M. J. A Comparison of ALPHAScreen, TR-FRET, and TRF as Assay Methods for FXR Nuclear Receptors *Biomolec. Screen.* 2002, 7, 3-10. b) Perkin-Elmer Application Note, How to optimize a Tyrosine Kinase assay using time resolved fluorescence-based LANCE detection.

[41]. St ver, H. D. H.; Li, K. *Dispersion Polymerization*, in Polymeric Materials Encyclopedia, Salamone, J. C., Ed. CRC Press: Boca Raton, Fla. USA, 1996, Vol. 3, pp. 1900.

[42]. Brennan, J.; Rupcich, N. *Multicomponent Protein Microarrays*, U.S. Provisional Patent Application Ser. No. 60/422,892, filed Nov. 1, 2002.

[43]. Besanger, T. R.; Chen, Y.; Deisingh, A. K.; Hodgson, R.; Jin, W.; Mayer, S.; Brook, M. A.; Brennan, J. D. Screening of Inhibitors Using Enzymes Entrapped in Sol-Gel-Derived Materials *Anal. Chem.* 2003, 75, 2382-2391.

[44]. Brook, M. A.; Chen, Y.; Guo, K.; Zhang, Z.; Jin, W.; Deisingh, A.; Cruz-Aguado, J.; Brennan, J. D. Proteins Entrapped in Silica Monoliths Prepared from Glyceroxysilanes. *J. Sol-Gel Sci. Technol.* 2004, in press.

[45]. Hitchings, G. H. Selective inhibitors of dihydrofolate reductase. *Angew. Chem. Int. Ed. Engl.* 1989, 29, 879-889.

[46]. Stone, S. R.; Morrison, J. F. Dihydrofolate reductase from *Escherichia coli*: the kinetic mechanism with NADPH and reduced acetylpyridine adenine dinucleotide phosphate as substrates. *Biochemistry* 1988, 27, 5493-5499.

[47]. Benkovic, S. J.; Fierke, C. A.; Naylor, A. M. Insights into Enzyme Function From Studies on Mutants of Dihydrofolate Reductase *Science* 1988, 239, 1105-1110.

[48]. Polshakov, V. I.; Biekofsky, R. R.; Birdsall, B.; Feeney, J. Towards understanding the origins of the different specificities of binding the reduced (NADPH) and oxidised ($NADP^+$) forms of nicotinamide adenine dinucleotide phosphate coenzyme to dihydrofolate reductase. *J. Mol. Struct.* 2002, 602-603, 257-267.

[49]. Brennan, J. D.; Brook, M. A. and Besanger, T. *Method of Immobilizing Membrane-Associated Molecules*, U.S. Provisional Patent Application Ser. No. 60/426,018 (to McMaster University) Filed Nov. 14, 2002.

[50]. Zhang, T.; Marchant, R. E. Novel Polysaccharide Surfactants; Synthesis of Model Compounds and Dextran Based Surfactants. *Macromolecules* 1994, 27, 7302-7308.

[51]. Zelisko, P. M.; Brook, M. A. Stabilization of α-Chymotrypsin and Lysozyme Entrapped in Water-in-Silicone Oil Emulsions. *Langmuir* 2002, 18, 8982-8987.

[52]. (a) Lin, Y.; Hlady, V Human serum albumin adsorption onto octadecyldimethylsilyl-silica gradient surface. *Colloids Surf*, B 1994, 2, 481-491. (b) Hasegawa, M.; Gitano, H. Adsorption kinetics of proteins onto polymer surfaces as studied by the multiple internal reflection fluorescence method. *Langmuir* 1992, 8, 1582-1586.

[53]. Zolli-Juran, M.; Cechetto, J. D.; Harlen, H.; Daigle, D. M.; Brown, E. D. *Bioorg. Med. Chem. Lett.* 2003, 13, 2493.

[54]. Barrett, E. P.; Joyner, L. G. Halenda, P. H. The Determination of Pore Volume and Area Distributions in Porous Substances. I. Computations from Nitrogen Isotherms *J. Amer. Chem. Soc.* 1951, 73, 373-380.

[55]. Livage, J.; Coradin, T.; Roux, C. Encapsulation of biomolecules in silica gels. *J. Phys.: Condens. Matter* 2001, 13, R673.

[56]. D. Tleugabulova, Z. Zhang, Y. Chen, M. A. Brook and J. D. Brennan*. Fluorescence Anisotropy in Studies of Solute Interactions with Covalently Modified Colloidal Silica Nanoparticles. *Langmuir,* 2004, 20, 848-854.

[57]. Iwakura, M.; Honda, S. Stability and reversibility of thermal denaturation are greatly improved by limiting terminal flexibility of *Escherichia coli* dihydrofolate reductase *J. Biochem.* 1996, 119, 414-420.

[58]. T. Besanger and J. D. Brennan. Entrapment of Functional Nicotinic Acetylcholine Receptor in Macroporous Sol-Gel Derived Materials. *Angewandte Chimie,* 2004, submitted by Mar. 12, 2004.

[59]. Al-Obeidi, F. A.; Wu, J. J.; Lam, K. S. Protein tyrosine kinases: structure, substrate specificity, and drug discovery. Biopolymers, 1998, 47, 197-223.

[60]. Badjic, J. D; Kostic, N. M. Behavior of organic compounds confined in monoliths of sol-gel silica glass. Effects of guest-host hydrogen bonding on uptake, release, and isomerization of the guest compounds. *J. Mater. Chem.* 2001, 11, 408-418.

[61]. Badjic, J. D; Kostic, N. M. Unexpected Interactions between Sol-Gel Silica Glass and Guest Molecules. Extraction of Aromatic Hydrocarbons into Polar Silica from Hydrophobic Solvents. *J. Phys. Chem. B* 2000, 104, 11081-11087.

[62]. Eggers, D. K.; Valentine, J. S. *J. Mol. Biol.* 2001, 314, 911.

[63]. Brennan, J. D.; Benjamin, D.; Dibattista, E.; Gulcev. M. D. Using Sugar and Amino Acid Additives to Stabilize Enzymes within Sol-Gel Derived Silica *Chem. Mater Chem. Mater.* 2003, 15, 737-745.

[64]. Henzl, M. T.; Hapak, R. C.; Goodpasture, E. A. Introduction of a Fifth Carboxylate Ligand Heightens the Affinity of the Oncomodulin CD and EF Sites for $Ca^{2+}$ *Biochem.* 1996, 35, 5856-5959.

[65]. Zheng, L.; Hogue, C. W. V.; Brennan, J. D. Effects of metal binding affinity on the chemical and thermal stability of site-directed mutants of rat oncomodulin. *Biophys. Chem.* 1998, 71, 157-172.

[66]. Zheng, L.; Flora, K.; Brennan, J. D. Improving the Performance of a Sol-Gel-Entrapped Metal-Binding Pro- 67. K. K. Flora and J. D. Brennan*. Fluorimetric Detection of $Ca^{2+}$ Based on an Induced Change in the Conformation of Sol-Gel Entrapped Parvalbumin. *Analytical Chemistry* 1998, 70, 4505-4513.

68. Flora, K. K.; Brennan, J. D. Effect of Matrix Aging on the Behavior of Human Serum Albumin Entrapped in a Tetraethyl Orthosilicate-Derived Glass *Chem. Mater.* 2001, 13, 4170-4179.

69. Tian, M. C.; Smith, A. A.; Knight, W. B. Structural Determinants for Potent, Selective Dual Site Inhibition of Human $pp60^{c-src}$ by 4-Anilinoquinazolines. *Biochemistry* 2001, 40, 7084.

70. Ferrer, M. L.; del Monte, F.; Levy, D. A Novel and Simple Alcohol-Free Sol-Gel Route for Encapsulation of Labile Proteins *Chem. Mater.* 2002, 14, 3619-3621.

71. Bhatia, R. B.; Brinker, C. J.; Gupta, A. K.; Singh, A. K. Aqueous Sol-Gel Process for Protein Encapsulation. *Chem. Mater.* 2000, 12, 2434-2441.

72. Eu. J.; Andrade, J. Properties of firefly luciferase immobilized through a biotin carboxyl carrier protein domain *Luminescence* 2001, 16, 57-63.

73. Carrea, G.; Bovara, R.; Girotti, S.; Ferri, E.; Ghini, S.; Roda, A. Continuos-flow bioluminescent determination of ATP in platelets using firefly luciferase immobilized on epoxy methacrylate. *J. Biolumin. Chemilumin.* 1989, 3, 7-11.

74. Ugarova, N. N.; Brovko, L. Y.; Kost, N. V. Immobilization of luciferase from firefly Luciola mingrelica-catalytic properties and stability of the immobilized enzyme. *Enz Biochem. Biotech.* 1982, 4, 224-228.

75. Filippova, N. Yu.; Dukhovich, A. F.; Ugarova, N. N. New approaches to the preparation and application of firefly luciferase *J. Biolumin. Chemilumin.* 1989, 4, 419-422.

TABLE 1

Preparation of TQ resins

| Sample | Ratio of DGS: Gluconamide-Si(OEt)$_3$ (w/w) | Gelation time (min)[b] | Aged (days) | Yield (g) |
|---|---|---|---|---|
| 6 | 1:0 | 10 | 7 | 0.071 |
| 7 | 4:0:1[a] | 60 | 7 | 0.076 |
| 8 | 4:1 | 65 | 7 | 0.099 |
| 9 | 3:1 | 70 | 7 | 0.128 |
| 10 | 2:1 | 90 | 20 | 0.138 |
| 11 | 1:1 | 90 | 20 | 0.173 |

| Sample | Ratio of DGS: Maltonamide-Si(OEt)$_3$ (w/w) | Gelation time (min)[b] | Aged (days) | Yield (g) |
|---|---|---|---|---|
| 12 | 16:0:1[c] | 55 | 7 | 0.070 |
| 13 | 16:1 | 60 | 7 | 0.081 |
| 14 | 8:1 | 70 | 7 | 0.093 |
| 15 | 4:1 | 70 | 7 | 0.110 |

[a]Although no trialkoxysilane was present, there was a 4:1 ratio of DGS:sorbitol.
[b]Refers to the time when the solution ceases to flow after addition of the buffer solution, as judged by repeatedly tilting a test-tube containing the sol until gelation occurred
[c]Although no trialkoxysilane was present, there was a 16:1 ratio of DGS:Maltose.

TABLE 2

Solid-state $^{13}C$ and $^{29}Si$ CPMAS NMR spectral data of samples 8 and 15

| Sample | $^{13}C$ (δ, ppm) | $^{29}Si$ (δ, ppm) |
|---|---|---|
| 8 | 9.8, 22.8, 41.9, 63.4, 72.7, 174.5 | −66.1, −101.2, −110.5 |
| 15 | 9.3, 22.2, 41.9, 63.4, 72.9, 102.6, 174.8 | −67.2, −101.4, −109.8 |

TABLE 3

Mean Mobilities [25° C., (μ/s)/(V/cm)] of samples 6-11.

| Sample | 6 | 7 | 8 | 9 | 10 | 11 |
|---|---|---|---|---|---|---|
| 1 mM PBS[a] (pH = 8) | −3.20 | −3.17 | −4.08 | −4.05 | −2.89 | −3.16 |
| 25 mM Tris buffer (pH = 8) | −2.25 | −2.22 | −2.89 | −2.97 | −2.56 | −1.49 |

[a]PBS = phosphate buffer

TABLE 4

Timing for Gelation ($t_{gel}$) Phase Separation ($t_{ps}$) as a Function of Sol Constituents

| Gel Materials | Gelation Time ($t_{gel}$) | Phase Separation time ($t_{ps}$) |
|---|---|---|
| 0.5 g DGS, 500 μL H$_2$O, 500 μL Tris buffer | 39 min | never |
| 0.5 g of 0.0259 g/mL PEG (MW 100,000) replacing Tris buffer | 11 min | 6 min |
| 0.5 g of 0.05 g/mL PEG (MW 100,000) replacing Tris buffer | 7 min | 5 min |
| 0.5 g MSS,[a] 800 μL H$_2$O, 800 μL Tris buffer | >12 h | never |
| 500 μL PolyNIPAM[b] solution replacing Tris buffer | 69 min | 16 min |

[a]Monosorbitylsilane
[b]Poly(N-isopropylacrylamide)

TABLE 5

BET results of DGS/PEO gel

| Surface Area Data (m$^2$/g) | Multi-point BET area | 550 |
|---|---|---|
| | Langmuir surface area | 1456 |
| Pore Volume Data (cm$^3$/g) | Total pore volume | 0.4585 (d < 193.03 nm) |
| Pore Size Data | Average pore diameters (nm) | 3.329 |

0.5 g DGS/500 μL H$_2$O/500 μL PEO solution (0.05 g/1000 μL)
The sample was crushed, then washed three times with water for 3 days (each time more than 20 mL water). The sample was freeze dried over 24 hours, then degassed at 100° C. for 6 hours before measurement.

TABLE 6

Residual PEO in DGS-derived silica

| PEO/Sol (2 K[a])g/ml | PEO wt. % Cal.[b] | TGA[c] | PEG/Sol (10 K[a])g/ml | PEO wt. % Cal. | TGA | PEO/Sol (100 K[a])g/ml | PEO wt. % Cal. | TGA |
|---|---|---|---|---|---|---|---|---|
| 0.05 | 24.1 | 25 | 0.025 | 14.2 | 17 | 0.005 | 3.3 | 8 |
| 0.15 | 45.4 | 34 | 0.035 | 20.5 | 23 | 0.015 | 9.1 | 12 |
| 0.25 | 55.0 | 39 | 0.05 | 24.2 | 29 | 0.025 | 14.0 | 19 |
| 0.35 | 60.8 | 23 | 0.15 | 45.2 | 33 | 0.035 | 18.0 | 21 |
| 0.45 | 64.4 | 32 | 0.25 | 54.6 | 34 | 0.05 | 23.6 | 25 |

[a]Refers to MW of the PEO;
[b]Calculated based on PEO added;
[c]Measured using thermogravimetric analysis

TABLE 7

Protein removed by washing silica gel after cure: Gel entrapped with HSA

| Additive to DGS sol | 1st washing (µg/mL) | 2nd washing (µg/mL) | 3rd washing (µg/mL) |
|---|---|---|---|
| PEO 10K | 77.3 | 54.6 | 7.26 |
| PEO 100K | 98.7 | 4.54 | 0.15 |
| PEO-NH₂ | 117 | 28.3 | 1.34 |
| PEO 10K/PPG-NH₂ 200 | 0 | 0 | 0 |
| PEO 10K/PPG-NH₂ 400 | 0 | 0 | 0 |
| PEO 10K/PAM 17K | 49.4 | 0 | 0 |
| PEO 10K/PAM 65K | 48.2 | 0 | 0 |
| Gluconamide-Si | 0.270 | 0.156 | 0.113 |
| Methyltriethoxysilane | 0.135 | 0.0754 | 0.0704 |
| Phenyltriethoxysilane | 0.428 | 0.0903 | 0.102 |

TABLE 8

Protein removed by washing silica gel after cure: Gel entrapped with Lysozyme

| Additive to DGS sol | 1st washing (µg/mL) | 2nd washing (µg/mL) | 3rd washing (µg/mL) |
|---|---|---|---|
| PEO 10K | 3.48 | 3.48 | 1.38 |
| PEO 100K | 6.43 | 0.41 | 0.77 |
| PEO-NH₂ | 23.0 | 6.11 | 1.26 |
| PEO 10K/PPG-NH₂ 200 | 0 | 0 | 0 |
| PEO 10K/PPG-NH₂ 400 | 0 | 0 | 0 |
| PEO 10K/PAM 17K | 1.59 | 0.14 | 0 |
| PEO 10K/PAM 65K | 1.17 | 0.16 | 0 |
| Gluconamide-Si | 0.181 | 0.124 | 0.0828 |
| Methyltriexthoxysilane | 0.199 | 0.102 | 0.100 |
| Phenyltriethoxysilane | 0.231 | 0.156 | 0.085 |

TABLE 9

Solutions used to prepare gels from DGS/PEO and PPG-NH₂

| Vial # | PEO (10K[a]) 5 g dissolved in 10 mL PBS (pH 8.00, 10 mM)/µl | 0.5 g PPG-NH₂ 200[a] (molecular weight)/ 1 mL water/µl | 0.1 g PPG-NH₂ 400[a] (molecular weight)/ 1 mL water/µl |
|---|---|---|---|
| 1 | 1000 | 1 | — |
| 2 | 1000 | 5 | — |
| 3 | 1000 | 10 | — |
| 4 | 1000 | — | 10 |
| 5 | 1000 | — | 50 |
| 6 | 1000 | — | 100 |

[a]refers to molecular weight

TABLE 10

Gels prepared from DGS/PEO and PPG - DGS recipe.

| Vial | Polymer mixture (refer Table 9 above) µl | Gel time |
|---|---|---|
| 1 | 60 | ~60 min |
| 2 | 60 | ~40 min |
| 3 | 60 | ~13 min |
| 4 | 60 | ~42 min |
| 5 | 60 | ~6 min |
| 6 | 60 | ~2 min |

TABLE 11

Mercury intrusion porosimetry data for macroporous silica samples used for column development. All samples contain 8 wt % of polymer.

| Sample | Total Pore Volume (cm³) | Throughpore Volume (cm³) | Bulk (Particle) Density (g/cm³) | Interparticle Porosity (Throughpores) | Intraparticle Porosity (Mesopores) | Average Macropore diameter (µm) |
|---|---|---|---|---|---|---|
| DGS + PEO 2 kDa | 2.28 | 0.15 | 0.35 | 5.0% | 75.0% | 1.22 |

TABLE 11-continued

Mercury intrusion porosimetry data for macroporous silica samples used for column development. All samples contain 8 wt % of polymer.

| Sample | Total Pore Volume (cm$^3$) | Throughpore Volume (cm$^3$) | Bulk (Particle) Density (g/cm$^3$) | Interparticle Porosity (Throughpores) | Intraparticle Porosity (Mesopores) | Average Macropore diameter (μm) |
|---|---|---|---|---|---|---|
| DGS + PEO 10 kDa | 1.74 | 0.55 | 0.43 | 23.5% | 51.2% | 0.49 |
| DGS + PEO 100 kDa | 2.25 | 0.62 | 0.36 | 20.5% | 59.9% | 2.91 |

TABLE 12

BET data for several silica compositions

| | Precursor | DGS | DGS + PEO 2000 | DGS + PEO 10K |
|---|---|---|---|---|
| Surface Area Data (m$^2$/g) | Single point BET area | 581 | 565 | 560 |
| | Multi-point BET area | 596 | 575 | 574 |
| | Langmuir surface area | 1668 | 1653 | 1915 |
| | Micro pore area | 473 | 418 | 268 |
| | Meso pore area | 124 | 157 | 305 |
| | Cumulative adsorption surface area | 593 | 503 | 548 |
| | Cumulative desorption surface area | 586 | 520 | 648 |
| Pore Volume Data (cm$^3$/g) | Total pore volume | 0.467 (<56.2 nm) | 0.476 (<51.2 nm) | 0.506 (<54.2 nm) |
| | Cumulative adsorption pore volume (r = 30 – 1 nm) | 0.422 | 0.399 | 0.459 |
| | Cumulative desorption pore volume (r = 30 – 1 nm) | 0.430 | 0.414 | 0.506 |
| | Micro pore volume | 0.342 | 0.306 | 0.210 |
| Pore Size Data (nm) | Average pore radius | 1.56 | 1.65 | 1.76 |

TABLE 13

Substrates tested with Src PTK encapsulated in a sol-gel matrix.

| Substrate | MW (Da) |
|---|---|
| BiotinEEEEY | 1037 |
| Biotin(EEEEY)$_2$ | 1716 |
| Biotin(EEEEY)$_3$ | 2396 |
| Biotin(EEEEY)$_n$ | 44000 |
| YIYGSFKBiotin | 1104 |

TABLE 14

IC$_{50}$ values for PTK inhibitors.

| | IC$_{50}$ | |
|---|---|---|
| Inhibitor | Solution | Entrapped in Silica |
| Staurosporine | 300-500 nM | 500-700 nM |
| Src Kinase Inhibitor I | 500-700 nM | 600-800 nM |
| YIYGSFK | 0.8-1.2 mM | 1-1.4 mM |

We claim:

1. A method of preparing bimodal meso/macroporous siliceous materials comprising combining an organic polyol silane precursor with one or more additives under conditions suitable for hydrolysis and condensation of the precursor to a siliceous material and for phase separation to occur before gelation, wherein the one or more additives are one or more water-soluble polymers and wherein the conditions comprise combining the organic polyol silane precursor with the one or more additives at a pH in the range of about 4 to 10.

2. The method according to claim 1, wherein the one or more additives are water soluble polymers selected from one or more of polyethers, polyalcohols, polysaccharides, poly(vinyl pyridine), polyacids, polyacrylamides and polyallylamine.

3. The method according to claim 2, wherein the one or more additives are water soluble polymers selected from one or more of polyethylene oxide (PEO), polyethylene glycol (PEG), amino-terminated polyethylene oxide (PEO-NH$_2$), amino-terminated polyethylene glycol (PEG-NH$_2$), polypropylene glycol (PPG), polypropylene oxide (PPO), polypropylene glycol bis(2-amino-propyl ether) (PPG-NH$_2$), polyvinyl alcohol, poly(acrylic acid), poly(vinyl pyridine), poly(N-isopropylacrylamide) (polyNIPAM) and polyallylamine (PAM).

4. The method according to claim 3, wherein the one or more additives are water soluble polymers selected from one or more of PEO, PEO-NH$_2$, PEG, PPG-NH$_2$, polyNIPAM and PAM.

5. The method according to claim 3, wherein the one or more additives are water soluble polymers selected from one or more of PEO, PEO-NH$_2$ and polyNIPAM.

6. The method according to claim 5, wherein the one or more additives is PEO.

7. The method according to claim 6, wherein the PEO has a molecular weight that is greater than about 10,000 g/mol.

8. The method according to claim 7, wherein the PEO is used at a concentration of greater than about 0.005 g/mL of final solution.

9. The method according to claim 5, wherein the one or more additives is PEO-NH$_2$.

10. The method according to claim 9, wherein the PEO-NH$_2$ has a molecular weight that is greater than about 3,000 g/mol and is used at a concentration of about 0.005 g/mL of final solution.

11. The method according to claim 5, wherein the one or more additives is poly(N-isopropylacrylamide).

12. The method according to claim 11, wherein the poly(N-isopropylacrylamide) has a molecular weight that is about 10,000 g/mol and is used at a concentration of about 0.005 g/mL of final solution.

13. The method according to claim 1, wherein the one or more additives is a mixture of water soluble polymers.

14. The method according to claim 13 wherein the mixture of water soluble polymers comprises PEO and PEO-$NH_2$.

15. The method according to claim 1, wherein the organic polyol silane precursor is selected from the group consisting of diglycerylsilane (DGS), monosorbitylsilane (MSS), monomaltosylsilane (MMS), dimaltosylsilane (DMS) and dextran-based silane (DS).

16. The method according to claim 1, wherein the conditions comprise combining the organic polyol silane precursor with the one or more additives in aqueous solutions and with optional sonication to assist in dissolution.

17. A siliceous material prepared using the method according to claim 1.

18. The method according to claim 1, further comprising combining the organic polyol silane and one or more additives in the presence of one or more biomolecules.

19. A method of preparing siliceous materials with low shrinkage characteristics comprising:
(a) combining an aqueous solution of one or more compounds of Formula I:

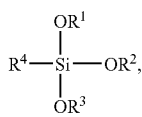

wherein $OR^1$, $OR^2$ and $OR^3$ are the same or different and represent a group that is hydrolyzed under normal sol-gel conditions to provide Si—OH groups; and $R^4$ is group that is not hydrolyzed under normal sol-gel conditions, with an aqueous solution of an organic polyol silane precursor;
(b) adjusting the pH of the solution in (a) to about 4-11.5;
(c) allowing the solution of (b) to gel;
(d) aging the gel of (c); and
(e) drying the aged gel in air.

20. The method according to claim 19, wherein $OR^1$, $OR^2$ and $OR^3$ are the same or different and are derived from organic di- or polyols.

21. The method according to claim 20, wherein $OR^1$, $OR^2$ and $OR^3$ are the same or different and are derived from sugar alcohols, sugar acids, saccharides, oligosaccharides or polysaccharides.

22. The method according to claim 20, wherein $OR^1$, $OR^2$ and $OR^3$ are the same or different and are derived from allose, altrose, glucose, mannose, gulose, idose, galactose, talose, ribose, arabinose, xylose, lyxose, threose, erythrose, glyceraldehydes, sorbose, fructose, dextrose, levulose, sorbitol, sucrose, maltose, cellobiose, lactose, dextran (500-50,000 MW), amylose, pectin, glycerol, propylene glycol or trimethylene glycol.

23. The method according to claim 22, wherein $OR^1$, $OR^2$ and $OR^3$ are the same or different and are derived from glycerol, sorbitol, maltose, trehalose, glucose, sucrose, amylose, pectin, lactose, fructose, dextrose and dextran.

24. The method according to claim 22, wherein $OR^1$, $OR^2$ and $OR^3$ are the same or different and are derived from glycerol, sorbitol, maltose or dextran.

25. The method according to claim 19, wherein $OR^1$, $OR^2$ and $OR^3$ are the same or different and are selected from $C_{1-4}$alkoxy, aryloxy and arylalkyleneoxy.

26. The method according to claim 25, wherein $OR^1$, $OR^2$ and $OR^3$ are the same or different and are selected from $C_{1-4}$alkoxy, phenyloxy, naphthyloxy and benzyloxy.

27. The method according to claim 26, wherein $OR^1$, $OR^2$ and $OR^3$ are the same or different and are selected from $C_{1-4}$alkoxy.

28. The method according to claim 27, wherein $OR^1$, $OR^2$ and $OR^3$ are all ethoxy.

29. The method according to claim 19, wherein $R^4$ is selected from the group consisting of:
polyol-(linker)-;
polymer-(linker)$_n$-; and

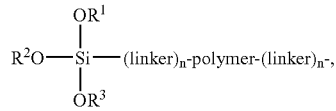

wherein n is 0-1.

30. The method according to claim 29, wherein the polyol is an organic di- or polyol.

31. The method according to claim 30, wherein the polyol is selected from the group consisting of a sugar alcohol, sugar acid, saccharide, oligosaccharide and polysaccharide.

32. The method according to claim 31, wherein the polyol is a selected from the group consisting of allose, altrose, glucose, mannose, gulose, idose, galactose, talose, ribose, arabinose, xylose, lyxose, threose, erythrose, glyceraldehydes, sorbose, fructose, dextrose, levulose, sorbitol, sucrose, maltose, cellobiose, lactose, dextran, (500-50,000 MW), amylose, pectin, glycerol, propylene glycol and trimethylene glycol.

33. The method according to claim 32, wherein the polyol is selected from the group consisting of glycerol, sorbitol, maltose, trehalose, glucose, sucrose, amylose, pectin, lactose, fructose, dextrose and dextran.

34. The method according to claim 33, wherein the polyol is selected from the group consisting of glycerol, sorbitol, glucose, maltose and dextrose.

35. The method according to claim 29 wherein the polymer is a water soluble polymer.

36. The method according to claim 35, wherein the polymer is selected from the group consisting of polyethylene oxide (PEO), polyethylene glycol (PEG), amino-terminated polyethylene oxide (PEO-$NH_2$), amino-terminated polyethylene glycol (PEG-$NH_2$), polypropylene glycol (PPG), polypropylene oxide (PPO), polypropylene glycol bis(2-amino-propyl ether) (PPG-$NH_2$), polyvinyl alcohol, poly(acrylic acid), poly(vinyl pyridine), poly(N-isopropylacrylamide) (polyNIPAM) and polyallylamine (PAM).

37. The method according to claim 36, wherein the water soluble polymer is selected from the group consisting of PEO, PEO-$NH_2$, PEG, PPG-$NH_2$, polyNIPAM and PAM.

38. The method according to claim 37, wherein the polymer is PEO.

39. The method according to claim 29, wherein the linker is selected from the group consisting of $C_{1-20}$alkylene, $C_{1-20}$alkenylene, organic ethers, thioethers, amines, esters, amides, urethanes, carbonates and ureas.

40. The method according to claim 29, wherein the compound of Formula I is selected from one or more of:

GluconamideSi (Compound 1);
MaltonamideSi (Compound 2);
DextronamideSi (Compound 3);
$(CH_2CH_2O)_p[(EtO)_3Si(C_3H_6)]_2$, p~4-5, average MW 200 (Compound 5a);
$(CH_2CH_2O)_p[(EtO)_3Si(C_3H_6)]_2$, p~13, average MW 600 (Compound 5b);
$(CH_2CH_2O)_p[(EtO)_3Si(C_3H_6)]_2$, p~44, average MW 2000 (Compound 5c); and
$(CH_2CH_2O)_p[(EtO)_3Si(C_3H_6)]_2$, p~227, average MW 10,000 (Compound 5d).

41. The method according to claim 19, further comprising combining the organic polyol silane and one or more additives in the presence of one or more biomolecules.

42. A method of preparing monolithic bimodal meso/macroporous silica materials comprising combining an organic polyol silane precursor with one or more additives selected from one or more water-soluble polymers and one or more compounds of Formula I:

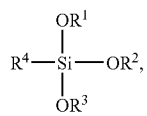

I wherein $OR^1$, $OR^2$ and $OR^3$ are the same or different and represent a group that is hydrolyzed under normal sol-gel conditions to provide Si—OH groups, $R^4$ is group selected from polymer-(linker)$_n$- and

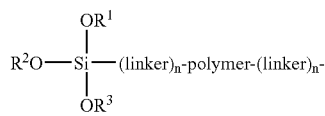

and n=0-1, under conditions suitable for hydrolysis and condensation of the precursor to a siliceous material and for phase transition to occur before gelation, wherein the conditions comprise combining the organic polyol silane precursor with the one or more additives at a pH in the range of about 4 to 10.

43. The method according to claim 42, wherein $R^4$ is

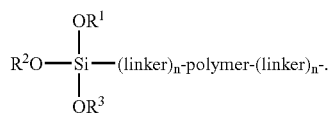

44. The method according to claim 43, wherein the linker group is a $C_{1-4}$alkylene group and n is 1.

45. The method according to claim 43, wherein $OR^1$, $OR^2$ and $OR^3$ are the same and are selected from $C_{1-14}$alkoxy.

46. The method according to claim 43, wherein the polymer is PEO.

47. The method according to claim 42 wherein the compound of Formula I is selected from the group consisting of:
$(CH_2CH_2O)_p[(EtO)_3Si(C_3H_6)]_2$, p~4-5, average MW 200 (Compound 5a);
$(CH_2CH_2O)_p[(EtO)_3Si(C_3H_6)]_2$, p~13, average MW 600 (Compound 5b);
$(CH_2CH_2O)_p[(EtO)_3Si(C_3H_6)]_2$, p~44, average MW 2000 (Compound 5c); and
$(CH_2CH_2O)_p[(EtO)_3Si(C_3H_6)]_2$, p~227, average MW 10,000 (Compound 5d).

48. The method according to claim 42, wherein the water soluble polymer is selected from one or more of PEO, PEO-$NH_2$ and poly(NIPAM).

49. A meso/macroporous silica monolith prepared using the method according to claim 42.

50. The method according to claim 42, further comprising combining the organic polyol silane and one or more additives in the presence of one or more biomolecules.

51. A method for the quantitative or qualitative detection of a test substance that reacts with, binds to and/or whose reactivity is catalyzed by an active biological substance, wherein said biological substance is encapsulated within a siliceous material, comprising:
(a) preparing the siliceous material comprising said active biological substance entrapped within a porous, silica matrix using a method according to claim 50;
(b) bringing said biological-substance-containing siliceous material into contact with a gas or aqueous solution comprising the test substance; and
(c) quantitatively or qualitatively detecting, observing or measuring the change in one or more characteristics in the biological substance entrapped within the siliceous material and/or, alternatively, quantitatively or qualitatively detecting, observing or measuring the change in one or more characteristics in the test substance.

52. The method according to claim 51, wherein the change in one or more characteristics of the entrapped biological substance is qualitatively or quantitatively measured by spectroscopy, utilizing one or more techniques selected from UV, IR, visible light, fluorescence, luminescence, absorption, emission, excitation and reflection.

53. A method of storing a biologically active biological substance in a silica matrix, wherein the biological substance is an active protein or active protein fragment, wherein the silica matrix prepared using a method according to claim 50.

54. A method of preparing a bimodal meso/macroporous monolithic silica chromatographic column comprising placing a solution comprising an organic polyol silane precursor and one or more additives selected from one or more water-soluble polymers and one or more compounds of Formula I:

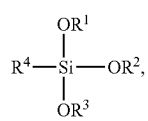

I wherein $OR^1$, $OR^2$ and $OR^3$ are the same or different and represent a group that is hydrolyzed under normal sol-gel conditions to provide a Si—OH group; $R^4$ is group selected from polymer-(linker)$_n$- and

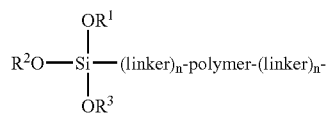

and n=0-1, in a column under conditions suitable for hydrolysis and condensation of the precursor to a siliceous material and for a phase transition to occur before gelation, wherein the conditions comprise combining the organic polyol silane precursor with the one or more additives at a pH in the range of about 4 to 10.

55. The method according to claim 54, wherein the solution further comprises one or more substances, which provide cationic sites that counterbalance an anionic charge of the silica to reduce non-selective interactions.

56. A chromatographic column comprising a bimodal meso/macroporous silica monolith prepared by combining an organic polyol silane precursor and one or more additives selected from one or more water-soluble polymers and one or more compounds of Formula I:

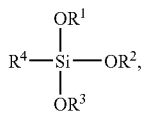
I wherein $OR^1$, $OR^2$ and $OR^3$ are the same or different and represent a group that is hydrolyzed under normal sol-gel conditions to provide Si—OH groups; $R^4$ is group selected from polymer-(linker)$_n$- and

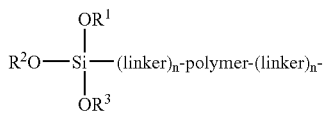

and n=0-1, under conditions suitable for hydrolysis and condensation of the precursor to a siliceous material and for phase transition to occur before gelation, wherein the conditions comprise combining the organic polyol silane precursor with the one or more additives at a pH in the range of about 4 to 10.

57. A method of preparing a bimodal meso/macroporous silica column having an active biomolecule entrapped therein comprising combining:
   a) a polyol-silane derived silica precursor;
   b) one or more additives selected from one or more water soluble polymers and one or more compounds of Formula I:

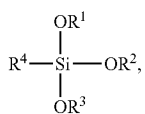
I wherein $OR^1$, $OR^2$ and $OR^3$ are the same or different and represent a group that is hydrolyzed under normal sol-gel conditions to provide Si—OH groups, $R^4$ is group selected from polymer-(linker)$_n$- and

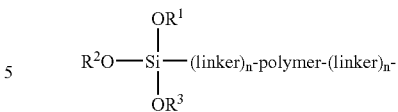

and n is 0-1; and
   c) a biomolecule;
under conditions suitable for hydrolysis and condensation of the precursor to a siliceous material and for phase separation to occur before gelation, wherein the conditions comprise combining the organic polyol silane precursor with the one or more additives at a pH in the range of about 4 to 10.

58. The method according to claim 57, wherein the one or more additives is one or more water soluble polymers or one or more compounds of Formula I, wherein $R^4$ is

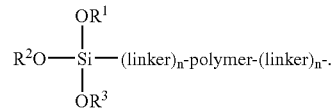

59. The method according to claim 57, wherein the organic polyol silane silica precursor, one or more additives and biomolecules are also combined with a substance which provides cationic sites that counterbalance an anionic charge of the silica to reduce non-selective interactions.

60. The method according to claim 59, wherein the substance which provides cationic sites that counterbalance an anionic charge of the silica to reduce non-selective interactions is aminopropyltriethoxysilane (APTES), PAM, PPG-NH$_2$ and/or PEG-NH$_2$.

61. A chromatographic column prepared using a method according to claim 57.

62. A method of performing immunoaffinity chromatography, sample cleanup, solid phase extraction or preconcentration of analytes, removal of unwanted contaminants, solid phase catalysis or frontal affinity chromatography comprising:
   (a) applying a sample to a column according to claim 61: and
   (b) performing immunoaffinity chromatography, sample cleanup, solid phase extraction or preconcentration of analytes, removal of unwanted contaminants, solid phase catalysis or frontal affinity chromatography.

63. A method of preparing siliceous materials with enhanced protein stabilizing ability comprising combining an organic polyol silane precursor with one or more additives under conditions suitable for hydrolysis and condensation of precursor to a siliceous material, wherein the one or more additives is selected from one or more trifunctional silanes of Formula I:

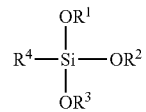
I wherein $OR^1$, $OR^2$ and $OR^3$ are the same or different and represent a group that is hydrolyzed under normal sol-gel conditions to provide a Si—OH group and $R^4$ is polyol-(linker)-.

64. The method according to claim 63, wherein the polyol in $R^4$ is derived from sugar alcohols, sugar acids, saccharides, oligosaccharides or polysaccharides.

65. The method according to claim 64, wherein the polyol in $R^4$ is derived from allose, altrose, glucose, mannose, gulose, idose, galactose, talose, ribose, arabinose, xylose, lyxose, threose, erythrose, glyceraldehydes, sorbose, fructose, dextrose, levulose, sorbitol, sucrose, maltose, cellobiose, lactose, dextran (500-50,000 MW), amylose, pectin, glycerol, propylene glycol or trimethylene glycol.

66. The method according to claim 65, wherein the polyol in $R^4$ is derived from glycerol, sorbitol, maltose, trehalose, glucose, sucrose, amylose, pectin, lactose, fructose, dextrose ort dextran.

67. The method according to claim 66, wherein the polyol in $R^4$ is derived from glycerol, sorbitol, glucose, maltose or dextran.

68. The method according to claim 67, wherein the polyol in $R^4$ is derived from glucose or maltose.

69. The method according to claim 63 wherein the one or more additives is GluconamideSi (Compound 1) and/or MaltonamideSi (Compound 2).

70. The method according to claim 63, wherein the protein is a kinase, luciferase, or urease or is Factor Xa.

71. The method according to claim 70, wherein the protein is Src protein tyrosine kinase.

72. The method according to claim 63, further comprising combining the organic polyol silane precursor and one or more additives with a substrate for the protein to be entrapped.

73. The method according to claim 72, wherein the protein is a kinase and the substrate is a source of phosphate.

74. The method according to claim 73, wherein the substrate is ATP.

* * * * *